United States Patent
Siegel et al.

(10) Patent No.: US 10,829,756 B2
(45) Date of Patent: Nov. 10, 2020

(54) DISCOVERY OF ENZYMES FROM THE ALPHA-KETO ACID DECARBOXYLASE FAMILY

(71) Applicant: Regents of the University of California, Oakland, CA (US)

(72) Inventors: Justin Siegel, Davis, CA (US); Steve Bertolani, Citrus Heights, CA (US); Wai Shun Mak, Sacramento, CA (US); James Liao, Los Angeles, CA (US); Stephen Tran, La Canada, CA (US); Ryan Marcheschi, Rockville, MD (US); James Thompson, Seattle, WA (US); David Baker, Seattle, WA (US)

(73) Assignees: The Regents of the University of California, Oakland, CA (US); The University of Washington, Seattle, WA (US)

( * ) Notice: Subject to any disclaimer, the term of this patent is extended or adjusted under 35 U.S.C. 154(b) by 0 days.

(21) Appl. No.: 15/752,543

(22) PCT Filed: Aug. 29, 2016

(86) PCT No.: PCT/US2016/049210
§ 371 (c)(1),
(2) Date: Feb. 13, 2018

(87) PCT Pub. No.: WO2017/040378
PCT Pub. Date: Mar. 9, 2017

(65) Prior Publication Data
US 2019/0010480 A1   Jan. 10, 2019

Related U.S. Application Data

(60) Provisional application No. 62/211,439, filed on Aug. 28, 2015.

(51) Int. Cl.
*C12N 9/88* (2006.01)
*C12P 7/04* (2006.01)
*C12N 15/52* (2006.01)

(52) U.S. Cl.
CPC ............... *C12N 9/88* (2013.01); *C12N 15/52* (2013.01); *C12P 7/04* (2013.01); *C07K 2319/70* (2013.01); *C12Y 101/01086* (2013.01); *C12Y 401/01001* (2013.01)

(58) Field of Classification Search
None
See application file for complete search history.

(56) References Cited

U.S. PATENT DOCUMENTS

2011/0201083 A1   8/2011   Liao et al.

FOREIGN PATENT DOCUMENTS

WO   2013/016724 A2   1/2013

OTHER PUBLICATIONS

Wei et al. Branched-chain 2-keto acid decarboxylases derived from Psychrobacter FEMS Microbiol Lett 346 (2013) 105-112).*
International Search Report in PCT/US2016/049210, dated Dec. 13, 2016.
Mak, et al. "Integrative genomic mining for enzyme function to enable engineering of a non-natural biosynthetic pathway." Nature communications 6 (2015): 10005.
Odokonyero, et al. "Loss of quaternary structure is associated with rapid sequence divergence in the OSBS family." Proceedings of the National Academy of Sciences 111, No. 23 (2014): 8535-8540.
D9VSN5, UniProtKB Submission No. D9VSN5_9ACTN, Oct. 1, 2014.
A0A0F4JHH3, UniprotKB Submission No. A0A0F4JHH3_9ACTN, Jun. 24, 2015.
A0A0F4K217 UniProtKB Submission No. A0A0F4K217_9ACTN, Jun. 24, 2015.

* cited by examiner

*Primary Examiner* — Iqbal H Chowdhury
(74) *Attorney, Agent, or Firm* — Kilpatrick Townsend and Stockton LLP

(57) ABSTRACT

2-ketoacid decarboxylase enzymes, compositions encoding for 2 ketoacid decarboxylase enzymes, and host cells comprising such enzymes or compositions are provided.

5 Claims, 32 Drawing Sheets

Specification includes a Sequence Listing.

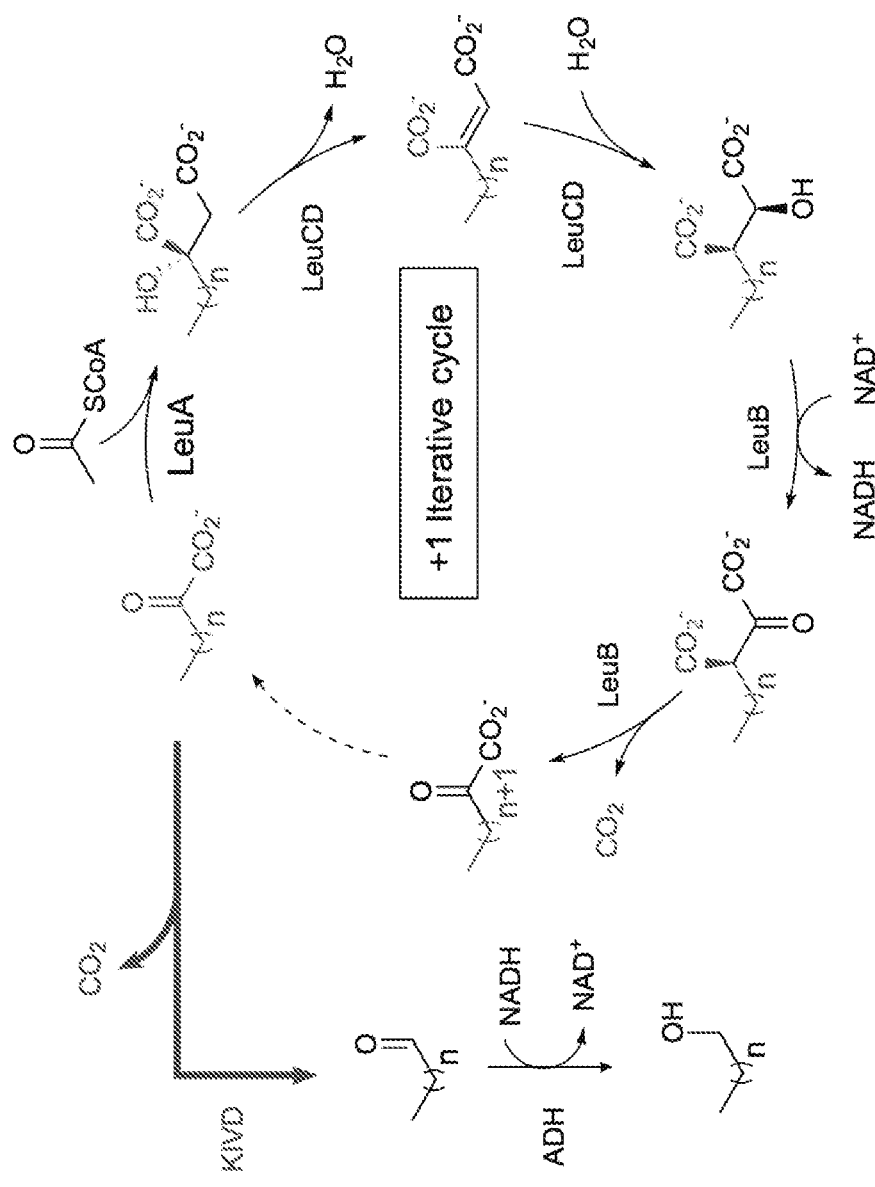
Figure 1 The synthetic recursive +1 pathway. This pathway employs enzymes LeuABCD from leucine biosynthesis for carbon chain elongation of 2-ketoacids. The enzyme ketoisovalerate decarboxylase (KIVD) performs the decarboxylation of 2-ketoacids and diverts carbon out from the +1 iterative cycle.

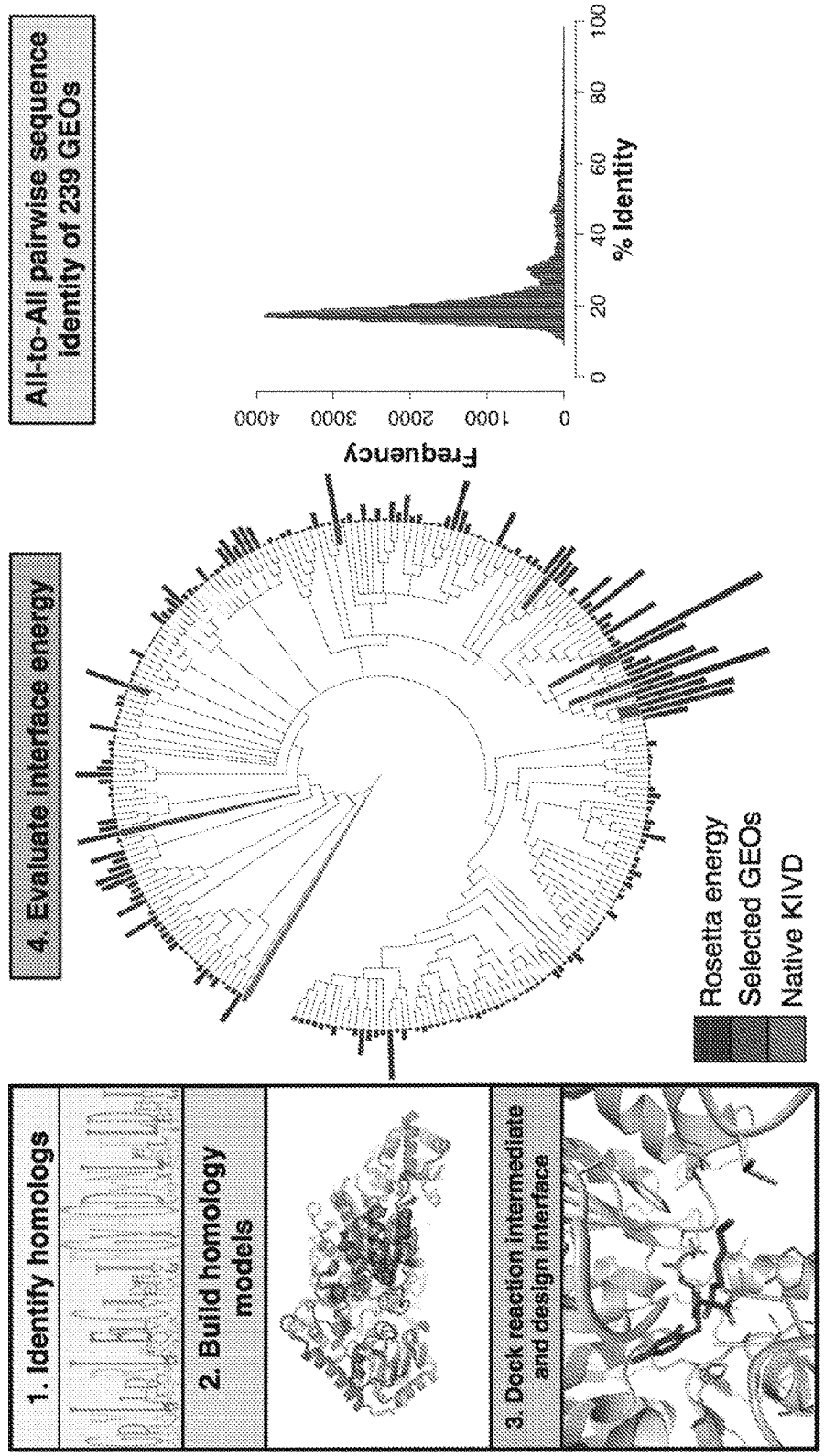

Figure 2. The computationally directed genomic enzyme-mining pipeline. (Left) GEOs were identified based on sequence homology to KIVD. Bioinformatics filters were used to identify a set of protein sequences from genomic databases that are predicted to be KIVD homologs and likely to be decarboxylases. Once identified, homology models were built to obtain a predicted ternary structure of each GEO. Ligand docking and design simulations were subsequently run in the presence of our target ligand (e.g. C8) to evaluate the potential protein-ligand interface energy. (Middle) a phylogenetic tree for the 239 GEOs was depicted with a bar chart above each sequence. The bar height indicated the predicted protein-ligand interface energy, the higher the bar the lower the energy. Bar height was scaled linearly relative to the lowest protein-ligand interface energy. 10 GEOs (Brown) were selected for experimental characterization. (Right) The pairwise sequence identity of all 239 GEOs to each other has a mode of 20%, indicating how diverse this set of sequences is.

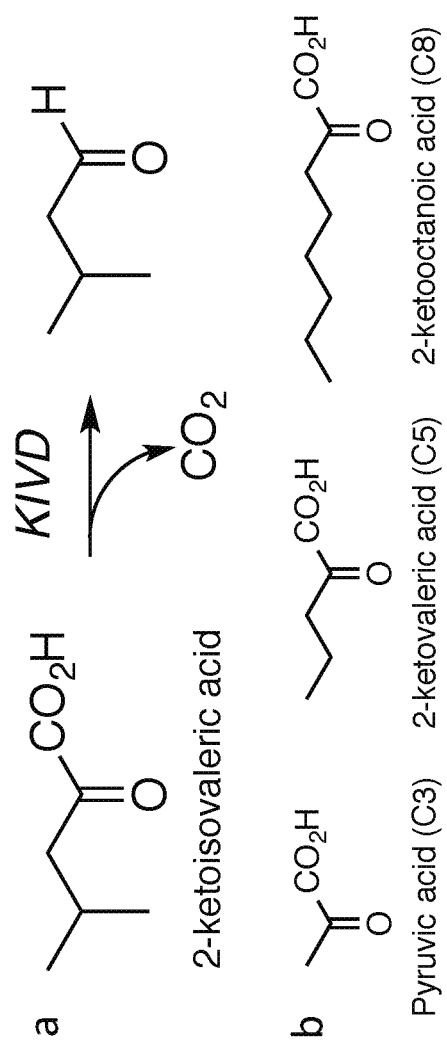
Figure 3. Characterized reaction specificities. (a) Ketoisovalerate decarboxylase (KIVD) utilizes various ketoacids as substrates to produce the corresponding aldehyde. (b) Ketoacids used for *in vitro* kinetic constants in addition to 2-ketoisovaleric acid.

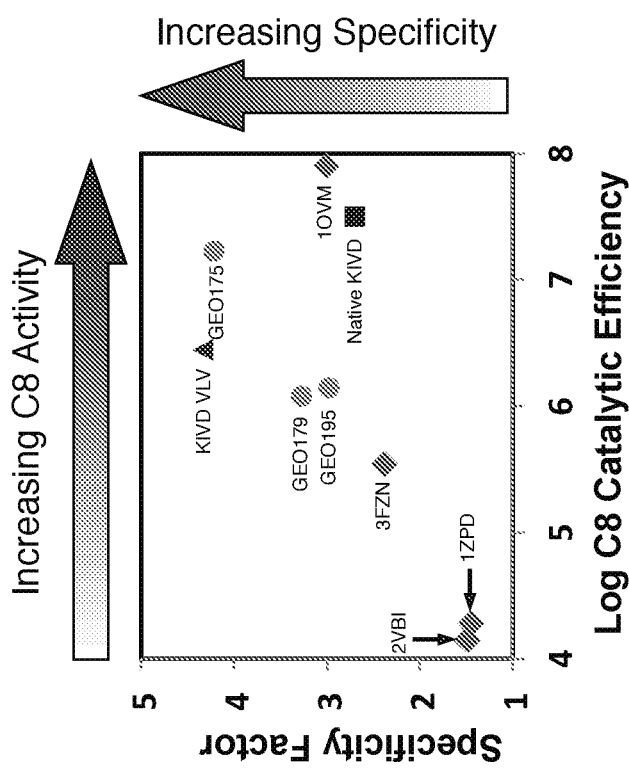

Figure 4. Catalytic efficiency and specificity of characterized ketoacid decarboxylases. Specificity factor is calculated as where the log scaled catalytic efficiencies for C8 relative to C5 and C3 are compared. The three active GEOs and the naively selected set of decarboxylases are represented in gold and green, respectively. Native KIVD and KIVD_VLV are depicted in black and blue, respectively. The genomic mining method and computational active site redesign approach both produced enzymes with enhanced specificity relative to native KIVD.

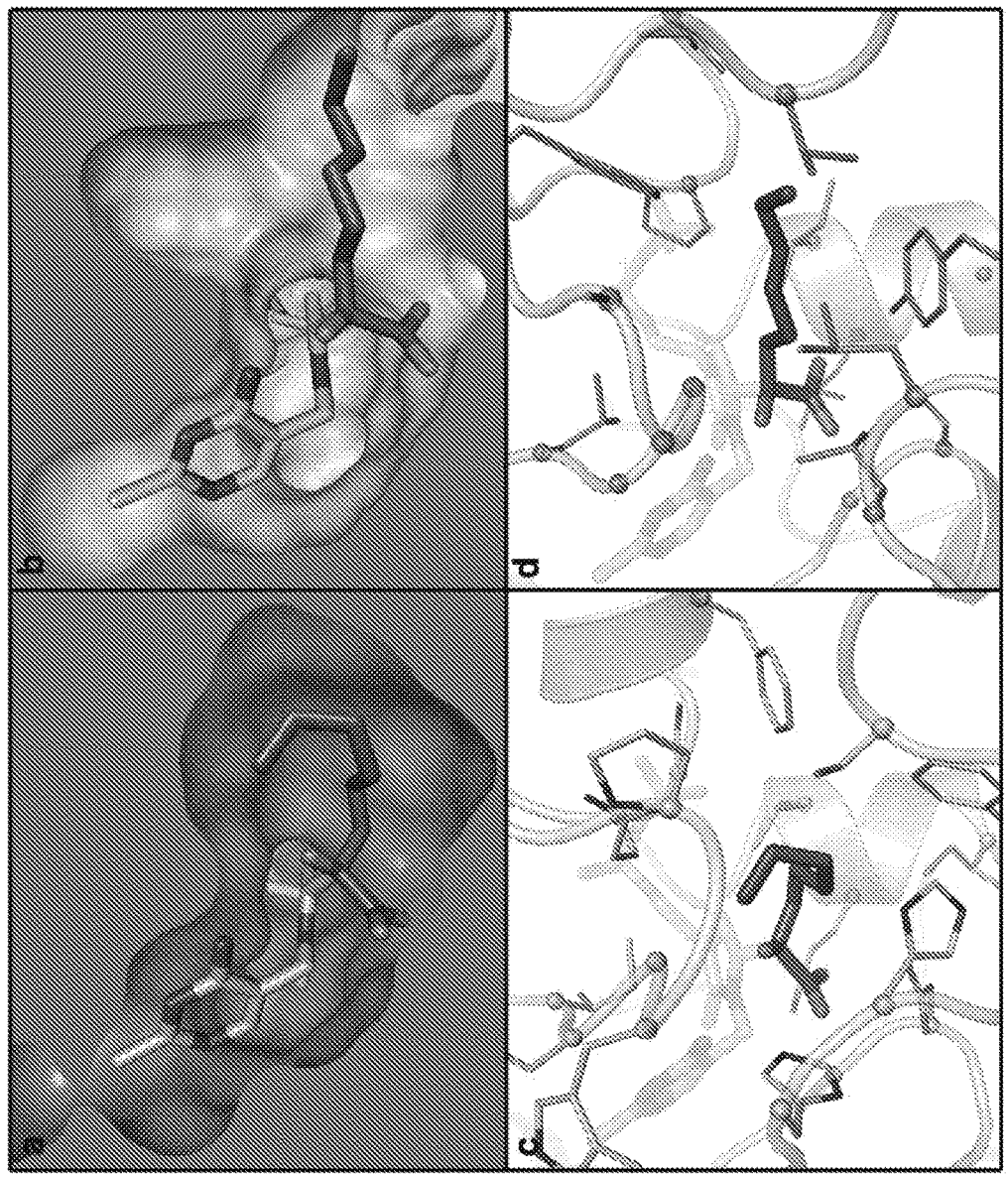

Figure 5. Molecular model of the C8 intermediate docked into KIVD (a, c) and GEO 175 (b, d). Cross sections of the space filled active site are represented in a and b where the C8 keto acid and TPP ligand are shown in brown and grey respectively. A detailed view of the amino acids within the active site are illustrated in c and d. Residues within 5 Å of C8 ligand are shown in sticks and their corresponding C-alpha are shown in spheres. Figure was generated using PyMol v1.7.4.[34]

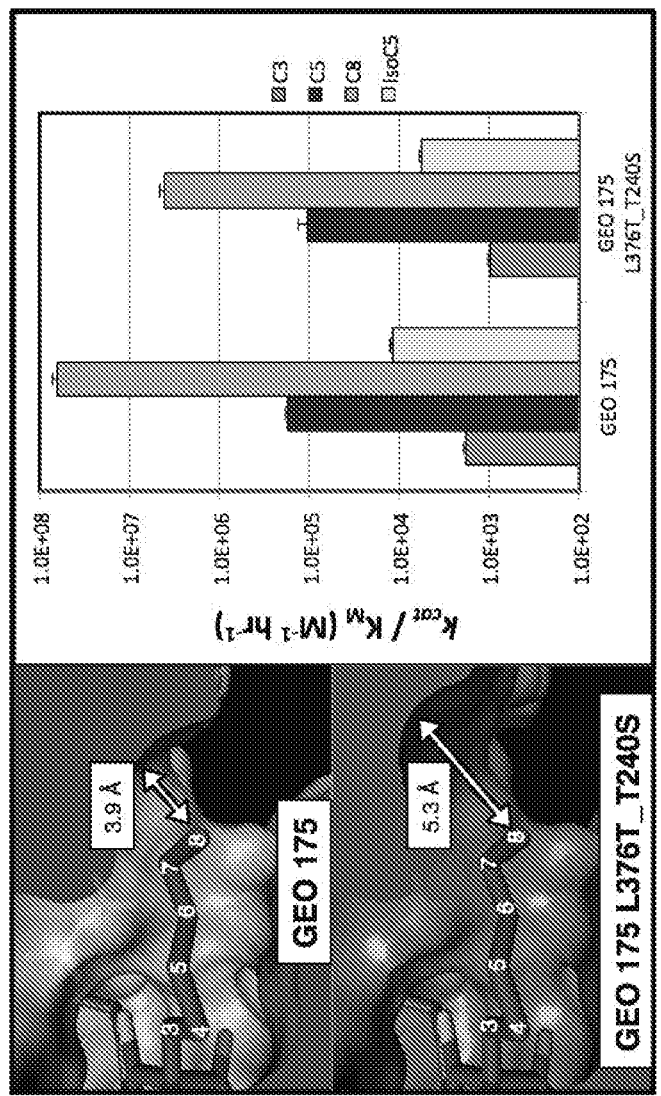

Figure 6. Kinetic characterization of GEO 175 and GEO 175 L376T_T240S. Kinetic constants were measured as described in materials and method. The substrate 2-ketooctanoate carbon chain numbering referred to in the text is numbered in white. According to the molecular model of GEO 175, the double mutation L376T_T240S is predicted to recede the pocket by 1.4 Å and remove interactions between the binding pocket and carbon 8 of the ketoacid alkyl chain. This mutant was observed to decrease catalytic efficiency on C8, but has a negligible effect on shorter chain substrates.

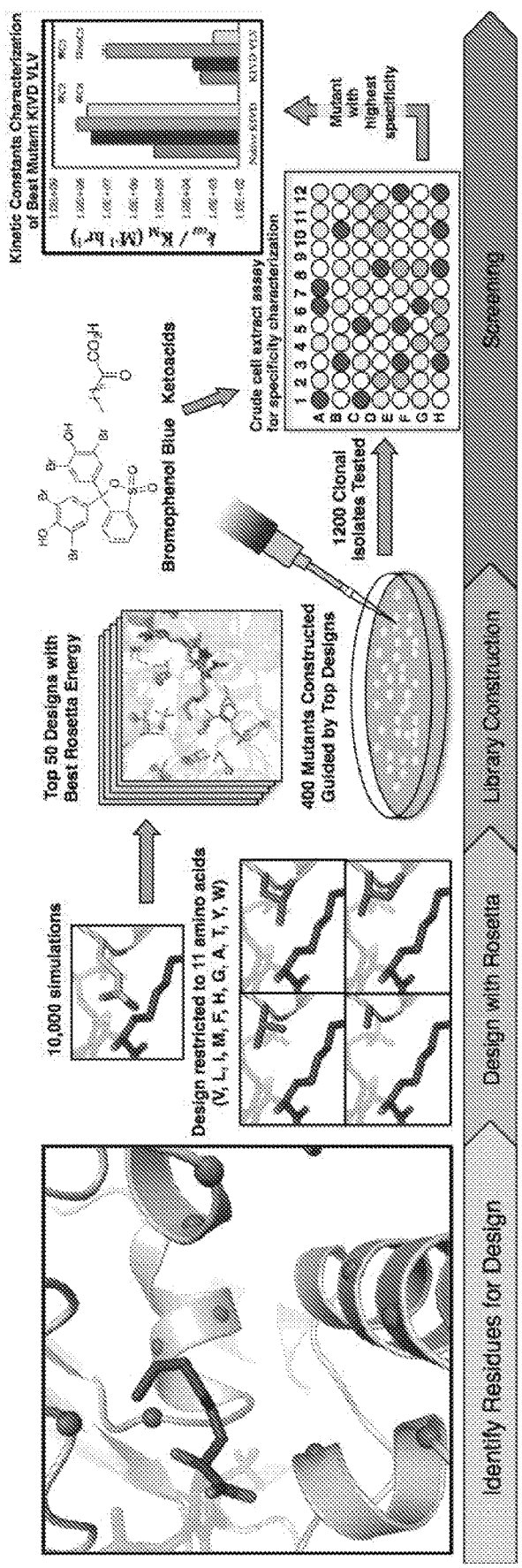

Figure 7 Screening process for identifying an engineered KIVD with altered substrate specificity. The design process started with identifying active site residues of KIVD (depicted in red). These amino acids were allowed to either remain native or sample any of eleven relatively hydrophobic amino acids. A total of 10,000 design simulations were ran and the amino acids identified in the 50 lowest energy designs were used to guide construction of a small library of roughly 400 KIVD mutants from the original combinatorial space of $10^{11}$ possible active site mutations. 1200 clonal isolates were screened for activity and specificity. The KIVD_VLV mutant was selected and subsequently purified for in vitro kinetic constant characterization.

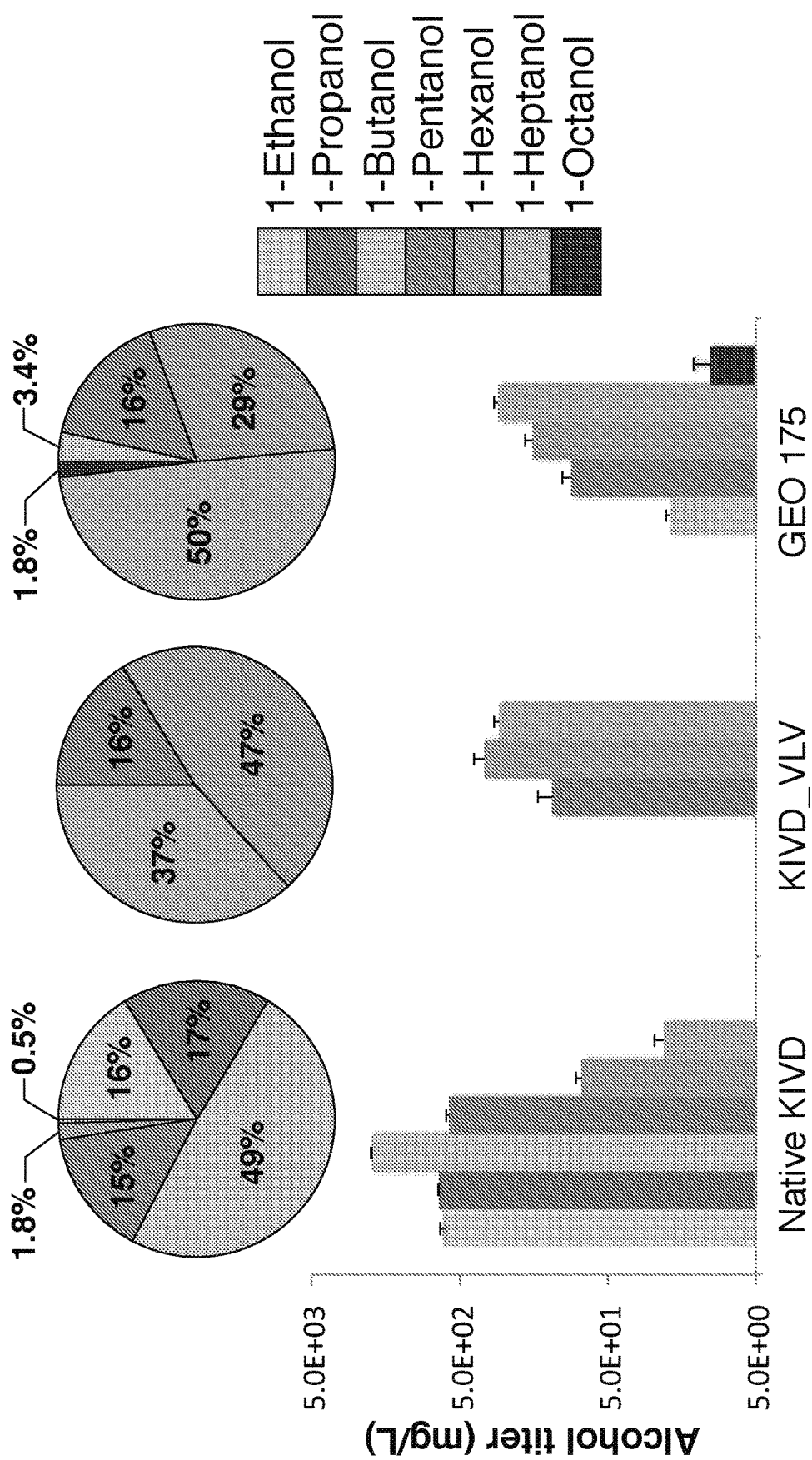

Figure 8. *In vivo* alcohol production of the synthetic recursive +1 pathway with native KIVD, KIVD_VLV, and GEO 175. Cells were incubated for forty hours in microaerobic conditions in a defined media as described in materials and methods. Each assay was performed in triplicate and titers reported if all three samples had observed product production above the limit of quantitation (5 mg/L).

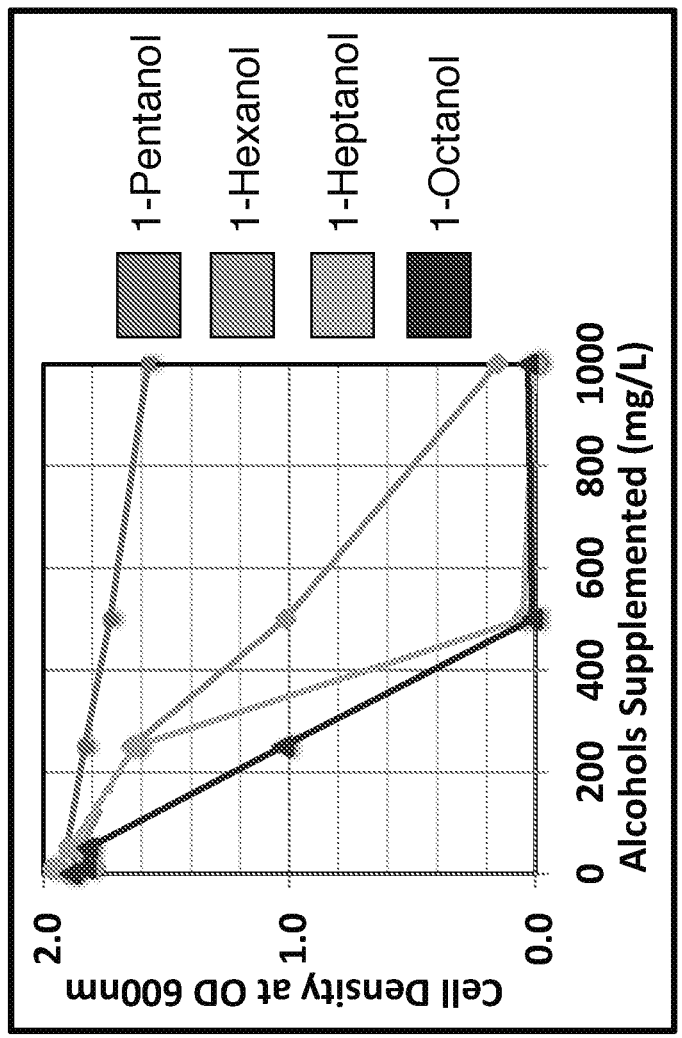
Figure 9. Toxicity as a function of alcohol chain length. The optical density of the engineered E. coli strain after a 7-hour growth was measured as a function of the alcohol concentration added to growth media at the beginning of incubation.

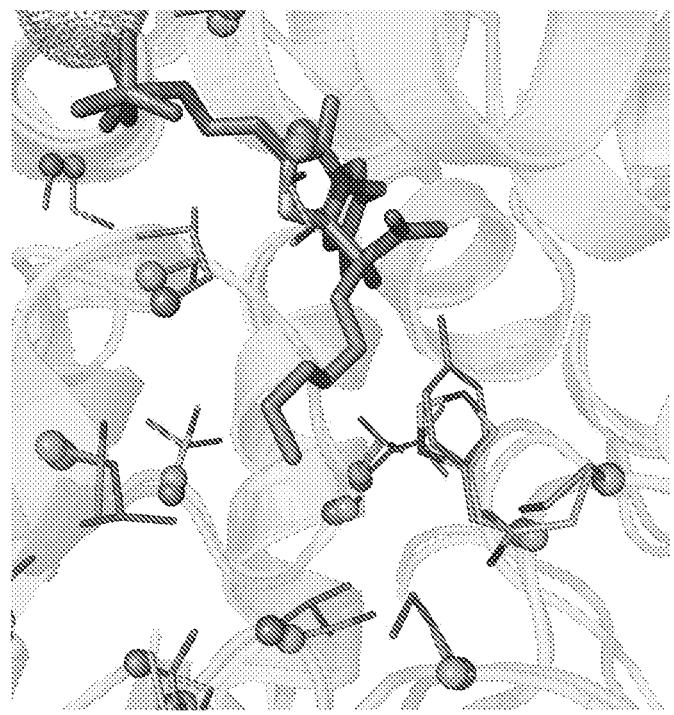
Figure 10. Overlay of active sites between GEO 175 (orange) and BFD (green). Resides that are different between the proteins are shown in sticks and their corresponding alpha carbons are shown in spheres.

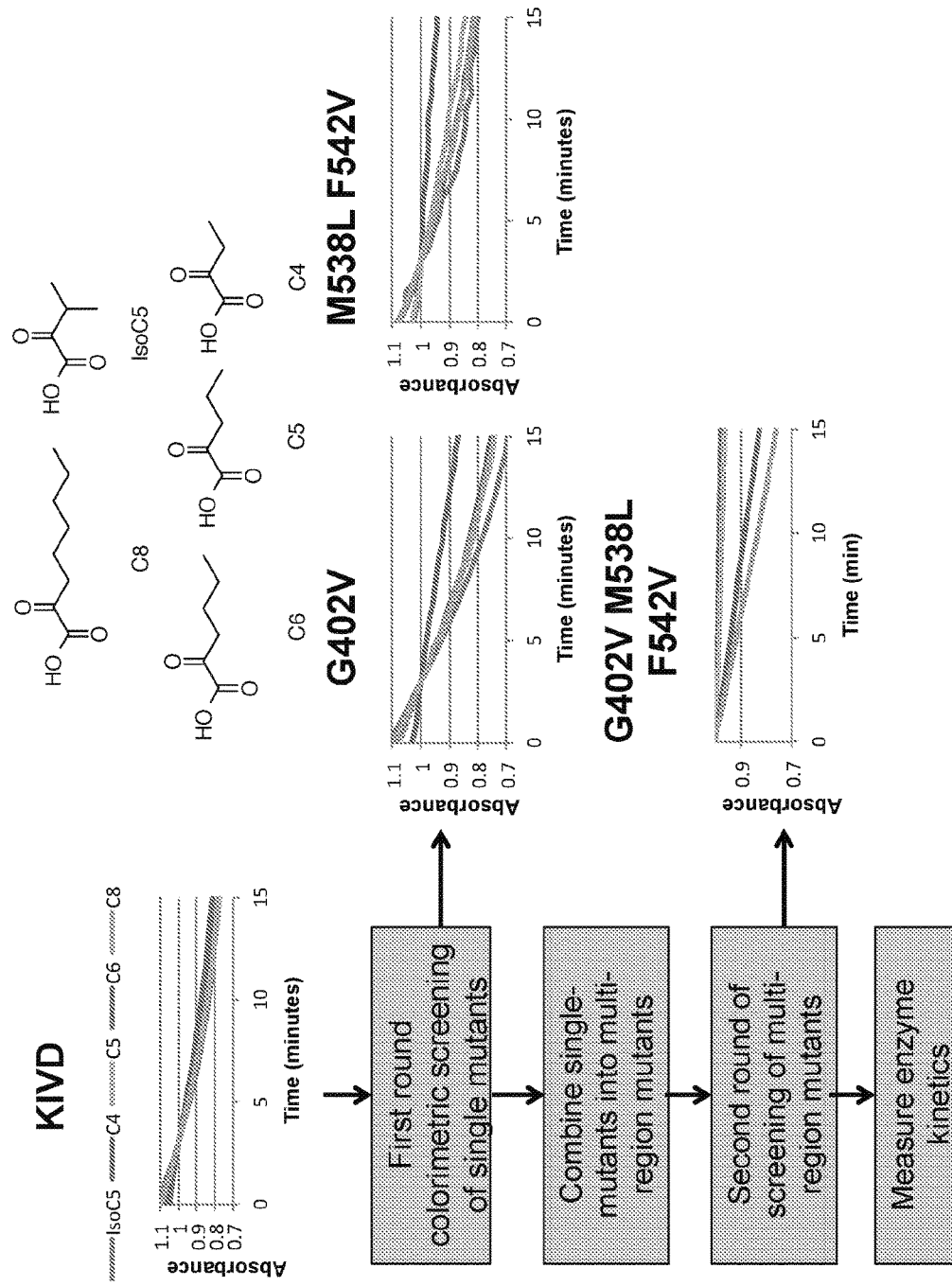

Figure 11. Screening process for identifying engineered KIVD with altered substrate specificity. Pertinent screening results/candidate mutants are shown (graphs) which contributed directly to finding KIVD_VLV. Colorimetric assays (graphs) measured approximate enzymatic activity of screened mutants for ketoisovalerate (IsoC5), 2-ketobutyrate (C4), 2-ketovalerate (C5), 2-ketohexanoate (C6), and 2-ketooctanoate (C8). Higher activity is shown by larger downwards slope of [Absorbance]/[Minute]; greater specificity, relative Kivd, was observed in mutants with reduced activity (lower downward slope) for IsoC5, C4, and C5, and only slightly affected or greater activity (similar or larger downward slope) for C6 and C8. First round high-throughput colorimetric screening of single mutants identified candidates such as G402V and M538L/F542V. Mutations from each region that showed potential in altering the specificity of kIVD were then combined to produce multi-region mutants through PCR-site directed mutagenesis using the plasmids of KIVD single region mutants as templates. These KIVD multi-region mutants, such as G402V M538L F542V (KIVD_VLV) were then screened a second time with the colorimetric assays. Enzyme kinetics was then measured for mutant KIVD_VLV.

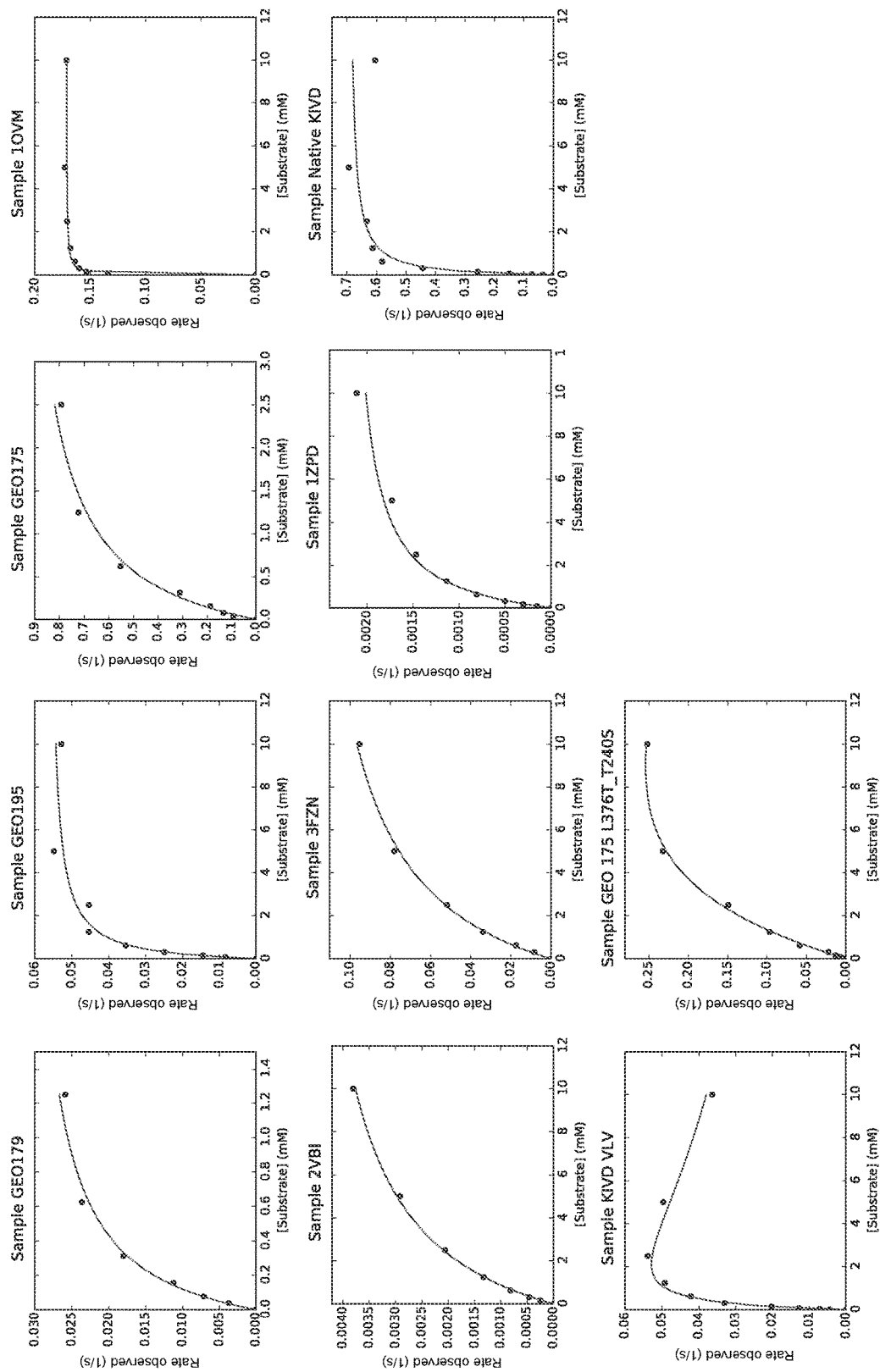
Figure 12. Michaelis-Menton curve fit of tested enzymes with C8 substrate.

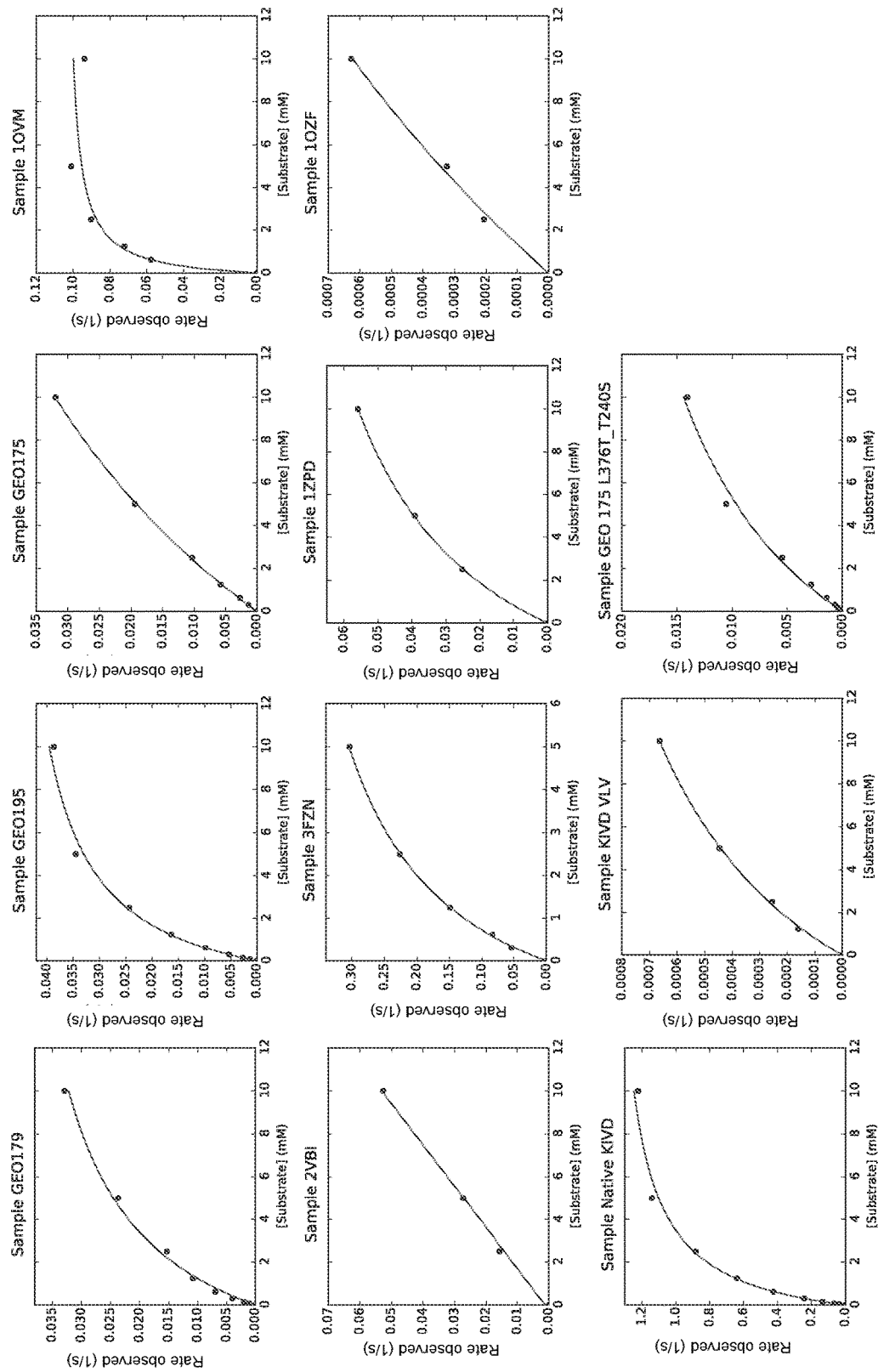
Figure 13. Michaelis-Menton curve fit of tested enzymes with C5 substrate.

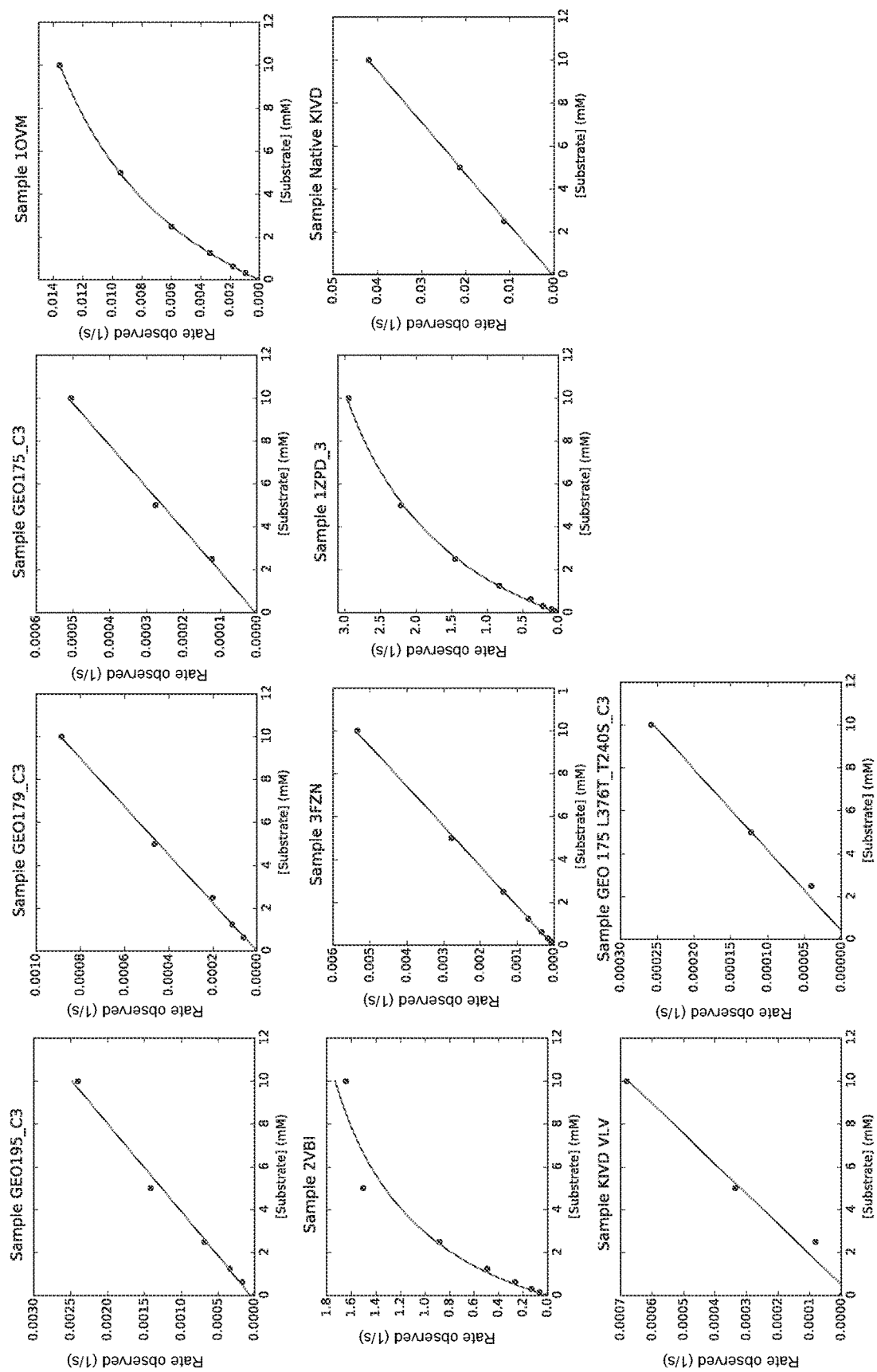
Figure 14. Michaelis-Menton curve fit of tested enzymes with C3 substrate.

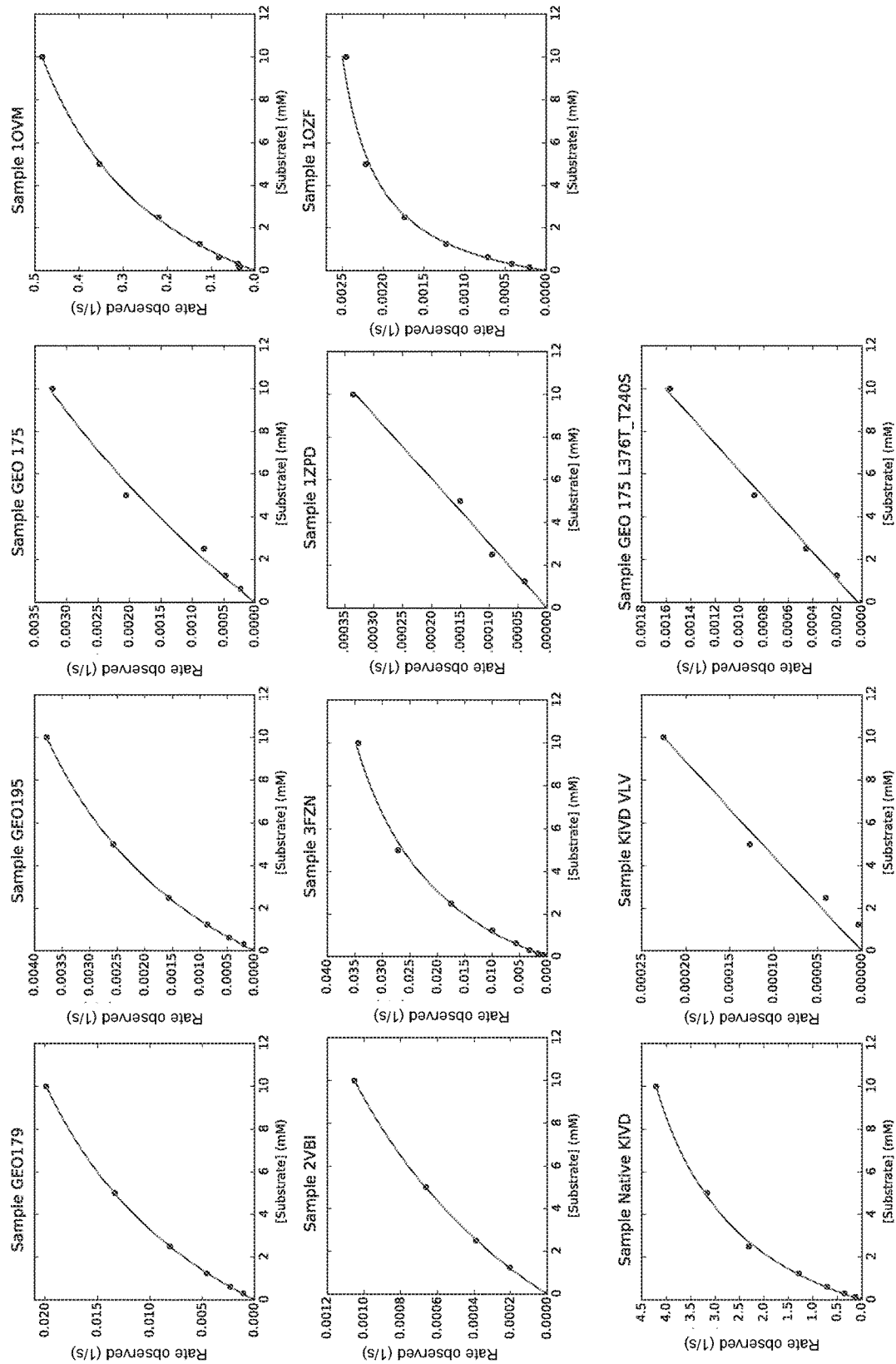
Figure 15. Michaelis-Menton curve fit of tested enzymes with isoC5 substrate.

| # | ID | # | ID | # | ID | # | ID |
|---|---|---|---|---|---|---|---|
| 1 | 2VBG | 41 | ZP_08570611 | 81 | YP_001208174 | 121 | ADP12107 | 161 | O53554 | 201 | YP_001070609 |
| 2 | YP_004211875 | 42 | YP_001236700 | 82 | YP_830466 | 122 | YP_004115182 | 162 | YP_003909136 | 202 | YP_004418205 |
| 3 | YP_004506975 | 43 | YP_001208817 | 83 | YP_675840 | 123 | ZP_08465980 | 163 | ZP_08198305 | 203 | YP_675476 |
| 4 | ZP_07949728 | 44 | YP_002353797 | 84 | ZP_06842871 | 124 | ZP_06711201 | 164 | ZP_07042487 | 204 | YP_675461 |
| 5 | ZP_07380174 | 45 | 2Q5Q | 85 | ZP_05126709 | 125 | ZP_08142152 | 165 | YP_004210411 | 205 | ZP_05074445 |
| 6 | YP_004116674 | 46 | YP_002379932 | 86 | ZP_05094980 | 126 | YP_511062 | 166 | YP_925359 | 206 | YP_004524050 |
| 7 | ZP_08307744 | 47 | O33112 | 87 | ZP_07031890 | 127 | ZP_07657182 | 167 | CAE38656 | 207 | ZP_06822743 |
| 8 | ZP_08461032 | 48 | P0A623 | 88 | YP_004416763 | 128 | ZP_07356713 | 168 | ZP_01901192 | 208 | ZP_01044868 |
| 9 | 1OVM | 49 | ZP_04998899 | 89 | EGD05600 | 129 | ZP_05100555 | 169 | ZP_07973795 | 209 | ZP_05844198 |
| 10 | ADP13207 | 50 | YP_004291227 | 90 | ZP_08543603 | 130 | YP_001240610 | 170 | CAM60234 | 210 | ZP_07985939 |
| 11 | YP_001281252 | 51 | YP_001353840 | 91 | ZP_06271645 | 131 | YP_001237056 | 171 | ZP_06711620 | 211 | BAJ49000 |
| 12 | YP_001177638 | 52 | 3D7K | 92 | ZP_06273171 | 132 | AAM12352 | 172 | YP_004020384 | 212 | ZP_01626788 |
| 13 | O53865 | 53 | YP_004519441 | 93 | ABI47993 | 133 | YP_001768986 | 173 | YP_002133221 | 213 | ZP_06710664 |
| 14 | ZP_04562872 | 54 | CAP40738 | 94 | ZP_07282849 | 134 | YP_004216045 | 174 | YP_001378281 | 214 | YP_509362 |
| 15 | AAL18557 | 55 | ZP_08275845 | 95 | YP_001208015 | 135 | YP_001280485 | 175 | YP_072904467 | 215 | YP_004076523 |
| 16 | Q9CBD6 | 56 | YP_004523976 | 96 | ZP_06370153 | 136 | ZP_00956146 | 176 | BAD32743 | 216 | ZP_08631155 |
| 17 | YP_003731250 | 57 | ZP_07706802 | 97 | ZP_05125236 | 137 | ZP_05033599 | 177 | YP_004522883 | 217 | AAR37826 |
| 18 | AEG26729 | 58 | YP_004081235 | 98 | ZP_06757044 | 138 | ZP_08591801 | 178 | YP_004083736 | 218 | ZP_01302664 |
| 19 | ZP_01623010 | 59 | ZP_08124815 | 99 | YP_830089 | 139 | ZP_06412949 | 179 | ZP_06547677 | 219 | ZP_05001859 |
| 20 | YP_003137934 | 60 | ZP_07949857 | 100 | YP_004230473 | 140 | CAM62618 | 180 | ZP_04607738 | 220 | CAP43929 |
| 21 | ZP_06368393 | 61 | ZP_08303118 | 101 | YP_002536327 | 141 | CAE37944 | 181 | ZP_05135002 | 221 | ZP_03267724 |
| 22 | YP_002380104 | 62 | YP_987677 | 102 | ZP_01130961 | 142 | CAP42719 | 182 | ZP_08119462 | 222 | ZP_06418208 |
| 23 | YP_004674227 | 63 | YP_686086 | 103 | YP_002377567 | 143 | ZP_01999289 | 183 | ZP_07280171 | 223 | ZP_07216338 |
| 24 | YP_004646634 | 64 | ZP_05068817 | 104 | YP_001242472 | 144 | ZP_08124133 | 184 | ZP_07380799 | 224 | ZP_01888096 |
| 25 | ZP_08317680 | 65 | ZP_06549025 | 105 | YP_004075455 | 145 | ZP_01902746 | 185 | YP_641501 | 225 | YP_004695810 |
| 26 | AAM49566 | 66 | YP_003810578 | 106 | YP_004505036 | 146 | YP_003607818 | 186 | YP_004085144 | 226 | ZP_04997132 |
| 27 | YP_004017390 | 67 | YP_004524326 | 107 | ZP_07378926 | 147 | ZP_07280108 | 187 | YP_830320 | 227 | ADI17252 |
| 28 | YP_001224592 | 68 | ZP_07282256 | 108 | ZP_07284792 | 148 | ZP_08317504 | 188 | ZP_04996569 | 228 | ZP_05780727 |
| 29 | 2VBI | 69 | BAF52673 | 109 | ZP_07278109 | 149 | YP_001769586 | 189 | CAQ52617 | 229 | CAE50484 |
| 30 | ZP_01125207 | 70 | YP_003909474 | 110 | CAK95977 | 150 | ZP_08272344 | 190 | YP_001684628 | 230 | CAC11911 |
| 31 | YP_004210504 | 71 | YP_004121185 | 111 | YP_004490314 | 151 | ZP_05102608 | 191 | AAA17301 | 231 | ZP_06273867 |
| 32 | 1ZPD | 72 | YP_001279645 | 112 | CAK95978 | 152 | ZP_01306645 | 192 | Q9HUR2 | 232 | YP_001275313 |
| 33 | YP_001806325 | 73 | CAE45665 | 113 | BAC79260 | 153 | YP_001505772 | 193 | YP_004080965 | 233 | YP_001240047 |
| 34 | AAA27685 | 74 | YP_831380 | 114 | ZP_08387358 | 154 | YP_001203581 | 194 | AEG30045 | 234 | ZP_06712511 |
| 35 | YP_730696 | 75 | YP_370152 | 115 | ZP_07278993 | 155 | ZP_07705403 | 195 | ZP_08846103 | 235 | ZP_07033476 |
| 36 | YP_003797329 | 76 | ZP_05101111 | 116 | YP_004230546 | 156 | YP_004416777 | 196 | ZP_07281735 | 236 | YP_004081191 |
| 37 | ZP_08315793 | 77 | AAR05436 | 117 | ZP_06841705 | 157 | ZP_07282273 | 197 | YP_047867 | 237 | ZP_08333578 |
| 38 | YP_01079084 | 78 | YP_001203568 | 118 | ACR33042 | 158 | ZP_07674873 | 198 | YP_004317430 | 238 | ZP_01725425 |
| 39 | ZP_08074854 | 79 | YP_381143 | 119 | ZP_01749177 | 159 | YP_481591 | 199 | YP_045534047 | 239 | ZP_05285963 |
| 40 | CBE69591 | 80 | CAC11945 | 120 | ZP_08137686 | 160 | NP_484471 | 200 | YP_004077246 | | |

Figure 16. PDB code and accession numbers of GEOs modeled as listed on the phylogenetic tree depicted in Figure 2. Sequences were obtained from homologous sequence search in the Non-Redundant database using HMMER3.

| Protein Sequences |
|---|
| 3FZN |
| MASVHGTTYELLRRQGIDTTVFGNPGSNELPFLKDFPEPEDFRYITALQEACVGTADGYAQASRKPAFINLHSAAGTGNAMGALSNAWNSHSPLIVTAGQQTRAMIGVEALLTNVDAANLPRPLVKWSYEPASAAEVPHAMSRATHMASMAPQGPVYLSVPYDDW DKDADPQSHHLFDRHVSSSVRLNDQDLDILVKALNSASNPAIVLGPDVDAANANADCVMLAERLKAPVWVAPSAPRCPFPTRHPCFRGLMPAGIAAISQLLEGHDVVLVIGAPVFRYHQYDPGQYLKPGTRLISVTCDPLEAARAPMGDAIVADIGAMASALANLV EESRQLPTAAPEPAKVDQDAGRLHPETVFDTLNDMAPENAIYLNESTSTTAQMWQRLNMRNPGSYYFCAAGGLGFALPAAIGVQLAEPERQVIAVIGDGSANYSISALWTAAQYNIPTFVIMNNGTYGALRWFAGVLEAENVPGLDVPGIDFRALAKGYGVQA LKADNLEQLKGSLQEALSAKGPVLIEVSTVSPVKGSTENLYFQSGALE |
| 2VBI |
| MTYTVGMYLAERVQIGLKHHFAVAGDYNLVELDQLLLNKDMVKQTYCCNELNCGFSAEGYARSNGAAAAVVTFSVGAISAMNALGGAYAENLPVILISGAPNSNDQGTGHILRHTIGKTDYSYQLEMARQYTCAAESTTDATHSAPAKIDHVIRTALRERKPAYLDIAC NIASEPCVRPGPVSSLLSEPEIDHTSLKAAVDATVALLEKSASPVMLLGSKLRAANALAATETLADKLQCAVTIMAAAKGFFPEDHAGFRGLYWGEVSNPGVQELVETSDALLCIAPVFNDYSTVGWSAWPKGPNVILAEPDRVTVDGRAYDGFTLRAFLQALAEKAP ARPASAQKSSVPTCSLTATSDEAGLTNDEIVRHINALLTSNTTLVAETGDSWFNAMRMTLPRGARVELEMQWGHIGWSVPSAFGNAMGSQDRQHVVMVGDGSFQLTAQEVAQMVRYELPVIIFLINNRGYVIEIAIHDGPYNYIKNWDYAGLMEVFNAGEGHG LGLKATTPKELTEAIARAKANTRGPTLIECQIDRTDCTDMLVQWGRKVASTNARKTTLAGSTENLYFQSGALE |
| 1ZPD |
| MSYTVGTTYLAERLVQIGLKHHFAVAGDYNLVCLDNLLNKNMEQYCCNELNCGFSAEGYARRAKGAAAAVVTYSVGALSAFDAIGGAYAENLPVILISGAPNNNDHAAGHVLRHALGKTDYHYQLEMAKNITAAAEAIYTPEEAPAKIDHVIKTALREKKPVYLEAC NIASMPCAAPGPASALFNDEASDEASLNAAVDETLKFIANRDKVAVLVGSKLRAAGAEEAAVKFTDALGGAVATMAAAKSFFPEENALYIGTSWGEVSPGVEKTMKEADAVIALAPVFNDYSTTGWTDIPDPKKLVLAEPRSVVVNGIRFPSVHLKDYLTRLAQKVS KKTGSLDFFKSLNAGELKKAAPADPSAPLVNAEIARQVEALLTPNTTVIAETGDSWFNAQRMKLPNGARVEYEMQWGHIGWSVPAAFGYAVGAPERRNLMVGDGSFQLTAQEVAQMVRLKLPVIIFLINNYGYTIEVMIHDGPYNNIKNWDYAGLMEVFNGNG GYDSGAAKGLKAKTGGELAEAIKVALANTDGPTLIECFIGREDCTEELVKWGKRVAAANSRKPVNKVVGSTENLYFQSGALE |
| ZP_08570611 |
| MSSINSFTVADYLTRCHQIGLRKYFQVPGDYVANFMDALEQFNGIEAVGDLTELGAGYAADGYARLTGIGAVSVQFGVGTFSVLNAIAGSYVERNPVVVITASPSTGNRKTKETGVLFHHSTGDLLADSKVFANVTVAAEVLSDPSDARQKIDKALTLATTFRRPYL EAWQDVWGLACEKPEGELKAIPLISEEGALKAMLADSLKLLNSARQPLVLLGVEINRFGLQDAVLDLLKASGLPYSTTSLAKTVISENEGIFVGTYADGASFPATVEYIEKADCVLALGVIFTDDYLTMLSKQFDQMIVVNNDETSRLGHAYYHQLYLADFILQLTDEIKKS SLYPRQNSALPLLPPQPQITPALLQQQLSYQNFFDLFYGYLQHQLQDNISILLGESSSLYMSARLYGLPQDSFIADAAWGSLGHETGCVTGIAYASDKRAMAIAGDGGFMMMCQCLSTISRHQLNSVVFVISNKVYAIEQSFVDICAFAKGGHFAPFDLLPTWDYLSL AKAFSVEGYRVQNGEELLQALEHIMTQKDKPALVEVVIQSQDLAPAMAGLVKSITGHTVEQCAIPTGSTENLYFQSGALE |
| YP_831380 |
| MTVTAAAYELLRSNRLTTTFGNPGDNELPLDAMPADFRYILGLHEGVVVGMADGFALQASGQAAFVNLHAASGTGNAMGALTNAWYSHTPLVITAGQQVRPMIGLEAMLSNVDAASLPRPLVKWSAEPALQAPDVPRALSQAITHATSDPKGPVVLSIPYDDW NQDTGNLSEHLSSRSVSRAGNPSAEQLDDILSALREAANPALVFGPDVDAARANHHAVRLAEKLAAPVWIAPAPRCPFPTRHPNFRGVLPASIAGISALLNGHDLIVVIGAPVFRYHQYQPGSYLPENSRLIHTCDAGEAARAPMGDALVADIGQTLRALADIIPQS KRPPLRPRVIPPVPDSQDDLLAPDAVFEVMNEVAPEDVVYNESVSTVTALWERVELKHPGSYYFPASGGLGFGMPAAVGVQLANDRRRVIAVIGDGSANYGITALWTAAQEKIPVVFIILNNGTYGALRAFAKLLNAENAAGLDVPGICFCAIAEGYGVEAHRITSL ENFKDKLSAALQSDTPTLLEVPTSTTSPFGSTENLYFQSGALE |
| ZP_06547677 |
| MKTTHSAAYATLLRRHGMTTTFGNPGSNELPFLKSFPEDFQYVTGLHEGAVVGMADGYALASGKPAFVNLHAAAGTGNGMGALTNSWVSHSPLVITAGQQVRPMTGVEAMLANVDATQLPKPLVKWSYEPANAQDVPRALSQATHYANTTPKAPVYLSIPYDDW DQPSGPGVEHLIERDVQTAGTPDARQLQVLVQQVQDARNPVLVLGPDVDATLSNDHAVALADKLRMPVWIAPAASRCPPTRHPSFRGVLPAAIAGISKTLQGHDLIIVVGAPVFRYLQFAPGDYLPVGAQLLHITSDPLEATRAPMGHALVGDIRETLRVLAEEVV QQSRPYPEALAAPECVTDEPHHLHPETLFDVLDAVAPHDAIYVKESTSTVTAFWQRMNLRHPGSYYFPAAGGLGFGLPAAVGVQLAQPQRRVVALIGDGSANYGITALWTAAQYRIPVVFIILKNGTYGALRWFAGVLKAEDSPGLDVPGLDFCAIAKGYGVKAVH TDTRDSFEEAALRTALDANEPTVIEVPTLTIQPHGSTENLYFQSGALE |
| TOVM_P23234 |
| MRTPYCVADYLLDRLTDCGADHLTGVPGDYNLTQFLDHFDVIDSPDICWVGCANELNASYAADGYARCKGFAALLTTFGVGELSAMNGIAGSYAEHVPVLHIVGAPGTAAQQRGELLHHTLGDGEFRFHYHMSEPITVAQAVLTEQNALYEIDRVLTTMLRERRPGYL MLPADVAKKAATPPVNALTHKQAHADSACLKAFRDAAENKLAMSKRTALLADFLVLRHGLKHALQKWVKEVPMAHATMLMGKGIFDERQAGFYGTYSGSASTGAVKEAIEGADTVLCVGTRFTDTLTAGFTHQLTPAQTIEVQPHAARVGDVWFTGIPMNQAI ETLVELCKQHVHAGLMSSSSGAIPPQPDGSLTQENFWRTLQTFIRPGDIILADQGTSAFGAIDLRLPADVNFIVQPLWGSIGYTLAAAFGAQTACPNRRVIVLTGDGAAQLTIQELGSMLRDKQHPIILVLNNEGYTVERAIHGAEQRYNDIALWNWTHIPQALSLDP QSECWRVSEAEQLADVLEKVAHHERLSLIEVMLPKADIPPLLGALTKALEACNNAGSTENLYFQSGALE |

Figure 17. Protein sequences for all genes used in this study.

Figure 17 (continued).

Protein sequences for all genes used in this study.

| Library | Native | Mutations |
|---|---|---|
| 1 | D285<br>S286 | ADLF<br>FMSTWY |
| 2 | Q377<br>F381<br>F382 | AFMWQ(ILR*)[a]<br>ALF(SV)[a]<br>AFMW(IL)[a] |
| 3 | G402 | AILMTV(S)[a] |
| 4 | V461<br>I465 | AMWTV<br>IV |
| 5 | M538<br>F542 | AHLMV(T)[a]<br>AFHIMTVWY(L)[a] |

Figure 18. KIVD Mutants with Altered Specificity for Long-chain 2-Ketoacids from the Results of High-throughput Kinetic Assays. *(a) Potential mutations in parenthesis were included due to degenerate codon used for mutagenesis.

| Enzyme ID | Pyruvate (C3) | 2-keto Valerate (C5) | 2-keto octanoate (C8) | 2-keto isovalerate (isoC5) | Rosetta Energy (Ligand: TPP-C8) |
|---|---|---|---|---|---|
| GEO175 | 0.5 | 48.0 | 17000.0 | 3.3 | -14.0 |
| GEO179 | 0.9 | 100.0 | 1200.0 | 41.0 | -13.44 |
| GEO195 | 2.4 | 200.0 | 1400.0 | 8.0 | -12.5 |
| GEO240 | <0.2 | not tested | 67.0 | 1500.0 | -12.1 |
| GEO241 | 5.7 | not tested | 320.0 | 9.0 | -12.4 |
| GEO242 | 8.2 | not tested | 8300.0 | 680.0 | not tested |
| GEO243 | <0.2 | not tested | <0.2 | <0.2 | not tested |
| GEO244 | 78.0 | not tested | 10000.0 | 8500.0 | not tested |
| GEO245 | <0.2 | not tested | 6.6 | 1.0 | not tested |
| GEO246 | 0.6 | not tested | 61.0 | 2.6 | not tested |
| GEO247 | 1.8 | not tested | 260.0 | 0.8 | not tested |
| GEO248 | 10.0 | not tested | 12000.0 | 2100.0 | not tested |
| GEO249 | 41.0 | not tested | 28.0 | <0.2 | not tested |
| GEO250 | 0.7 | not tested | 43.0 | 6.7 | not tested |
| GEO251 | <0.2 | not tested | 1.1 | <0.2 | not tested |
| KIVD_VLV | 0.71 | 1.3 | 2800 | 0.24 | -11.08 |

$k_{cat}/K_M$ ($M^{-1} s^{-1}$)

*Figure 19*

| Alignment Position | Entry Position | Entry Amino Acids | Entry Secondary Structure |
|---|---|---|---|
| 36 | 23 | ['Y', 'V', 'N'] | ['Loop','beta-strand'] |
| 37 | 24 | ['P', 'V'] | ['Loop','beta-strand'] |
| 38 | 25 | ['G'] | ['Loop','turn',] |
| 39 | 26 | ['S', 'D', 'G', 'T'] | ['Loop','turn',] |
| 40 | 27 | ['A', 'G', 'F', 'N', 'T', 'V', 'Y'] | ['Loop','beta-strand','turn'] |
| 65 | 48 | ['A', 'Q', 'T', 'G', 'L'] | ['Helix','Loop','beta-strand','turn'] |
| 66 | 49 | ['A', 'S', 'N', 'G', 'V'] | ['Helix','Loop','beta-strand','turn'] |
| 71 | 54 | ['A'] | ['Helix','beta-strand'] |
| 88 | 71 | ['Q', 'A', 'S', '-', 'T'] | ['Helix','Loop','beta-strand','turn'] |
| 91 | 74 | ['G'] | ['Helix','Loop','turn'] |
| 92 | 75 | ['A', 'E', 'T', 'L', 'V'] | ['Helix','Loop'] |
| 95 | 78 | ['A', 'T', 'G'] | ['Helix','Loop','beta-strand'] |
| 98 | 81 | ['A', 'P', 'M', 'G', 'N'] | ['Helix','Loop','beta-strand'] |
| 129 | 112 | ['E', 'G', 'H', '-', 'N', 'Q', 'S'] | ['Helix','Loop','beta-strand','turn'] |
| 130 | 113 | ['-', 'N', 'P', 'S', 'T', 'V'] | ['Helix','Loop','beta-strand','turn'] |
| 311 | 286 | ['A', 'L', 'N', 'Q', 'P', 'S', 'T', 'V', 'Y'] | ['Helix','Loop','beta-strand','turn'] |
| 401 | 356 | ['A', 'E', 'D', 'G', 'H', '-', 'P', 'R'] | ['Helix','Loop','beta-strand','turn'] |
| 433 | 376 | ['A', 'I', 'M', 'L', 'P', 'V'] | ['Helix','beta-strand'] |
| 434 | 377 | ['F', 'I', 'T', 'W', 'V', 'Y'] | ['Helix','beta-strand'] |
| 435 | 378 | ['A', 'G', 'F', 'S', 'T', 'V'] | ['Helix','beta-strand'] |
| 436 | 379 | ['E', 'D', 'I', 'K', 'N', 'S'] | ['Helix','beta-strand'] |
| 437 | 380 | ['Q', 'E', 'D', 'T'] | ['Helix','Loop','beta-strand','turn'] |
| 439 | 382 | ['I', 'P', 'T', 'G', 'L'] | ['Helix','Loop','turn'] |
| 456 | 399 | ['E', 'G', 'H', 'K', 'Q', 'S', 'T', 'V'] | ['Helix','Loop','beta-strand','turn'] |
| 458 | 401 | ['A', 'C', 'F', 'I', 'H', 'L', 'Y'] | ['beta-strand','turn'] |
| 459 | 402 | ['G', 'F', 'N', 'Q', 'S', 'T', 'Y'] | ['Helix','Loop','beta-strand'] |
| 460 | 403 | ['F', 'M', 'L', 'Q', 'P', 'S', 'T'] | ['Helix','Loop','beta-strand','turn'] |
| 461 | 404 | ['A', 'C', 'G', 'Q', 'P', 'R', 'V'] | ['Helix','Loop','beta-strand','turn'] |
| 490 | 427 | ['H', 'S', 'N', 'P', 'V'] | ['Helix','beta-strand'] |
| 491 | 428 | ['I', 'L', 'V'] | ['beta-strand'] |
| 492 | 429 | ['A', 'C', 'L', 'G'] | ['beta-strand'] |
| 493 | 430 | ['I', 'F', 'L', 'G', 'V'] | ['beta-strand'] |
| 494 | 431 | ['I', 'T', 'L', 'V'] | ['Loop','beta-strand','turn'] |
| 495 | 432 | ['G'] | ['Loop','beta-strand','turn'] |
| 497 | 434 | ['A', 'G'] | ['Helix','Loop','turn'] |
| 517 | 454 | ['I', 'K', 'T', 'V'] | ['beta-strand'] |
| 518 | 455 | ['C', 'F', 'I', 'L', 'V', 'Y'] | ['beta-strand'] |
| 519 | 456 | ['I', 'F', 'L', 'V'] | ['beta-strand'] |
| 520 | 457 | ['I', 'C', 'L', 'V'] | ['beta-strand'] |
| 521 | 458 | ['C', 'F', 'I', 'M', 'L', 'V', 'Y'] | ['Turn','beta-strand'] |
| 522 | 459 | ['S', 'K', 'N'] | ['Helix','Loop','beta-strand','turn'] |
| 523 | 460 | ['D', 'N'] | ['Helix','Loop','turn'] |
| 524 | 461 | ['A', 'D', 'G', 'K', 'N', 'Q', 'S', 'R', 'T'] | ['Helix','Loop','turn'] |
| 525 | 462 | ['A', 'E', 'G', 'S', 'R', 'T'] | ['Helix','Loop','turn'] |
| 528 | 465 | ['I', 'A', 'M', 'L', 'V'] | ['Helix','beta-strand'] |
| 608 | 535 | ['D', 'H', '-', 'P', 'S', 'T', 'V'] | ['Helix','Loop','turn'] |

*Figure 21*

| Alignment Position | GEO175 Position | Active Site Amino Acids | Predicted Secondary Structure Profile |
|---|---|---|---|
| 35 | 22 | ['G'] | ['Loop','beta-strand'] |
| 36 | 23 | ['Y','V','N'] | ['Loop','beta-strand'] |
| 37 | 24 | ['P','V'] | ['Loop','beta-strand'] |
| 38 | 25 | ['G'] | ['Loop','turn'] |
| 39 | 26 | ['S','D','G','T'] | ['Loop','turn'] |
| 40 | 27 | ['A','G','F','N','T','V','Y'] | ['Loop','beta-strand','turn'] |
| 41 | 28 | ['N','E','V'] | ['Helix','Loop','beta-strand'] |
| 42 | 29 | ['Q','L','F'] | ['Helix','beta-strand'] |
| 45 | 32 | ['F','I','M','L','T','Y'] | ['Helix','Loop','beta-strand'] |
| 60 | 43 | ['A','L','G'] | ['Helix','Loop','beta-strand'] |
| 63 | 46 | ['Q','H','N'] | ['Helix','Loop'] |
| 64 | 47 | ['E'] | ['Helix','Loop','beta-strand'] |
| 65 | 48 | ['A','Q','T','G','L'] | ['Helix','Loop','beta-strand','turn'] |
| 66 | 49 | ['A','S','N','G','V'] | ['Helix','Loop','beta-strand','turn'] |
| 67 | 50 | ['A','G','V'] | ['Helix','beta-strand'] |
| 71 | 54 | ['A'] | ['Helix','beta-strand'] |
| 86 | 69 | ['L','T','V'] | ['Helix','beta-strand'] |
| 87 | 70 | ['Y','H','T','F'] | ['Helix','Loop','beta-strand','turn'] |
| 88 | 71 | ['A','G','V','L','I','P','F','Y','W','S','T','C','M','N','Q','K','R','H','D','E','-'] | ['Helix','Loop','beta-strand','turn'] |
| 89 | 72 | ['A','T','G'] | ['Helix','Loop','beta-strand','turn'] |
| 90 | 73 | ['A','P','C','G','V'] | ['Helix','Loop','turn'] |
| 91 | 74 | ['G'] | ['Helix','Loop','turn'] |
| 92 | 75 | ['A','E','T','L','V'] | ['Helix','Loop'] |
| 93 | 76 | ['T','G','L'] | ['Helix','Loop','beta-strand'] |
| 94 | 77 | ['H','S','N'] | ['Helix','Loop','beta-strand'] |
| 95 | 78 | ['A','T','G'] | ['Helix','Loop','beta-strand'] |
| 96 | 79 | ['I','A','M','L','V'] | ['Helix','Loop','beta-strand'] |
| 98 | 81 | ['A','P','M','G','N'] | ['Helix','Loop','beta-strand'] |
| 99 | 82 | ['I','F','L','T','V'] | ['Helix','Loop','beta-strand'] |
| 128 | 111 | ['A','G','H','L','Q','S','T'] | ['Helix','Loop','beta-strand'] |
| 129 | 112 | ['A','G','V','L','I','P','F','Y','W','S','T','C','M','N','Q','K','R','H','D','E','-'] | ['Helix','Loop','beta-strand','turn'] |
| 130 | 113 | ['A','G','V','L','I','P','F','Y','W','S','T','C','M','N','Q','K','R','H','D','E','-'] | ['Helix','Loop','beta-strand','turn'] |
| 263 | 240 | ['F','M','L','S','T','W','V'] | ['Helix','Loop','beta-strand','turn'] |
| 310 | 285 | ['E','F','I','H','S','R','W','V','Y'] | ['Helix','Loop','beta-strand','turn'] |
| 311 | 286 | ['A','L','N','Q','P','S','T','V','Y'] | ['Helix','Loop','beta-strand','turn'] |
| 312 | 287 | ['E','F','P','S','T','Y'] | ['Helix','Loop','beta-strand','turn'] |
| 315 | 290 | ['P','E','D','G','F'] | ['Helix','Loop','beta-strand','turn'] |
| 401 | 356 | ['A','G','V','L','I','P','F','Y','W','S','T','C','M','N','Q','K','R','H','D','E','-'] | ['Helix','Loop','beta-strand','turn'] |
| 416 | 360 | ['Q','P','T','H','V'] | ['Helix','Loop','beta-strand','turn'] |
| 433 | 376 | ['A','T','M','L','P','V'] | ['Helix','beta-strand'] |
| 434 | 377 | ['F','I','T','W','V','Y'] | ['Helix','beta-strand'] |
| 435 | 378 | ['A','G','F','S','T','V'] | ['Helix','beta-strand'] |
| 436 | 379 | ['E','D','I','K','N','S'] | ['Helix','beta-strand'] |
| 437 | 380 | ['Q','E','D','T'] | ['Helix','Loop','beta-strand','turn'] |
| 438 | 381 | ['A','S','C','G','V'] | ['Helix','Loop','beta-strand','turn'] |
| 439 | 382 | ['I','P','T','G','L'] | ['Helix','Loop','turn'] |

FIG. 22

| | | | |
|---|---|---|---|
| 440 | 383 | [A, G, N, Q, S, T, V] | ['Helix', 'Loop', 'turn'] |
| 455 | 398 | [C, E, D, G, M, N, S, R, T] | ['Helix', 'Loop', 'beta-strand', 'turn'] |
| 456 | 399 | [E, G, H, K, Q, S, T, V] | ['Helix', 'Loop', 'beta-strand', 'turn'] |
| 457 | 400 | [Y, N, W, F] | ['Helix', 'Loop', 'beta-strand', 'turn'] |
| 458 | 401 | [A, C, F, I, H, L, Y] | ['beta-strand', 'turn'] |
| 459 | 402 | [G, F, N, Q, S, T, Y] | ['Helix', 'Loop', 'beta-strand'] |
| 460 | 403 | [F, M, L, Q, P, S, T] | ['Helix', 'Loop', 'beta-strand', 'turn'] |
| 461 | 404 | [A, C, G, Q, P, R, V] | ['Helix', 'Loop', 'beta-strand', 'turn'] |
| 462 | 405 | [A, T, S, L, G] | ['Helix', 'Loop', 'beta-strand', 'turn'] |
| 464 | 406 | [Q, A, G, N] | ['Loop', 'beta-strand', 'turn'] |
| 465 | 407 | [I, S, T, G] | ['Loop', 'beta-strand', 'turn'] |
| 489 | 426 | [A, G, V, L, I, P, F, Y, W, S, T, C, M, N, Q, K, R, H, D, E, -] | ['Helix', 'Loop', 'beta-strand', 'turn'] |
| 490 | 427 | [H, S, N, P, V] | ['Helix', 'beta-strand'] |
| 491 | 428 | [I, L, V] | ['beta-strand'] |
| 492 | 429 | [A, C, L, G] | ['beta-strand'] |
| 493 | 430 | [I, F, L, G, V] | ['beta-strand'] |
| 494 | 431 | [I, T, L, V] | ['Loop', 'beta-strand', 'turn'] |
| 495 | 432 | [G] | ['Loop', 'beta-strand', 'turn'] |
| 496 | 433 | [E, D] | ['Loop', 'turn'] |
| 497 | 434 | [A, G] | ['Helix', 'Loop', 'turn'] |
| 498 | 435 | [A, S, G] | ['Helix', 'Loop'] |
| 516 | 453 | [A, P, T, L, V] | ['Helix', 'beta-strand', 'turn'] |
| 517 | 454 | [I, K, T, V] | ['beta-strand'] |
| 518 | 455 | [C, F, I, L, V, Y] | ['beta-strand'] |
| 519 | 456 | [I, F, L, V] | ['beta-strand'] |
| 520 | 457 | [I, C, L, V] | ['beta-strand'] |
| 521 | 458 | [C, F, I, M, L, V, Y] | ['Turn', 'beta-strand'] |
| 522 | 459 | [S, K, N] | ['Helix', 'Loop', 'beta-strand', 'turn'] |
| 523 | 460 | [D, N] | ['Helix', 'Loop', 'turn'] |
| 524 | 461 | [A, D, G, K, N, Q, S, R, T] | ['Helix', 'Loop', 'turn'] |
| 525 | 462 | [A, E, G, S, R, T] | ['Helix', 'Loop', 'turn'] |
| 526 | 463 | [Y, L] | ['Helix', 'Loop', 'turn'] |
| 527 | 464 | [A, K, T, G, N] | ['Helix', 'Loop', 'beta-strand', 'turn'] |
| 528 | 465 | [I, A, M, L, V] | ['Helix', 'beta-strand'] |
| 529 | 466 | [E, L, V] | ['Helix', 'beta-strand'] |
| 535 | 472 | [A, G, V, L, I, P, F, Y, W, S, T, C, M, N, Q, K, R, H, D, E, -] | ['Helix', 'Loop', 'beta-strand', 'turn'] |
| 536 | 473 | [A, G, V, L, I, P, F, Y, W, S, T, C, M, N, Q, K, R, H, D, E, -] | ['Helix', 'Loop', 'beta-strand', 'turn'] |
| 545 | 475 | [A, G, V, L, I, P, F, Y, W, S, T, C, M, N, Q, K, R, H, D, E, -] | ['Helix', 'Loop', 'beta-strand', 'turn'] |
| 547 | 477 | [Q, R, D, G, N] | ['Helix', 'Loop', 'beta-strand', 'turn'] |
| 599 | 526 | [E, D, N] | ['Helix', 'beta-strand'] |
| 600 | 527 | [A, T, L, V] | ['Helix', 'beta-strand'] |
| 601 | 528 | [E, T, H, K, M, L, P, V] | ['Helix', 'Loop', 'beta-strand'] |
| 603 | 530 | [A, D, G, L, Q, P, S, T] | ['Helix', 'Loop', 'beta-strand', 'turn'] |
| 604 | 531 | [A, G, V, L, I, P, F, Y, W, S, T, C, M, N, Q, K, R, H, D, E, -] | ['Helix', 'Loop', 'beta-strand', 'turn'] |
| 605 | 532 | [A, G, V, L, I, P, F, Y, W, S, T, C, M, N, Q, K, R, H, D, E, -] | ['Helix', 'Loop', 'beta-strand', 'turn'] |
| 607 | 534 | [A, G, V, L, I, P, F, Y, W, S, T, C, M, N, Q, K, R, H, D, E, -] | ['Helix', 'Loop', 'beta-strand', 'turn'] |
| 608 | 535 | [A, G, V, L, I, P, F, Y, W, S, T, C, M, N, Q, K, R, H, D, E, -] | ['Helix', 'Loop', 'beta-strand', 'turn'] |

>GEO175
------------MRTVRESALDVLRARGMTTVFGNPGSTELPMLKQFP--DD--
FRYVLGLQEAVVVGMADGFALASGTTGLVNLHTGPGTGNAMGAILNARANRTPMVVTAGQQVRAMLTMEA
LLTNPQSTLLPQPAVKWAYEPPR------
AADVAPALARAVQVAETPPQGPVFVSLPMDDFDVVLGEDEDRAAQRAAARTVTHAAAPSAEVVRRLAARLS
GARSAVLVAGNDVDASGAWDAVVELAERTGLPVWSAPTEGRVAFPKSHPQYRGMLPPAIAPLS--
RCLEGHDLVLVIGAPVFCYYPYVPGAHLPENTELVHLTRDADEAARAPVGD-AVVADLALTVRALLAELP----
----------A------REAAAPAARTARAESTAEVDGV-----------LTPLAAMTAIAQGA-
PANTLVVNESPSNLGQFHDATRIDTPGSFLFTAG-GGLGFGLAAAVGAQLGAPDR-----
PVVCVIGDGSTHYAVQALWTAAAYKVPVTFVVLSNQRYAILQWFAQVE------GAQGAPGLDI--
PGLDIAAVATGYGVRAHRATGFGELSKLVRESA-LQQDGPVLIDVPVTTELPTL----------------
>GEO243
-----------MELLSGGEMLVRALADEGVEHVFGYPGGAVLHIYDALFQQDK--
INHYLVRHEQAAGHMADAYSRATGKTGVVLVTSGPGATNTVTPIATAYMDSIPMVILSGQVASHLIGEDAF-
QETDMVGISRPIVKHSFQVRH------ASEIPAIIKKAFYIAASGRPGPVVVDIPKDATNPAE-
KFAYEYPEKVKMRSYQPPSRGHSGQIRKAIDELLSAKRPVIYTGGGVVQGNASALLTELAHLLGYPVTNTLM-
GLGGFPGDDPQFVGML-GMHGTYEANMAMHNADVILAIGAR-
FDDRVTNNPAKFCVNAKVIHIDIDPASISKTIMAHIPIVGAVEPVLQEMLTQLKQL------
NVSKPNPEAIAAWWDQINEWRKVHGLKFETPTDGT----------MKPQQVVEALYKAT-
NGDAIITSDVGQHQMFGALYYKYKRPRQWINSGGLGTMGVGLPYAMAAKLAFPDQ-----
QVVCITGEASIQMCIQELSTCKQYGMNVKILCLNNRALGMVKQWQDMNY--------
EGRHSSSYVESLPDFGKLMEAYGHVGIQIDHADELESKLAEAM-
AINDKCVFINVMVDRTEHVYPMLIAGQSMKDMWLGKGERT
>GEO250
MPANTAPNAQAAEVFTVRHAVINMLRELGMTRIFGNPGSTELPLFRDYP--ED--
FSYILGLQETVVVGMADGYAQATRNASFVNLHSAAGVGHAMANIFTAFKNRTPMVITAGQQTRSLLQFDPFL
HSNQAAELPKPYVKWSCEPAR------AEDVPQALARAYYIAMQEPRGPVFVSIPADDWD--------
VPCEPITLRKVGFETRPDPRLLDSIGQALEGARAPAFVVGAAVDRSQAFEAVQALAERHQARVYVAPMSGRCG
FPEDHALFGGFLPAM--
RERIVDRLSGHDVVFVIGAPAFTYHVEGHGPFIAEGTQLFQLIEDPAIAAWAPVGDAAV-GNIRMGVQELLAR--
-------------P--------LTHPRPALQPRPAIPAPAAPEPGR---------
LMTDAFLMHTLAQVRSRDSIIVEEAPGSRSIIQAHLPIYAAETFFTMCS-GGLGHSLPASVGIALARPDK-----
KVIGVIGDGSAMYAIQALWSAAHLKLPVTYIIVKNRRYAALQDFSRVF------
GYREGEKVEGTDLPDIDFVALAKGQGCDGVRVTDAAQLSQVLRDA--LRSPRATLVEVEVA-------------------
-----
>GEO242
-------------MYTVADYLLDRLKELGIDEVFGVPGDYNLQFLDHITARKD--
LEWIGNANELNAAYMADGYARTKGISALVTTF-
GVGELSAINGLAGSYAESIPVIEIVGSPTTTVQQNKKLVHHTLGDGDFLRFERIHEEVSAAIAHLSTENAPSEIDR
VLTVAMTEKR-PVYINLPIDIAE-----
MKASAPTTPLNHTTDQLTTVETAILTKVEDALKQSKNPVVIAGHEILSYHIENQLEQFIQKFNLPITVLPF-
GKGAFNEEDAHYLGTYTGSTTDESMKNRVDHADLVLLLGAK-
LTDSATSGFSFGFTEKQMISIGSTEVLFYGEKQETVQL-DRFVSALSTLSFS---------------R-------
FTDEMPSVKRLATPKVRDEK-------------LTQKQFWQMVESFLLQGDTVVGEQGTSFFGLT--
NVPLKKDMHFIGQPLWGSIGYTFPSALGSQIANKES-----
RHLLFIGDGSLQLTVQELGTAIREKLTPIVFVINNNGYTVEREIHGAT------EQYNDIPM-
WDYQKLPFVFGGTDQTVATYKVSTEIELDNAMTRAR-TDVDRLQWIEVVMDQNDAPVLLKKLAKIFAKQNS-
-----
>GEO245
-----------MVSRPARVAILEQLRADGVRYMFGNPGTVEQGFLDELRNFPD--
IEYILALQEAGVVGLADGYARATRTPAVLQLHTGVGVGNAVGMLYQAKRGHAPLVAIAGEAGLRYDAMEAQ
MA-VDLVAMAEPVTKWATRVVD------PESTLRVLRRAMKVAATPPYGPVLVVLPADVMD-----
RDTSEAAVPTSYVDFAATPDPQVLDRAAELLAGAERPIVIAGDGVHFAGAQEELGRLAQTWGAEVWGADW-

FIG. 24

AEVNLSVEHPAYAGQL-
GHMFGDSSRRVTGAADAVLLVGTYALPEVYPALDGVFADGAPVVHIDLDTDAIAKNFPVDLGLAADPRRALD
GLARALERRMSPESRARAGEWFTGRSAQRSYEIAAAREQDEAALAPDA-----------LPVTAFLQELARQL-
PEDAVVFDEALTASPDVTRHLPPTRPGHWHQTRG-GSLGVGIPGAIAAQLAHPDR-----
TVVGFTGDGGSLYTIQALWTAARYDIGATFVICNNSSYKLLELNIEEYWKSVDVAAHEQPEMFDLARPAIDFV
ALSRSLGVPAVRVEKPDQAKAAVEQA--LGTPGPFLIDLVTGRGRED---------------------
>GEO251
--------------MNVAELVGRTLAELGVGAAFGVVGSGNFVVTNGLRA-GG--
VRFVAARHEGGAASMADAYARMSGRVSVLSLHQGCGLTNALTGITEAAKSRTPMIVLTGDTAASAVLSNFRI
GQ---DALATAVGAVPERVHS------APTAVADTVRAYRTAVQQRR-TVLLNLPLDVQA-----
QEAPEAVEIPKVRGPAPIRPDAGMVAKLADLLAEARRPVFIAGRGARASAV--PLRELAEISGALLATSAV-
AHGLFH-DDPFSLGI-SGGFSSPRTADLIVDADLVIGWCA-
LNMWTTRHGTLLGPAARLVQVDVEQAALGAHRPIDLGVVGDVAGTAVDVHAELDKR---------GH-----
QRSREAPTGTRWNDVPYNDLSGDGR---------IDPRTLSRRLDEIL-
PAERMVSIDSGNFMGYPSAYLSVPDENGFCFTQAFQSIGLGLGTAIGAALARPDR----
LPVLGVGDGGFHMAVSELETAVRLRIPLVIVVYNDAAYGAEIHHFG------------
DADMTTVRFPDTDIAAIGRGFGCDGVTVRSVGDL-AAVKEWLGGPRDAPLVIDAKIADDGGSWWLAEAFRH--
-----------
>GEO247
-------MIDLDGTVTVAEYLGLRLRHAGVEHLFGVPGDFNLNLLDGLAFVEG--
LRWVGSPNELGAGYAADAYARRRGLSALFTTY-
GVGELSAINAVAGSAAEDSPVVHVVGSPRTTTVAGGALVHHTIADGDFRHFARAYAEVTVAQAMVTATDAG
AQIDRVLLAALTHRK-PVYLSIPQDLAL-----
HRIPAAPLREPLTPASDPAAVERFRTAVRDLLTPAVRPIMLVGQLVSRYGLSTLVTDMTTRSGIPV-
AAQLSAKGVIDESVEGNLGLYAGSMLDGPAASLIDSADVVLHLGTA-
LTAELTGFFTHRRPDARTVQLLSTAALVGTTRFDNV-
LFPDAMTTLAEVLTTFPAPARLAAPTTRAEPTGLAASITPPAPSAVDLTASTATDLTAPTAGDISEMSRVLTQDA
FWAGMQAWLPAGHALVADTGTSYWGAL--ALRLPGDTVFLGQPIWNSIGWALPAVLGQGLADPDR----R-
PVLVIGDGAAQMTIQELSTIVAAGLRPIILLLNNRGYTIERALQSPN-------AGYNDVA--DWNWRAV--
VAAFAGPDTDYHHAATGTELAKALTAA--SESNRPVFIEVELDAFDTPPLLRRLAERATAPS-------
>GEO244
------------MKQRIGAYLIDAIHRAGVDKIFGVPGDFNLAFLDDIISNPN--
VDWVGNTNELNASYAADGYARLNGLAALVTTF-
GVGELSAVNGIAGSYAERIPVIAITGAPTRAVEHAGKYVHHSLGEGTFDDYRKMFAHITVAQGYITPENATTEIP
RLINTAIAERR-PVHLHLPIDVAI-------
SEIEIPTPFEVTAAKDTDASTYIELLTSKLHQSKQPIIITGHEINSFHLHQELEDFVNQTQIPVAQLSL-
GKGAFNEENPYYMGIYDGKIAEDKIRDYVDNSDLILNIGAK-
LTDSATAGFSYQFNIDDVVMLNHHNIKIDDVTNDEISL-PSLLKQLSNISHT--------------N--------
NATFPAYHRPTSPDYTVGTEP-----------LTQQTYFKMMQNFLKPNDVIIADQGTSFFGAY--
DLALYKNNTFIGQPLWGSIGYTLPATLGSQLADKDR-----
RNLLLIGDGSLQLTVQAISTMIRQHIKPVLFVINNDGYTVERLIHGMY-------EPYNEIHM-WDYKALP--
AVFGGKNVEIHDVESSKDLQDTFNAIN-GHPDVMHFVEVKMSVEDAPKKLIDIAKAFSQQNK------
>GEO246
------------MKTVHSASYEILRRHGLTTVFGNPGSNELPFLKDFP--ED--
FRYILGLHEGAVVGMADGFALASGRPAFVNLHAAAGTGNGMGALTNAWYSHSPLVITAGQQVRSMIGVEAM
LANVDAGQLPKPLVKWSHEPAC------AQDVPRALSQAIQTASLPPRAPVYLSIPYDDWA----
QPAPAGVEHLAARQVSGAALPAPALLAELGERLSRSNPVLVLGPDVDGANANGLAVELAEKLRMPAWGAP
SASRCPFPTRHACFRGVLPAAIAGIS--
RLLDGHDLILVVGAPVFRYHQFAPGDYLPAGAELVQVTCDPGEAARAPMGD-ALVGDIALTLEALLEQVR-----
-------P-------SARPLPEALPRPPALAEEGGP-------------LRPETVF-
DVIDALAPRDAIFVKESTSTVTAFWQRVEMREPGSYFFPAA-GGLGFGLPAAVGAQLAQPRR-----
QVIGIIGDGSANYGITALWSAAQYRVPAVFIILKNGTYGALRWFAGVL--------EVPDAPGLDV--
PGLDFCAIARGYGVEALHAATREELEGALKHA--LAADRPVLIEVPTQTIEP---------------------
>GEO248

------------MYTVGNYLLDRLTELGIRDIFGVPGDYNLKFLDHVMTHKE--
LNWIGNANELNAAYAADGYARTKGIAALVTTF-
GVGELSAANGTAGSYAEKVPVVQIVGTPTTAVQNSHKLVHHTLGDGRFDHFEKMQTEINGAIAHLTADNALA
EIDRVLRIAVTE-RCPVYINLAIDVAE-----
VVAEKPLKPLMEESKKVEEETTLVLNKIEKALQDSKNPVVLIGNEIASFHLESALADFVKKFNLPVTVLPF-
GKGGFDEEDAHFIGVYTGAPTAESIKERVEKADLILIIGAK-
LTDSATAGFSYDFEDRQVISVGSDEVSFYGEIMKPVAF-AQFVNGLNSLNYL--------------G-------
YTGEIKQVERVADIEAKASN------------LTQNNFWKFVEKYLSNGDTLVAEQGTSFFGAS--
LVPLKSKMKFIGQPLWGSIGYTFPAMLGSQIANPAS-----
RHLLFIGDGSLQLTIQELGMTFREKLTPIVFVINNDGYTVEREIHGPN-------ELYNDIPM-
WDYQNLPYVFGGNKGNVATYKVTTEEELVAAMSQAR-
QDTTRLQWIEVVMGKQDSPDLLVQLGKVFAKQNS-----
>GEO179
------------MKTIHSAAYALLRRHGMTTIFGNPGSNELPFLKSFP--ED--
FQYVLGLHEGAVVGMADGYALASGKPAFVNLHAAAGTGNGMGALTNSWYSHSPLVITAGQQVRPMIGVEA
MLANVDATQLPKPLVKWSYEPAN------AQDVPRALSQAIHYANTTPKAPVYLSIPYDDWD----
QPSGPGVEHLIERDVQTAGTPDARQLQVLVQQVQDARNPVLVLGPDVDATLSNDHAVALADKLRMPVWIAPS
ASRCPFPTRHPSFRGVLPAAIAGIS--
KTLQGHDLIIVVGAPVFRYHQFAPGDYLPVGAQLLHITSDPLEATRAPMGH-ALVGDIRETLRVLAEEVVQ----
------Q--------SRPYPEALAAPECVTDEPHH-----------LHPETLF-
DVLDAVAPHDAIYVKESTSTTTAFWQRMNLRHPGSYYFPAA-GGLGFGLPAAVGVQLAQPQR-----
RVVALIGDGSANYGITALWTAAQYRIPVVFIILKNGTYGALRWFAGVL-------KAEDSPGLDV--
PGLDFCAIAKGYGVKAVHTDTRDSFEAALRTA--LDANEPTVIEVPTLTIQPH--------------------
>GEO240
-MSNAITKVQNANARRGGDVLLEVLESEGVEYVFGNPGTTELPFMDALLRKPS--
IQYVLALQEASAVAMADGYAQAAKKPGFLNLHTAGGLGHGMGNLLNAKCSQTPLVVTAGQQDSRHTTTDPL
LLG-DLVGMGKTFAKWSQEVTH------VDQLPVLVRRAFHDSDAAPKGSVFLSLPMDVME----
AMSAIGIGAPSTIDRNAVAGSLPLLASKLAAF--
TPGNVALIAGDEIYQSEAANEVVALAEMLAADVYGSTWPNRIPYPTAHPLWRGNLSTKATEIN--
RALSQYDAIFALGGKSLITILYTEGQAVPEQCKVFQLSADAGDLGRTYSSELSVVGDIKSSLKVLLPELEKATAN
HRRDYQRRFEKAINEFKLSKESLLGQVQEQQSATV-----------ITPLVAAFEAARAIGP-
DVAIVDEAIATSGSLRKSLNSHRADQYAFLRG-GGLGWGMPAAVGYSLGLGKA-----
PVVCFVGDGAAMYSPQALWTAAHEKLPVTFIVMNNTEYNVLKNFMRSQ-
ADYTSAQTDRFIAMDLVNPSVDYQALGASMGLETRKVIRAGDIAPAVEAA--LASGKPNVIEIIISKS------------
----------
>GEO195
MTSRSSFSPPSASEQRGADIFAEVLQCEGVRYIFGNPGTTELPLLDALTDITG--
IHYVLGLHEASVVAMADGYAQASGKPGFVNLHTAGGLGNAMGAILNAKMANTPLVVTAGQQDTRHGVTDP
LLHG-DLTGIARPNVKWAEEIHH------PEHIPMLLRRALQDCRTGPAGPVFLSLPIDTME----
RCTSVGAGEASRIERASVANMLHALATALAEV--
TAGHIALVAGEEVFTANASVEAVALAEALGAPVFGASWPGHIPFPTAHPQWQGTLPPKASDI-
RETLGPFDAVLILGGHSLISYPYSEGPAIPPHCRLFQLTGDGHQIGRVHETTLGLVGDLQLSLRALLPLLARKLQP
QNGAVARLRQVATLKRDARRTEAAERSAREFDASA-------------TTPFVAAFETIRAIGP-
DVPIVDEAPVTIPHVRACLDSASARQYLFTRS-AILGWGMPAAVGVSLGLDRS-----
PVVCLVGDGSAMYSPQALWTAAHERLPVTFVVFNNGEYNILKNYARAQ-
TNYRSARANRFIGLDISDPAIDFPALASSLGVPARRVERAGDIAIAVEDG--IRSGRPNLIDVLISSSS----------------
--------
>GEO241
--MNIAYETRENKVASGRECLLEILRDEGVTHVFGNPGTTELALIDALAGDDD--
FHFILGLQEAAVVGMADGYAQATGRPSFVNLHTTAGLGNGMGNLTNAFATNVPMVVTAGQQDIRHLAYDPL
LSG-DLVGLARATVKWAHEVRS------LQELPIILRRAFRDANTEPRGPVFVSLPMNIID-----
EIGTVSIPPRSTIVQAESGDISQLVRL--
LVESAGNLCLVVGDEVGRYGATEAAVRVAELLGAPVYGSPFHSNVPFPTDHPLWRFTLPPNTGEM--
RKVLGGYDRILLIGDRAFMSYTYSDELPLSPKTQLLQIAVDRHSLGRCHAVELGLYGDPLSLLAAVGDALSQER

FIG. 24 (Cont. 2)

AL---APSRDSRLAIARDWRASWEQDLKDECERLAPSRP-----------LYPLVAADAVLRGVPPG-
TVIVDECLATNKYVRQLYPVRKPGEYYYFRG-AGLGWGMPAAVGVSLGLERQ----
QRVVCLLGDGAAMYSPQALWSAAHESLPITFVVFNNSEYNILKNFMRSR--
PGYNAQSGRFVGMEINQPSIDFCALARSMGVDAVRLTEPDDITAYMIAA--GDREGPSLLEIPIAATAS-----------
------------
>GEO249
----------
MSSEKVLVGEYLFTRLLQLGIKSILGVPGDFNLALLDLIEKVGDETFRWVGNENELNGAYAADAYARVKGISAI
VTTF-
GVGELSALNGFAGAYSERIPVVHIVGVPNTKAQATRPLLHHTLGNGDFKVFQRMSSELSADVAFLDSGDSAGR
LIDNLLETCVRTSRPVYLAVPSDAGYFY--
TDASPLKTPLVFPVPENNKEIEHEVVSEILELIEKSKNPSILVDACVSRFHIQQETQDFIDATHFPTYVTPM-
GKTAINESSPYFDGVYIGSLTEPSIKERAESTDLLLIIGGL-
RSDFNSGTFTYATPASQTIEFHSDYTKIRSGVYEGISMKHLLPKLTAAIDKKSV------------Q--------
AKARPVHFEPPKAVAAEGYAEGT---------ITHKWFWPTFASFLRESDVVTTETGTSNFGIL--
DCIFPKGCQNLSQVLWGSIGWSVGAMFGATLGIKDSDAPHRRSILIVGDGSLHLTVQEISATIRNGLTPIIFVINN
KGYTIERLIHGLH-------AVYNDINTEWDYQNL--
LKGYGAKNSRSYNIHSEKELLDLFKDEEFGKADVIQLVEVHMPVLDAPRVLIEQAKLTASLNKQ-----
>KIVD_VLV
-------------MYTVGDYLLDRLHELGIEEIFGVPGDYNLQFLDQIISRKD--
MKWVGNANELNASYMADGYARTKKAAAFLTTF-
GVGELSAVNGLAGSYAENLPVVEIVGSPTSKVQNEGKFVHHTLADGDFKHFMKMHEPVTAARTLLTAENATV
EIDRVL-SALLKERKPVYINLPVDVAA-----
AKAEKPSLPLKKENSTSNTSDQEILNKIQESLKNAKKPIVITGHEIISFGLEKTVSQFISKTKLPITTLNF-
GKSSVDEALPSFLGIYNGKLSEPNLKEFVESADFILMLGVK-
LTDSSTGAFTHHLNENKMISLNIDEGKIFNESIQNFDFESLISSLLDLSEIE--------------Y--------
KGKYIDKKQEDFVPSNAL--------------LSQDRLWQAVENLTQSNETIVAEQGTSFFGAS--
SIFLKPKSHFIGQPLWVSIGYTFPAALGSQIADKES-----
RHLLFIGDGSLQLTVQELGLAIREKINPICFIINNDGYTVEREIHGPN-------QSYNDIPM-
WNYSKLPESFGATEERVVSKIVRTENEFVSVMKEAQ-ADPNRMYWIELILAKEDAPKVLKKLGKLVAEQNKS-
----

DISCOVERY OF ENZYMES FROM THE ALPHA-KETO ACID DECARBOXYLASE FAMILY

CROSS-REFERENCES TO RELATED APPLICATIONS

This application is a U.S. National Phase of PCT/US2016/049210, filed Aug. 29, 2016, which claims the benefit of priority to U.S. Provisional Application No. 62/211,439, filed Aug. 28, 2015, the contents of which are hereby incorporated in the entirety for all purposes.

BACKGROUND OF THE INVENTION

A central goal of the bioeconomy is to reduce our dependence on petroleum through next-generation biomanufacturing. The USDA projects the industrial production of bio-based specialty chemicals to reach ~$340 billion USD by 2025, replacing half of our needs for these products from petroleum. To accomplish this ambitious goal, non-natural biochemical pathways are needed. An example of one such pathway is the "synthetic recursive+1" carbon elongation pathway that has been developed to produce a variety of alcohol products in E. coli. The primary product from the current pathway is 1-butanol, with longer chain alcohols (e.g., pentanol, hexanol, heptanol, and octanol) being either minor products of the pathway, or not produced at all. Yet, there is significant interest in producing long chain alcohols given their use as specialty chemicals, as well as their greater energy density when used as liquid fuels or fuel additives. The present invention fulfills these and other needs.

BRIEF SUMMARY OF THE INVENTION

In one aspect, the present invention provides an expression cassette comprising a heterologous promoter operably linked to a nucleic acid encoding an enzyme comprising 2-ketoacid decarboxylase activity, wherein the enzyme: comprises a 3-layer alpha-beta-alpha sandwich; comprises a thiamine pyrophosphate (TPP) binding pocket; has a TM align score of at least about 0.5 (e.g., from about 0.5 to about 1.0, from about 0.5 to about 0.8, or from about 0.5 to about 0.9) as compared against PDB ID:2VBG (SEQ ID NO:40); and comprises at least about a 10-fold, 25-fold, 50-fold, or 100-fold (e.g., from about 10-fold to about 100,000-fold; from about 10-fold to about 10,000 fold; from about 10-fold to about 200-fold; from about 10-fold to about 100-fold; from about 25-fold to about 100,000-fold; from about 25-fold to about 10,000 fold; from about 25-fold to about 200-fold; from about 25-fold to about 100-fold; from about 50-fold to about 100,000-fold; from about 50-fold to about 10,000 fold; from about 50-fold to about 200-fold; or from about 50-fold to about 100-fold) greater catalytic efficiency for C8 2-ketoacid substrates as compared to C3 or isoC5 2-ketoacid substrates, wherein the catalytic efficiency is measured by kcat/Km.

In some embodiments, the enzyme comprising 2-ketoacid decarboxylase activity has a TM align score of at least 0.5 (e.g., from about 0.5 to about 0.8, from about 0.5 to about 0.9, or from about 0.5 to about 1.0), 0.6 (e.g., from about 0.6 to about 0.8, from about 0.6 to about 0.9, or from about 0.6 to about 1.0), 0.7 (e.g., from about 0.7 to about 0.8, from about 0.7 to about 0.9, or from about 0.7 to about 1.0), 0.8 (e.g., from about 0.8 to about 0.9, or from about 0.8 to about 1.0), or 0.9 (e.g., from about 0.9 to about 1.0) as compared against PDB ID:2VBG. In some embodiments, the substrate binding pocket of the enzyme has a solvent accessible surface area of, of about, of at least, or of at least about 5,000; 5,500; 6,000; 6,500; 7,000; 7,500; 8,000; or 8,500; 9,000; 9,500; or 10,000 Å$^2$ (e.g., from about 5,000 to about 10,000 Å$^2$; from about 5,500 to about 9,500 Å$^2$; from about 6,000 to about 9,000 Å$^2$; from about 6,500 to about 8,500 Å$^2$; from about 7,000 to about 8,000 Å$^2$; or from about 7,500 to about 8,000 Å$^2$).

In some embodiments, the enzyme comprising 2-ketoacid decarboxylase activity comprises an amino acid sequence that is, is at least, or is at least about 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, or 89% identical to SEQ ID NO:1. In some embodiments, the enzyme comprising 2-ketoacid decarboxylase activity comprises an amino acid sequence that is less than, or less than about, 90%, 95%, or 99% identical to SEQ ID NO:1. In some embodiments, the enzyme comprising 2-ketoacid decarboxylase activity comprises an amino acid sequence that is from about 14% to about 89% identical to SEQ ID NO:1; from about 20% to about 89% identical to SEQ ID NO:1; from about 25% to about 89% identical to SEQ ID NO:1; from about 30% to about 89% identical to SEQ ID NO:1; from about 35% to about 89% identical to SEQ ID NO:1; from about 40% to about 89% identical to SEQ ID NO:1; from about 45% to about 89% identical to SEQ ID NO:1; from about 50% to about 89% identical to SEQ ID NO:1; from about 55% to about 89% identical to SEQ ID NO:1; from about 60% to about 89% identical to SEQ ID NO:1; from about 65% to about 89% identical to SEQ ID NO:1; from about 70% to about 89% identical to SEQ ID NO:1; from about 75% to about 89% identical to SEQ ID NO:1; or from about 80% to about 89% identical to SEQ ID NO:1.

In some embodiments, the enzyme comprising 2-ketoacid decarboxylase activity comprises an amino acid sequence that contains a mutation of a native sequence wherein the mutation is in an amino acid residue within a 2-ketoacid decarboxylase active site or in an amino acid residue having a Cα within 8 Å (e.g., having a Cα atom within about 1, 1.5, 2, 2.5, 3, 3.5, 4, 4.5, 5, 5.5, 6, 6.5, 7, or 7.5 Å) of a 2-ketoacid decarboxylase active site, wherein the 2-ketoacid decarboxylase active site comprises the amino acids corresponding to amino acid positions 23-27, 50, 51, 56, 75, 76, 79, 82, 113, 114, 287, 352, 373-377, 379, 394, 396-399, 424-428, 430, 450-458, 461, and 532 of PDB ID:2VBG.

In some embodiments, the enzyme comprising 2-ketoacid decarboxylase activity comprises an amino acid sequence that contains a mutation of a native sequence wherein the mutation is in an amino acid residue within a 2-ketoacid decarboxylase active site or is in an amino acid residue within 8 Å (e.g., having a non-hydrogen atom within about 1, 1.5, 2, 2.5, 3, 3.5, 4, 4.5, 5, 5.5, 6, 6.5, 7, or 7.5 Å) of a 2-ketoacid decarboxylase active site, wherein the 2-ketoacid decarboxylase active site comprises the amino acids corresponding to amino acid positions 23-27, 50, 51, 56, 71, 75, 76, 79, 82, 112, 114, 287, 356, 373-377, 379, 394, 396-399, 423-428, 430, 450-458, 461, and 535 of SEQ ID NO:1.

In some embodiments, the enzyme comprising 2-ketoacid decarboxylase activity comprises an amino acid sequence that is at least 90%, 95%, or 99% identical to SEQ ID NO:1

(e.g., from 90% to about 99% or more identical to SEQ ID NO:1, or from 95% to about 99% or more identical to SEQ ID NO:1). In some embodiments, the enzyme comprising 2-ketoacid decarboxylase activity comprises an amino acid sequence that contains 1, 2, 3, 4, or 5 mutations (e.g., substitutions) as compared to SEQ ID NO:1, 2, or 3.

In some embodiments, the enzyme comprising 2-ketoacid decarboxylase activity comprises an amino acid sequence that contains 1, 2, or 3 mutations (e.g., substitutions) in amino acid residues corresponding to a residue selected from the group consisting of G402, M538, and F542 of SEQ ID NO:1 (SEQ ID NO:18).

In some embodiments, the mutation in an amino acid residue corresponding to a residue selected from the group consisting of G402, M538, and F542 of SEQ ID NO:1 is from a (e.g., native) sequence to a residue selected from the group consisting of Val, Leu, Ile, Met, Phe, His, Gly, Ala, Thr, Tyr, and Trp (SEQ ID NO:18).

In some embodiments, the mutation corresponds to, or is, a mutation selected from the group consisting of G402V, M538L, and F542V of SEQ ID NO:1 (SEQ ID NO:18).

In some embodiments, the enzyme comprising 2-ketoacid decarboxylase activity comprises two mutations (e.g., substitutions) in amino acid residues corresponding to residues selected from the group consisting of G402, M538, and F542 of SEQ ID NO:1. In some embodiments, the enzyme comprising 2-ketoacid decarboxylase activity comprises mutations (e.g., substitutions) corresponding to G402V, M538L, and F542V of SEQ ID NO:1 or comprises SEQ ID NO:3.

In some embodiments, the enzyme comprising 2-ketoacid decarboxylase activity comprises an amino acid sequence at least 90% or 99% identical (e.g., from about 90% to about 99%), or identical, to SEQ ID NO:2.

In some embodiments, the enzyme comprising 2-ketoacid decarboxylase activity comprises an amino acid sequence that contains a mutation, wherein the mutation is in an amino acid residue of a 2-ketoacid decarboxylase active site residue of SEQ ID NO:2 or in an amino acid residue having a Cα within 8 Å (e.g., having a non-hydrogen atom within about 1, 1.5, 2, 2.5, 3, 3.5, 4, 4.5, 5, 5.5, 6, 6.5, 7, or 7.5 Å) of the 2-ketoacid decarboxylase active site, wherein the 2-ketoacid decarboxylase active site comprises the amino acids corresponding to amino acid positions 23-27, 48, 49, 54, 71, 74, 75, 78, 81, 112, 113, 286, 356, 376-380, 382, 399, 401-404, 427-432, 434, 454-462, 465, and 535 of SEQ ID NO:2.

In some embodiments, the enzyme comprising 2-ketoacid decarboxylase activity interacts with a C8 2-ketoacid substrate with a calculated interaction energy of less than −5, −5.5, −6, −6.5, −7, −7.5, −8, −8.5, −9, −9.5, −10, −10.3, −10.4, −10.5, −10.6, −10.7, −10.8, −10.9, −11, −11.5, −12, −12.5, −13, −13.5, −14, −14.5, −15, −15.5, −16, −16.5, −17, −17.5, −18, −18.5, −19, −19.5, or −20 rosetta energy units. In some embodiments, the enzyme comprising 2-ketoacid decarboxylase activity interacts with a C8 2-ketoacid substrate with a calculated interaction energy of from about −20 to about −5 rosetta energy units, from about −15 to about −8 rosetta energy units; or from about −11 to about −9 rosetta energy units.

In another aspect, the present invention provides a modified enzyme comprising 2-ketoacid decarboxylase activity, wherein the enzyme comprises: a 3-layer alpha-beta-alpha sandwich; thiamine pyrophosphate; and at least a 10-fold, 25-fold, 50-fold, or 100-fold (e.g., from about 10-fold to about 100,000-fold; from about 10-fold to about 10,000 fold; from about 10-fold to about 200-fold; from about 10-fold to about 100-fold; from about 25-fold to about 100,000-fold; from about 25-fold to about 10,000 fold; from about 25-fold to about 200-fold; from about 25-fold to about 100-fold; from about 50-fold to about 100,000-fold; from about 50-fold to about 10,000 fold; from about 50-fold to about 200-fold; or from about 50-fold to about 100-fold) greater catalytic efficiency for C8 2-ketoacid substrates as compared to C3 or isoC5 2-ketoacid substrates, wherein the catalytic efficiency is measured by kcat/Km, wherein the modification comprises a mutation (e.g., substitution) in the primary amino acid sequence of SEQ ID NO:1 or SEQ ID NO:2.

In some embodiments, the enzyme has a TM align score against PDB ID:2VBG of at least 0.5 (e.g., from about 0.5 to about 0.8, from about 0.5 to about 0.9, or from about 0.5 to about 1.0), 0.6 (e.g., from about 0.6 to about 0.8, from about 0.6 to about 0.9, or from about 0.6 to about 1.0), 0.7 (e.g., from about 0.7 to about 0.8, from about 0.7 to about 0.9, or from about 0.7 to about 1.0), 0.8 (e.g., from about 0.8 to about 0.9, or from about 0.8 to about 1.0), or 0.9 (e.g., from about 0.9 to about 1.0). In some embodiments, the enzyme has a Cα root mean squared deviation of less than 1 Å (e.g., from about 0.1 Å to about 1 Å, from about 0.2 Å to about 1 Å, from about 0.3 Å to about 1 Å, from about 0.4 Å to about 1 Å, or from about 0.5 Å to about 1 Å) over at least 100 (e.g., from about 100 to about 200 or more) structurally aligned residues as compared against PDB ID:2VBG.

In some embodiments, the modification comprises a mutation (e.g., substitution) in an amino acid residue, wherein the amino acid residue is within a 2-ketoacid decarboxylase active site or within 8 Å (e.g., having a Cα atom within about 1, 1.5, 2, 2.5, 3, 3.5, 4, 4.5, 5, 5.5, 6, 6.5, 7, or 7.5 Å) of a 2-ketoacid decarboxylase active site, wherein the 2-ketoacid decarboxylase active site comprises the amino acids corresponding to amino acid positions 23-27, 50, 51, 56, 71, 75, 76, 79, 82, 112, 114, 287, 356, 373-377, 379, 394, 396-399, 423-428, 430, 450-458, 461, and 535 of SEQ ID NO:1.

In some embodiments, the modification comprises a mutation (e.g., substitution) in an amino acid residue corresponding to a residue selected from the group consisting of G402, M538, and F542 of SEQ ID NO:1. In some embodiments, the mutation (e.g., substitution) in an amino acid residue corresponding to a residue selected from the group consisting of G402, M538, and F542 of SEQ ID NO:1 is a mutation from a (e.g., native) sequence to a residue selected from the group consisting of Val, Leu, Ile, Met, Phe, His, Gly, Ala, Thr, Tyr, and Trp.

In some embodiments, the modification comprises two mutations (e.g., substitutions) in amino acid residues corresponding to residues selected from the group consisting of G402, M538, and F542 of SEQ ID NO:1. In some embodiments, the modification comprises one or two mutations (e.g., substitutions) corresponding to the mutations selected from the group consisting of G402V, M538L, and F542V of SEQ ID NO:1. In some embodiments, the modification comprises mutations (e.g., substitutions) corresponding to G402V, M538L, and F542V of SEQ ID NO:1. In some embodiments, the ratio of kcat/Km against C8 2-ketoacid substrates over the kcat/Km against isoC5 2-ketoacid substrates is at least 10-fold, 25-fold, 50-fold, or 100-fold (e.g., from about 10-fold to about 100,000-fold; from about 10-fold to about 10,000 fold; from about 10-fold to about 200-fold; from about 10-fold to about 100-fold; from about 10-fold to about 50-fold; from about 25-fold to about 100,000-fold; from about 25-fold to about 10,000 fold; from about 25-fold to about 200-fold; from about 25-fold to about 100-fold; from about 25-fold to about 50-fold; from about 50-fold to about 100,000-fold; from about 50-fold to about 10,000 fold; from about 50-fold to about 200-fold; or from about 50-fold to about 100-fold) greater than the native enzyme. In some embodiments, the solvent accessible surface area of the substrate binding pocket is, is about, is at least, or is at least about 5,000; 5,500; 6,000; 6,500; 7,000; 7,500; 8,000; 8,500; 9,000; 9,500; or 10,000 Å² (e.g., from about 5,000 to about 10,000 Å²; from about 5,500 to about 9,500 Å²; from about 6,000 to about 9,000 Å²; from about 6,500 to about 8,500 Å²; from about 7,000 to about 8,000 Å²; or from about 7,500 to about 8,000 Å²).

In another aspect, the present invention provides a host cell comprising any of the foregoing expression cassettes or modified enzymes, wherein the host cell produces long chain (≥C5) alcohols at a concentration of at least 5 mg/L, 25 mg/L, 50 mg/L, 100 mg/L, 200 mg/L, 250 mg/L, 300 mg/L, 400 mg/L, or 500 mg/L (e.g., from about 5 mg/L to about 300, 400, 500, 600, 700, 800, or more mg/L, from about 10 mg/L to about 500 mg/L, from about 10 mg/L to about 400 mg/L, from about 10 mg/L to about 300 mg/L, from about 25 mg/L to about 500 mg/L, from about 25 mg/L to about 400 mg/L, from about 25 mg/L to about 300 mg/L, from about 50 mg/L to about 500 mg/L, from about 50 mg/L to about 400 mg/L, from about 50 mg/L to about 300 mg/L; from about 100 mg/L to about 500 mg/L, from about 100 mg/L to about 400 mg/L, or from about 100 mg/L to about 300 mg/L).

In some embodiments, the host cell produces heptanol as the major alcohol product or second-most major alcohol product. In some embodiments, the host cell produces hexanol as the major alcohol product or second-most major alcohol product. In some embodiments, the host cell produces at least 200 mg/L (e.g., from about 200 to about 500, from about 200 to about 400, from about 250 to about 450, from about 250 to about 350, or from about 300 to about 350 mg/L) heptanol or hexanol, or a combination thereof. In some embodiments, the host cell produces octanol. In some embodiments, the host cell does not produce ethanol or propanol, or produces at least 10-fold (e.g., from 10-fold to 100-fold, or more, or from 10-fold to 50-fold, or from 10-fold to 20-fold) more long chain alcohols (≥C5) as compared to ethanol and/or propanol.

BRIEF DESCRIPTION OF THE DRAWINGS

FIG. 1: Depicts an illustration of the synthetic recursive+1 pathway. This pathway employs enzymes LeuABCD from leucine biosynthesis for carbon chain elongation of 2-ketoacids. The enzyme ketoisovalerate decarboxylase (KIVD) performs the decarboxylation of 2-ketoacids and diverts carbon out from the +1 iterative cycle.

FIG. 2: Depicts an illustration of a computationally directed genomic enzyme mining pipeline. (Left) GEOs are identified based on sequence homology to KIVD. Bioinformatics filters are used to identify a set of protein sequences from genomic databases that are predicted to be KIVD homologs and likely to be decarboxylases. Once identified, homology models are built to obtain a predicted ternary structure of each GEO. Ligand docking and design simulations are subsequently run in the presence of the target ligand (e.g., C8) to evaluate the potential protein-ligand interface energy. (Middle) A phylogenetic tree for the 239 GEOs is depicted with a bar chart above each sequence. The bar height indicates the predicted protein-ligand interface energy, the higher the bar the lower the energy. Bar height is scaled linearly relative to the lowest protein-ligand interface energy. 10 GEOs are selected for experimental characterization. (Right) The pairwise sequence identity of all 239 GEOs to each other has a mode of 20%, indicating the high level of sequence diversity within this set of sequences.

FIG. 3: Depicts an illustration of reaction specificities for various 2 ketoacid decarboxylases. (a) Ketoisovalerate decarboxylase (KIVD) utilizes various ketoacids as substrates to produce the corresponding aldehyde. (b) Ketoacids used for in vitro kinetic constants in addition to 2-ketoisovaleric acid.

FIG. 4: Depicts catalytic efficiency and specificity of characterized ketoacid decarboxylases. Specificity factor is calculated as $$\frac{\log C8}{\log C5} + \frac{\log C8}{\log C3}$$

Figure 20:
Figure 20:
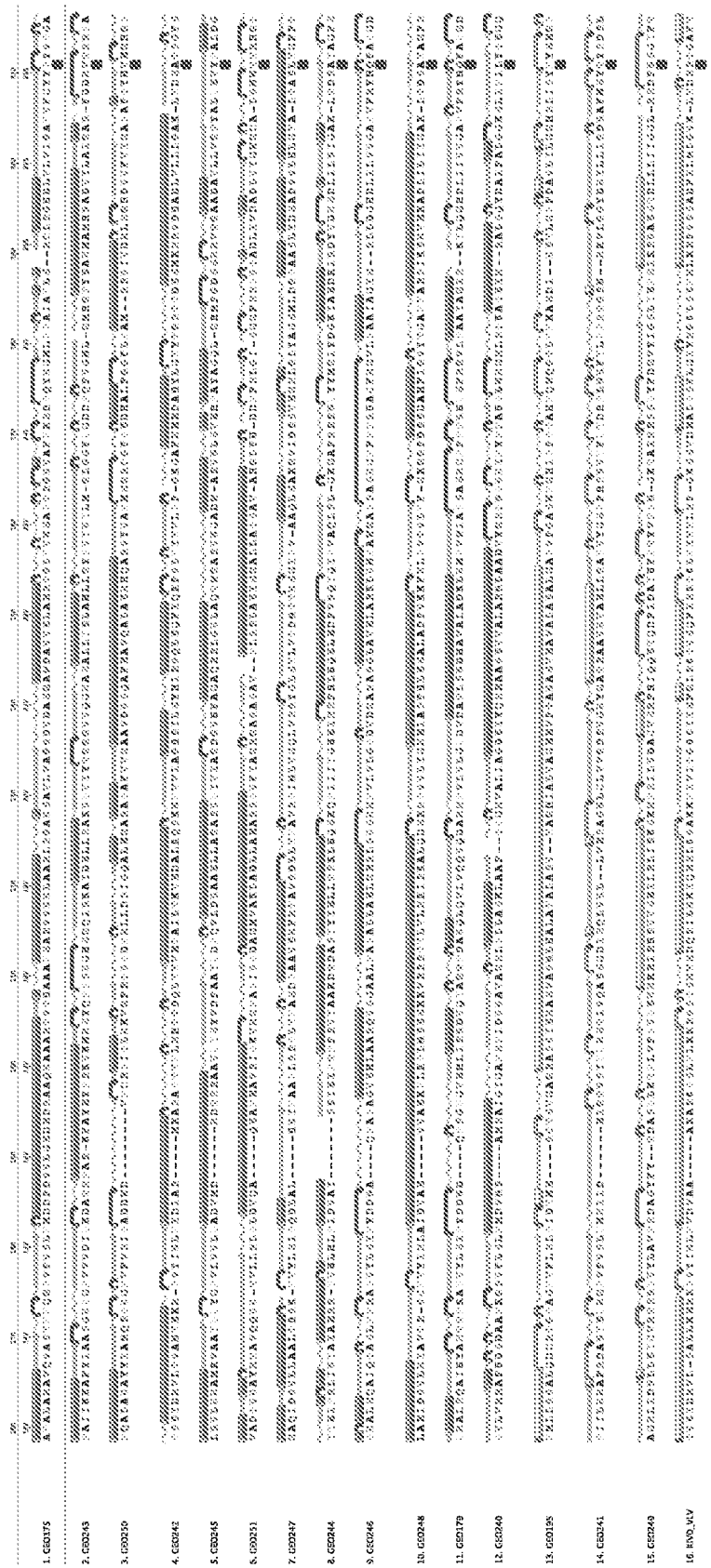
Figure 20:
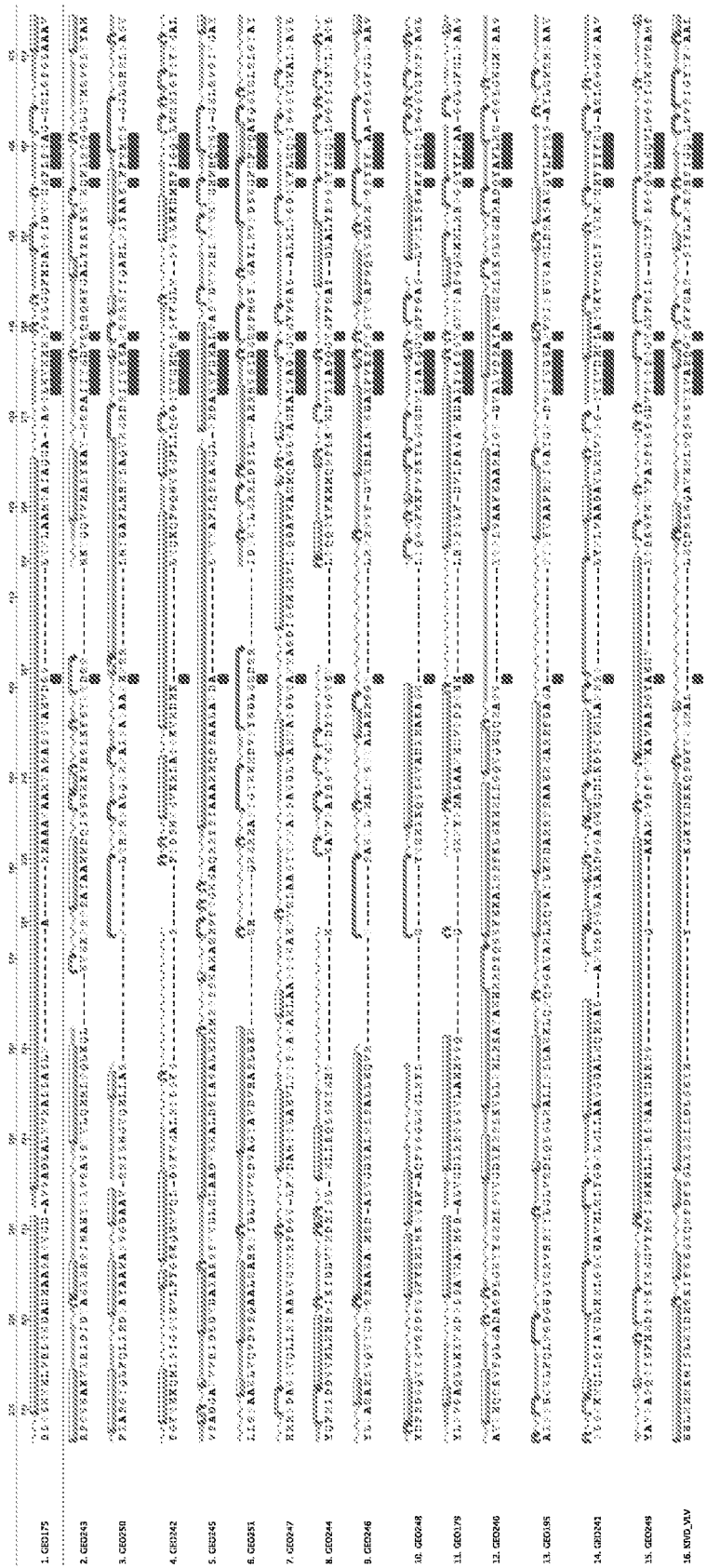
Figure 20:

where the log scaled catalytic efficiencies for C8 relative to C5 and C3 are compared. The three active GEOs and the naively selected set of decarboxylases are represented as dots and diamonds, respectively. Native KIVD and KIVD_VLV are depicted as a square and triangle, respectively. The genomic mining method and computational active site redesign approach both produced enzymes with enhanced specificity relative to native KIVD.

FIG. 5: Depicts a molecular model of a C8 intermediate docked into KIVD (a, c) and GEO 175 (b, d). Cross sections of the space filled active site are represented in a and b where the C8 keto acid and TPP ligand are depicted. A detailed view of the amino acids within the active site are illustrated in c and d. Residues within 5 Å of C8 ligand are shown in sticks and their corresponding C-alpha are shown in spheres. Figure was generated using PyMol v1.7.4.

FIG. 6: Depicts results of kinetic characterization of GEO 175 and GEO 175 L376T_T240S. Kinetic constants were measured as described herein. The substrate 2-ketooctanoate carbon chain numbering referred to in the text is numbered in white. According to the molecular model of GEO 175, the double mutation L376T_T240S is predicted to recede the pocket by 1.4 Å and remove interactions between the binding pocket and carbon 8 of the ketoacid alkyl chain. This mutant was observed to decrease catalytic efficiency on C8, but has a negligible effect on shorter chain substrates.

FIG. 7: Depicts an illustration of a screening process for identifying an engineered KIVD with altered substrate specificity. The design process can start with identifying active site residues of KIVD (depicted as spheres in panel on left). These amino acids were allowed to either remain native or sample any of eleven relatively hydrophobic amino acids. A total of 10,000 design simulations were run and the amino acids identified in the 50 lowest energy designs were used to guide construction of a small library of roughly 400 KIVD mutants from the original combinatorial space of 1011 possible active site mutations. 1200 clonal isolates were screened for activity and specificity. The KIVD_VLV (SEQ ID NO:3) mutant was selected and subsequently purified for in vitro kinetic constant characterization.

FIG. 8: Depicts results of in vivo alcohol production of the synthetic recursive+1 pathway with native KIVD, KIVD_VLV, and GEO 175. Cells were incubated for forty hours in microaerobic conditions in a defined media as described in materials and methods. Each assay was performed in triplicate and titers reported if all three samples had observed product production above the limit of quantitation (5 mg/L).

FIG. 9: Depicts toxicity as a function of alcohol chain length. The optical density of engineered E. coli strains after a 7-hour growth was measured as a function of the alcohol concentration added to growth media at the beginning of incubation.

FIG. 10: Depicts an overlay of active sites between GEO 175 and BFD. Residues that are different between the proteins are shown in sticks and their corresponding alpha carbons are shown in spheres.

FIG. 11: Depicts a screening process for identifying engineered KIVD with altered substrate specificity. Pertinent screening results and candidate mutants are shown (graphs) which contributed directly to finding KIVD_VLV. Colorimetric assays (graphs) measured approximate enzyme activity of screened mutants for ketoisovalerate (IsoC5), 2-ketobutyrate (C4), 2-ketovalerate (C5), 2-ketohexanoate (C6), and 2-ketooctanoate (C8). Higher activity is shown by larger downwards slope; greater specificity relative to KIVD was observed in mutants with reduced activity for IsoC5, C4, and C5, and only slightly affected or greater activity for C6 and C8. First round high-throughput colorimetric screening of single mutants identified candidates such as G402V and M538L/F542V. Mutations from each region that showed potential in altering the specificity of KIVD were combined to produce multi-region mutants through site-directed mutagenesis using the plasmids of KIVD single region mutants as templates. These KIVD multi-region mutants, such as G402V M538L F542V (KIVD_VLV) were then screened a second time with the colorimetic assays. Enzyme kinetics was then measured for mutant KIVD_VLV.

FIG. 12: Depicts results of Michaelis-Menten curve fitting of tested enzymes with C8 substrate.

FIG. 13: Depicts results of Michaelis-Menton curve fitting of tested enzymes with C5 substrate.

FIG. 14: Depicts results of Michaelis-Menten curve fitting of tested enzymes with C3 substrate.

FIG. 15: Depicts results of Michaelis-Menten curve fitting of tested enzymes with isoC5 substrate.

FIG. 16: Depicts pdb codes and accession numbers of GEOs modeled as listed on the phylogenetic tree depicted in FIG. 2. Sequences were obtained from homologous sequence search in the non-redundant database using HMMER3.

FIG. 17: Depicts protein sequences of various 2-ketoacid decarboxylases (SEQ ID NOS:20-34). Protein Sequence 3FZN is SEQ ID NO: 20. Protein sequence 2VBI is SEQ ID NO: 21. Protein sequence 1ZPD is SEQ ID NO: 22. Protein sequence ZP_08570611 is SEQ ID NO: 23. Protein sequence YP_831380 is SEQ ID NO: 24. Protein sequence ZP_06547677 is SEQ ID NO: 25. Protein sequence 1OVM_P23234 is SEQ ID NO: 26. Protein sequence ZP_06418208 is SEQ ID NO: 27. Protein sequence ZP_07290467 is SEQ ID NO: 28. Protein sequence 2VBG is SEQ ID NO: 29. Protein sequence CAK95977 is SEQ ID NO: 30. Protein sequence ZP_07282849 is SEQ ID NO: 31. Protein sequence ZP_06846103 is SEQ ID NO: 32. Protein sequence ZP_04996569 is SEQ ID NO: 33. Protein sequence YP_381143 is SEQ ID NO: 34.

FIG. 18: Depicts the native sequence and various engineered substitutions at various amino acid positions of KIVD used to probe for altered specificity for long chain 2-ketoacids. Amino acids in parentheses denote potential mutations due to degenerate codons used for mutagenesis. Library 1 is SEQ ID NO:35; library 2 is SEQ ID NO:36; library 3 is SEQ ID NO:37; library 4 is SEQ ID NO:38; library 5 is SEQ ID NO:39.

FIG. 19: Depicts activity data for various GEOs tested against C3, C5, C8, and isoC5 substrates and calculated Rosetta energy values for bound TPP-C8 ligand.

FIG. 20: Depicts results of a structural alignment of GEOs and KIVD (GEO175=SEQ ID NO:2, GEO243=SEQ ID NO:5, GEO 250=SEQ ID NO:6, GEO 242=SEQ ID NO:7, GEO 245=SEQ ID NO:8, GEO 251=SEQ ID NO:9, GEO 247=SEQ ID NO:10, GEO 244=SEQ ID NO:11, GEO 246=SEQ ID NO:12, GEO 248=SEQ ID NO:13, GEO 179=SEQ ID NO:14, GEO 240=SEQ ID NO:15, GEO 195=SEQ ID NO:16, GEO 241=SEQ ID NO:17, GEO 249=SEQ ID NO:4, KIVD_VLV=SEQ ID NO:3). Active site residues are denoted with a black box under the residue letter.

FIG. 21: Depicts a profile of active site residues and preferred amino acid substitutions at such residues for 2-ketoacid decarboxylases described herein. A 5 Å cut-off was utilized to define active-site residues. The active site residues are defined as those protein residues found in the model to have any non-hydrogen atoms within 5 Å of any of the atoms in the TPP-C8 ligand. The model of KIVD_VLV was generated by threading the KIVD sequence onto the crystal structure of 2VBG (88% identical in sequence to KIVD), making the three mutations, and subsequently docking in the model of the C8 substrate.

FIG. 22: Depicts a profile of active site residues and preferred amino acid substitutions at such residues for 2-ketoacid decarboxylases described herein. An 8 Å cut-off was utilized to define active-site residues. The active site residues are defined as those protein residues found in the model to have any non-hydrogen atoms within 8 Å of any of the atoms in the TPP-C8 ligand. The model of KIVD_VLV was generated by threading the KIVD sequence onto the crystal structure of 2VBG (88% identical in sequence to KIVD), making the three mutations, and subsequently docking in the model of the C8 substrate.

Figure 23:
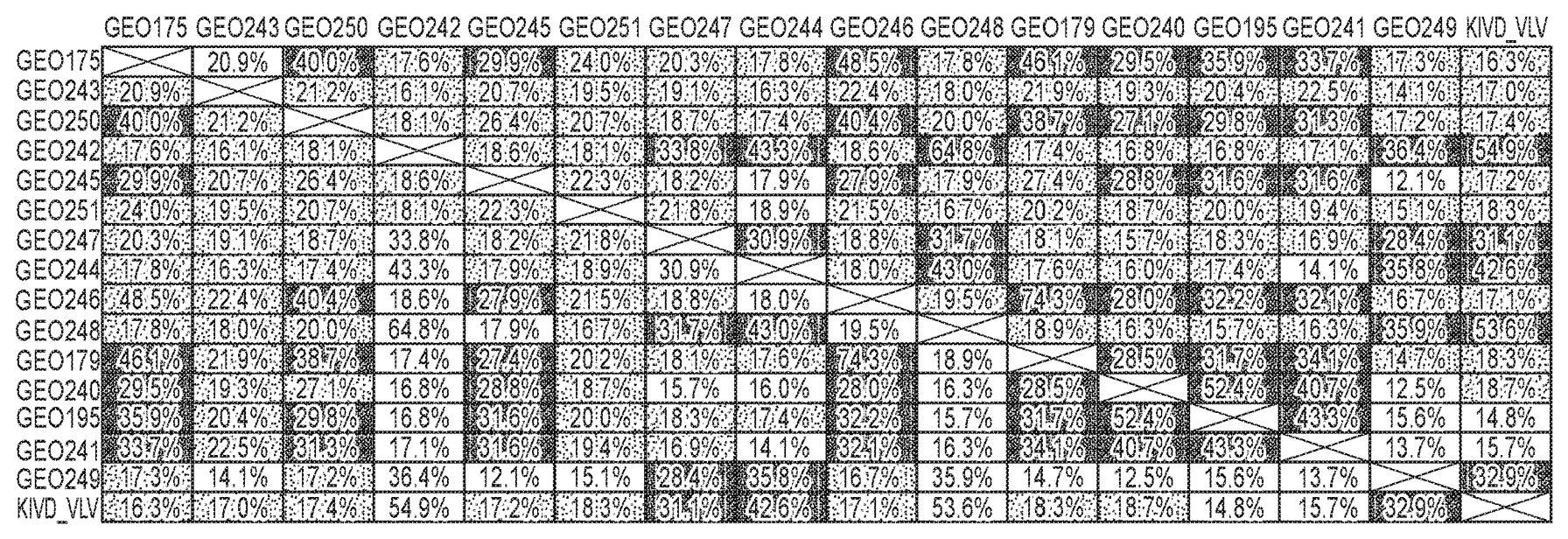

FIG. 23: Depicts pairwise identities for 2-ketoacid decarboxylases described herein.

FIG. 24: Depicts the contents of a sequence alignment file in aln format (GEO175=SEQ ID NO:2, GEO243=SEQ ID NO:5, GEO 250=SEQ ID NO:6, GEO 242=SEQ ID NO:7, GEO 245=SEQ ID NO:8, GEO 251=SEQ ID NO:9, GEO 247=SEQ ID NO:10, GEO 244=SEQ ID NO:11, GEO 246=SEQ ID NO:12, GEO 248=SEQ ID NO:13, GEO 179=SEQ ID NO:14, GEO 240=SEQ ID NO:15, GEO 195=SEQ ID NO:16, GEO 241=SEQ ID NO:17, GEO 249=SEQ ID NO:4, KIVD_VLV=SEQ ID NO:3).

DEFINITIONS

As used in this specification and the appended claims, the singular forms "a," "an," and "the" include plural reference unless the context clearly dictates otherwise.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. In some cases, the promoter is heterologous to the polynucleotide to be transcribed. In some cases, the expression cassette is heterologous to the host cell in which it resides.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "heterologous" as used in the context of describing the relative location of two elements, refers to the two elements such as nucleic acids (e.g., promoter and protein encoding sequence), a nucleic acid and a host cell, a protein (e.g., a 2-ketoacid decarboxylase, or portion thereof) and a host cell or reaction mixture, or a protein and a ligand that are not naturally found in the same relative positions. Thus, a "heterologous promoter" of a gene refers to a promoter that is not naturally operably linked to that gene. Similarly a host cell containing a heterologous expression cassette can refer to an expression cassette that is not naturally found in that host cell.

A "3-layer alpha-beta-alpha sandwich" refers to the 3-layer (aba) Sandwich architecture according to the CATH classification (version 4.0.0). Proteins containing such architecture have a Rossmann fold topology. For enzymes that have not been characterized by X-ray crystallography, NMR spectroscopy, or other experimental means, the presence or absence of a 2-layer alpha beta alpha sandwich can be assessed by homology modeling. Exemplary methods of homology modeling can include the use of one or more of the following programs, program codes, scripts, and/or parameters, e.g. in their default settings: RosettaCM, SWISS-MODEL, MODELLER, 3D-JIGSAW, ModPipe, Fugue, HHPred, i-Tasser, IntFOLD, M4T, ModWeb, Phyre2, RaptorX, Robetta, HHsuite, and the like, such as derivative works thereof.

A "thiamine pyrophosphate (TPP) binding pocket" refers to a binding pocket of a enzyme that productively binds TPP, such that the TPP bound by the enzyme can perform a ketoacid decarboxylation reaction. The presence of a TPP binding pocket can be detected by detecting bound TPP, or a radical intermediate thereof (e.g., via mass spectrometry, electron paramagnetic resonance (EPR) spectroscopy, or the like). The presence of a TPP binding pocket can also be inferred on the basis of detection of TPP mediated catalysis by the enzyme. In some cases, the presence of a TPP binding pocket can be determined from an experimentally determined structure of the enzyme (e.g., determined by X-ray crystallography). In some cases, the presence of a TPP binding pocket can be determined by homology modeling using any of the homology modeling methods described herein. In some cases, the presence of a TPP binding pocket can be inferred from the presence of sequence data indicative of a TPP binding domain. For example, a comparison of a candidate sequence to the Pfam database (e.g., Pfam 28.0) can reveal the presence or absence of a TPP binding pocket.

A "TM align score" refers to a normalized structural similarity score comparing two 3-dimensional protein structures (e.g., experimentally determined or homology model structures) calculated by version 2012/05/07 of the TM-align algorithm (TMalign.f). See, Y. Zhang & J. Skolnick, Nucleic Acids Research, 33: 2302-2309 (2005); Y. Zhang & J. Skolnick, Proteins, 57: 702-710 (2004); and J. Xu & Y. Zhang, Bioinformatics, 26, 889-895 (2010). Where one or both structures contain multiple chains of substantially the same structure (e.g., due to non-crystallographic symmetry or due to the availability of an ensemble of homology models), the TM align score refers to the lowest score between the one or more chains of a first structure and the one or more chains of a second structure.

"Solvent accessible surface area" or "SASA" in reference to a substrate binding pocket of an enzyme described or claimed herein refers to a SASA calculated using RosettaScripts with Rosetta version c2bf8f674e7b416b5b756630d7ccd5d64c57512c 2015-05-04 14:47:46-0700 from git@github.com:RosettaCommons/main.git. The SASA can be calculated from a structure file (PDB) with a bound ligand. The structure file can be an experimentally determined structure or a structure determined by any one or more of the homology modeling methods described herein.

As used herein, "2-ketoacid active site," in the context of the claims can refer to amino acid residues corresponding to amino acid positions: (i) 23-27, 50, 51, 56, 75, 76, 79, 82, 114, 287, 373-377, 379, 394, 396-399, 423-428, 430, 450-458, and 461 of SEQ ID NO:1; (ii) 23-27, 50, 51, 56, 72, 75, 76, 79, 82, 113, 114, 287, 352, 373-377, 379, 394, 396-399, 423-428, 430, 450-458, 461, and 532 of SEQ ID NO:1; (iii) 23-27, 48, 49, 54, 74, 75, 78, 81, 113, 286, 376-380, 382, 399, 401-404, 427-432, 434, 454-462, and 465 of SEQ ID NO:2; (iv) 23-27, 48, 49, 54, 71, 74, 75, 78, 81, 112, 113, 286, 356, 376-380, 382, 399, 401-404, 427-432, 434, 454-462, 465, and 535 of SEQ ID NO:2; or (v) 22-29, 32, 43, 46-50, 54, 69-79, 81, 82, 111-113, 240, 285-287, 290, 356, 360, 376-383, 398-407, 426-435, 453-466, 472, 473, 475, 477, 526-528, and 530-535 of SEQ ID NO:2.

Amino acid positions corresponding to any one or more of the foregoing residues can be determined by structural alignment to a template structure (e.g., a structure of SEQ ID NO:1 or 2). One or both structures used in the structural alignment can be experimentally determined or determined by homology modeling using any one or more of the homology modelling methods described herein. Exemplary structural alignment methods and/or programs include, but are not limited to, TM-align, LSQMAN, Fr-TM-align, DALI, DaliLite, CE, CE-MC, and the like. Additional structural alignment tools useful in determining active site amino acids include, but are not limited to, those described in web.archive.org/web/20151221055428/https://en.wikipedia.org/wiki/Structural_alignment_software.

As used herein, "rosetta energy units" in the context of ligand binding interaction energy refers to an interaction energy between a bound ligand and a protein calculated using Rosetta Enzyme Design style constraints. Program code for calculating rosetta energy units is provided herein.

DETAILED DESCRIPTION OF THE INVENTION

I. Introduction

In the current synthetic recursive+1 pathway, the enzymes LeuA, LeuB, LeuC, and LeuD (collectively known as LeuABCD) are recruited to recursively elongate 2-ketobutyrate into longer chain 2-ketoacids.[3,4] These 2-ketoacids are then converted to aldehydes by ketoisovalerate decarboxylase[6] (KIVD) and subsequently to alcohols by alcohol dehydrogenase[3] (ADH). (Figure. 1) In this engineered pathway, the primary determinant for the final product chain length is the number of cycles through LeuABCD.[7] (FIG. 1)

Previous efforts to engineer the product specificity of this pathway have focused on broadening the specificity of LeuA and KIVD. When the specificity of LeuA and KIVD are broadened, branched $C_8$ products are produced.[3] When only the specificity of LeuA is broadened, additional cycles through the pathway are carried out, resulting in a mixture of $C_2$-$C_8$ linear alcohols;[4] however, the primary product is still 1-butanol. In order to enhance long chain alcohol production, the inventors have focused on discovering a ketoacid decarboxylase specific for long chain ketoacids. By replacing KIVD with an enzyme specific for long chain ketoacids, the short chain substrates are able to reenter the +1 iteration cycle until conversion to long chain ketoacids, which are then decarboxylated and reduced into the corresponding long chain alcohols.

II. Methods

Provided herein are methods of identifying 2-ketoacid decarboxylase enzymes having an altered specificity, or having a desired endogenous specificity. In some cases, the 2-ketoacid decarboxylases have or are altered to have improved specificity for or catalytic efficiency against long chain (≥C5) ketoacids and/or provide or are altered to provide an increased amount or concentration of long chain (≥C5) alcohols when present in a synthetic recursive+1 pathway in a host cell or reaction mixture, e.g., as compared to SEQ ID NO:1.

The methods can include mining known protein sequences to identify enzymes having homology to a known 2-ketoacid decarboxylase template, at least a subset of which can be predicted to have a desired endogenous specificity or can be predicted to be able to be redesigned to have an altered specificity. Protein sequences having homology to a template enzyme sequence (e.g., SEQ ID NO:1) can, e.g., be identified using a hidden markov model algorithm such as that implemented in HMMER3 or using a BLAST-type sequence similarity search. Sequences can be filtered by removing sequences that are highly similar in sequence, e.g., using CD-HIT. Exemplary cut-offs for highly similar sequences can include a cut-off which removes sequences having at least about 50%, 60%, 70%, 80%, 90%, 95%, or 99% identity to the template sequence.

Structural features of sequences identified as having sequence homology to the template sequence can then be assessed. For example, a homology model of candidate hits can be generated, e.g., using RosettaCM, SWISS-MODEL, MODELLER, 3D-JIGSAW, ModPipe, Fugue, HHPred, i-Tasser, IntFOLD, M4T, ModWeb, Phyre2, RaptorX, Robetta, HHsuite, and the like. Homology models so generated can be scored for three dimensional structural similarity to the structure of the template sequence. For example, a structural alignment program or methods as described herein, including but not limited to one or more of TM align, the DALI server (e.g., DaliLite v. 3 available at ekhidna.biocenter.helsinki.fi/dali_server), or the cealign algorithm implemented in PyMOL (e.g., version 1.7.6 available at www.pymol.org) can be used to assess structural similarity by calculating a TM align score, Z-score, or an RMSD value respectively.

In some embodiments, a TM align score is used to assess structural similarity. For example, a TM align score cut-off of at least about 0.5 to a known 2-ketoacid decarboxylase (e.g., SEQ ID NO:1, SEQ ID NO:2 or any other 2-ketoacid decarboxylases described herein) can be used to filter out candidate 2-ketoacid decarboxylases from homology models of the initial sequence search results or from homology models of the sequence search results after removing highly similar sequences. Alternatively, a more stringent cut-off can be applied. For example, a TM align score of at least about 0.55, 0.6, 0.65, 0.7, 0.75, 0.8, 0.81, 0.815, 0.817, 0.85, or 0.9 can be utilized.

In some embodiments, an RMSD value as calculated by, e.g., cealign or other similar methods or programs can be utilized to assess structural similarity and filter out candidate 2-ketoacid decarboxylases from homology models of the initial sequence search results or from homology models of the sequence search results after removing highly similar sequences. In exemplary embodiments, RMSD cutoffs calculated as described herein of less than about 6.7 Å, 6 Å, 5.5 Å, 5 Å, 4 Å, or 3.5 Å can be used to filter out candidate 2-ketoacid decarboxylases from homology models of the initial sequence search results or from homology models of the sequence search results after removing highly similar sequences. Alternatively, a more stringent cut-off can be applied. For example, an RMSD value of less than about 3 Å, 2.5 Å, 2 Å, or 1.6 Å can be utilized.

In some embodiments, a Z-score calculated by the DALI server is used to assess structural similarity. For example, a Z-score cut-off of at least about 2 to a known 2-ketoacid decarboxylase (e.g., SEQ ID NO:1, SEQ ID NO:2 or any other 2-ketoacid decarboxylases described herein) can be used to filter out candidate 2-ketoacid decarboxylases from homology models of the initial sequence search results or from homology models of the sequence search results after removing highly similar sequences. Alternatively, a more stringent cut-off can be applied. For example, a Z-score of at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 can be utilized.

The homology models (e.g., after removing models that lack significant structural similarity as assessed by, e.g., TM align score, Z-score, and/or RMSD) can be assessed to identify sequences that bind a preferred substrate. For example, a covalent intermediate of a 2-ketoacid decarboxylase reaction can be modeled in the active site of the generated homology models, the complex can be relaxed computationally, e.g., using Rosetta Enzyme Design, and a ligand binding energy calculated. Candidate sequences having a low ligand binding energy can be selected for in vitro and/or in vivo analysis or selected as a preferred enzyme for catalyzing decarboxylation of a substrate to produce a product that corresponds to the modeled catalytic intermediate ligand. In some embodiments, candidate sequences having a ligand binding energy of less than, or less than about, −5, −5.5, −6, −6.5, −7, −7.5, −8, −8.5, −9, −9.5, −10, −10.3, −10.4, −10.5, −10.6, −10.7, −10.8, −10.9, −11, −11.5, −12, −12.5, −13, −13.5, −14, −14.5, −15, −15.5, −16, −16.5, −17, −17.5, −18, −18.5, −19, −19.5, or −20 Rosetta energy units can be selected for in vitro and/or in vivo analysis or selected as a preferred enzyme for catalyzing decarboxylation of a substrate to produce a product that corresponds to the modeled catalytic intermediate ligand.

Methods of identifying 2-ketoacid decarboxylase enzymes having a desired altered specificity (e.g., greater catalytic efficiency against long chain (≥$C_5$) ketoacids) can additionally or alternatively include reprogramming substrate specificity of a known 2-ketoacid decarboxylase (e.g., SEQ ID NO:1 or any of the GEOs described herein) using computation enzyme design methods. For example, the Rosetta Molecular Modeling Suite, or another computational design platform, can be used to design such enzymes. For example, experimentally determined structures and/or homology models of known or suspected 2-ketoacid decarboxylases can be used to explore potential active-site sequence space that would accommodate long chain (≥C5) 2-ketoacids, e.g., 2-ketooctanoate as substrates. In some embodiments, a modeled reaction intermediate of, e.g., a C8 substrate, is docked within a predicted active site of an experimentally determined structure or homology model structure, the complex optionally minimized, and a ligand binding energy calculated. In some embodiments, ligand binding energies are sampled among a number of computationally generated enzyme mutations or ensemble conformations by allowing the identity and conformation of non-catalytic residues within the active site to change, and/or allowing backbone distances and/or angles to move during minimization.

Candidate 2-ketoacid decarboxylases can be cloned into an expression cassette, e.g., under the control of a promoter such as a heterologous promoter, expressed and assayed for activity. For example 2-ketoacid decarboxylase enzymes identified by one or more of sequence mining, homology modeling, structural similarity scoring, and ligand binding analysis can be assayed for activity against one or more 2-ketoacid substrates. As another example, 2-ketoacid decarboxylase enzymes identified by virtual screening of mutants of a known 2-ketoacid decarboxylase can be assayed for activity against one or more 2-ketoacid substrates.

II. Compositions

Described herein are 2-ketoacid decarboxylases, expression cassettes encoding such 2-ketoacid decarboxylases, and host-cells and/or reaction mixtures containing such 2-ketoacid decarboxylases or expression cassettes. In some embodiments, the expression cassette is heterologous to the host cell or reaction mixture in which it resides. In some embodiments, the expression cassette contains a heterologous promoter operably linked to a polynucleotide encoding a 2-ketoacid decarboxylase. The expression cassette can, e.g., comprise a heterologous promoter operably linked to a nucleic acid encoding an enzyme comprising 2-ketoacid decarboxylase activity, wherein the enzyme: comprises a 3-layer alpha-beta-alpha sandwich; comprises a thiamine pyrophosphate (TPP) binding pocket; has a TM align score of at least 0.5 as compared against PDB ID:2VBG; and comprises at least a 100-fold greater catalytic efficiency for C8 2-ketoacid substrates as compared to C3 or isoC5 2-ketoacid substrates, wherein the catalytic efficiency is measured by kcat/Km.

In some cases, the enzyme comprising 2-ketoacid decarboxylase activity comprises an amino acid sequence that is at least 10%, 12%, 14%, 15%, 20%, 25%, 30%, 35%, 40%, 50%, 60%, 70%, 80%, 90% or 99% identical to SEQ ID NO:1. Sequence identity can be determined using methods known in the art. For example, using BLAST, HMMER3, or the like, e.g., using the default settings.

In some cases, the enzyme comprising 2-ketoacid decarboxylase activity has a TM align score of at least 0.4, 0.45, 0.5, 0.55, 0.6, 0.65, 0.7, 0.75, 0.8, 0.81, 0.815, 0.817, 0.85, or 0.9; a Z-score of or of at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62; or an RMSD of or of less than about 6.7 Å, 6 Å, 5.5 Å, 5 Å, 4 Å, 3.5 Å 3 Å, 2.5 Å, 2 Å, or 1.6 Å as compared against PDB ID:2VBG. In some cases, the substrate binding pocket of the enzyme has a solvent accessible surface area of, or of at least about 7,500; 8,000; 8,500; 9,000; 9,500; or 10,000 Å$^2$.

In some cases, the enzyme comprising 2-ketoacid decarboxylase activity comprises an amino acid sequence that contains a mutation of a native sequence wherein the mutation is in an amino acid residue with a Cα within 8 Å of a 2-ketoacid decarboxylase active site, wherein the 2-ketoacid decarboxylase active site comprises the amino acids corresponding to one or more of (e.g., corresponding to 2, 3, 4, 5, 6, 7, 8, 9, 10, 11, 12, 13,14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 of) the following amino acid positions: (i) 23-27, 50, 51, 56, 75, 76, 79, 82, 114, 287, 373-377, 379, 394, 396-399, 423-428, 430, 450-458, and 461 of SEQ ID NO:1; (ii) 23-27, 50, 51, 56, 72, 75, 76, 79, 82, 113, 114, 287, 352, 373-377, 379, 394, 396-399, 423-428, 430, 450-458, 461, and 532 of SEQ ID NO:1; (iii) 23-27, 48, 49, 54, 74, 75, 78, 81, 113, 286, 376-380, 382, 399, 401-404, 427-432, 434, 454-462, and 465 of SEQ ID NO:2; (iv) 23-27, 48, 49, 54, 71, 74, 75, 78, 81, 112, 113, 286, 356, 376-380, 382, 399, 401-404, 427-432, 434, 454-462, 465, and 535 of SEQ ID NO:2; or (v) 22-29, 32, 43, 46-50, 54, 69-79, 81, 82, 111-113, 240, 285-287, 290, 356, 360, 376-383, 398-407, 426-435, 453-466, 472, 473, 475, 477, 526-528, and 530-535.

Amino acid positions corresponding to any one or more of the foregoing residues can be determined by structural alignment to a template structure (e.g., a structure of SEQ ID NO:1 or 2). One or both structures used in the structural alignment can be experimentally determined or determined by homology modeling using any one or more of the homology modelling methods described herein. Exemplary structural alignment methods and/or programs include, but are not limited to, TM-align, LSQMAN, Fr-TM-align, DALI, DaliLite, CE, CE-MC, and the like. Additional structural alignment tools useful in determining active site amino acids include, but are not limited to, those described in en.wikipedia.org/wiki/Structural alignment software.

In some embodiments, the enzyme comprising 2-ketoacid decarboxylase activity comprises an amino acid sequence that contains a mutation in an amino acid residue corresponding to a residue selected from the group consisting of G402, M538, and F542 of SEQ ID NO:1. In some embodiments, the mutation in an amino acid residue corresponding to a residue selected from the group consisting of G402, M538, and F542 of SEQ ID NO:1, and wherein the mutation is to a residue selected from the group consisting of Val, Leu, Ile, Met, Phe, His, Gly, Ala, Thr, Tyr, and Trp. In some embodiments, the mutation in an amino acid residue corresponding to a mutation selected from the group consisting of G402V, M538L, and F542V of SEQ ID NO:1. In some embodiments, the enzyme comprising 2-ketoacid decarboxylase activity comprises two or three mutations in amino acid residues corresponding to residues selected from the group consisting of G402, M538, and F542 of SEQ ID NO:1. In some cases, the enzyme comprising 2-ketoacid decarboxylase activity comprises one, two, or three of the mutations corresponding to G402V, M538L, and F542V of SEQ ID NO:1.

In some embodiments, the enzyme comprising 2-ketoacid decarboxylase activity comprises SEQ ID NO:2 or SEQ ID NO:3. In some embodiments, the enzyme is, or is at least about, 80%, 90% or 99% identical to SEQ ID NO:2 or 3. In some embodiments, the enzyme comprises 1, 2, 3, 4, 5, 6, 7, 8, 9, 10, 11, 12, 13, 14, 15, 16, 17, 18, 19, 20, or more insertions, substitutions, or deletions, relative to SEQ ID NO:1, 2 or 3, or relative to any of the GEOs described herein. In some cases, the insertion, substitution, or deletion is independently an insertion, substitution, or deletion of 1, 2, 3, or 4 amino acids at a given amino acid position.

In some embodiments, the enzyme comprising 2-ketoacid decarboxylase activity interacts with a C8 2-ketoacid substrate with a calculated interaction energy of less than, or less than about, −10, −10.3, −10.4, −10.5, −10.6, −10.7, −10.8, −10.9, −11, −11.5, −12, −12.5, −13, −13.5, −14, −14.5, −15, −15.5, −16, −16.5, −17, −17.5, −18, −18.5, −19, −19.5, or −20 Rosetta energy units.

All patents, patent applications, and other publications, including GenBank Accession Numbers, cited in this application are incorporated by reference in the entirety for all purposes.

EXAMPLES

The following examples are provided by way of illustration only and not by way of limitation. Those of skill in the art will readily recognize a variety of non-critical parameters that could be changed or modified to yield essentially the same or similar results.

Example 1

Introduction

To rationally engineer the product profile of the synthetic recursive+1 pathway two computationally directed approaches were employed to discover a decarboxylase with the desired functional profile. The first is a new approach to mine the rapidly growing sequence databases derived from genomic sequencing. Since the vast majority of these proteins are derived from the genomic sequencing of organisms (i.e., genomic enzyme orthologs: GEOs), most of them have not been experimentally characterized and neither function nor specificity is known. Previous efforts to mine GEOs for function have relied on random sampling or sequence-based bioinformatics over an entire enzyme family.[8,9,10] While enzymes with a desired function have been found using these methods, it requires a large number of genes to be produced and experimentally characterized. To enable a more efficient sampling method, a novel computational pipeline was developed that integrates the use of bioinformatics and molecular modeling to carry out forward predictions of a GEO's ability to carry out a function of interest. Using this integrative genomic mining approach a highly diverse set of ketoacid decarboxylases capable of utilizing 2-ketooctanoate (C8) as a substrate was identified. The median activity of GEOs selected using the integrative genomic mining approach is 75-fold greater than a set of naively selected proteins from the enzyme family.

The second approach focuses on reprogramming the substrate specificity of KIVD by using computational enzyme design methods. The Rosetta Molecular Modeling Suite was used to direct the generation and screening of over 400 mutants.[11] This effort lead to the discovery of a mutant with >600-fold increase in specificity for C8. Finally, the most specific and active enzyme from each approach is incorporated into the synthetic recursive+1 pathway to evaluate its ability to modulate in vivo alcohol production. Both enzymes result in a complete switch of the alcohol production profile towards long chain alcohols, demonstrating the ability to rationally control biosynthetic product specificity for chemicals not commonly found in Nature.

Results

Integrative Genomic Mining for Enzyme Function

KIVD belongs to the thiamine pyrophosphate enzyme family that is composed of more than 17,000 sequences.[12] To identify GEOs with the desired function within this vast sequence space, bioinformatics[13] and molecular modeling[14] with functional constraints were combined to guide our exploration. (FIG. 2) First, ketoacid decarboxylase GEOs were identified based on sequence similarity to the KIVD used in the current synthetic recursive+1 pathway. At the time the search was performed, 2082 sequences were found in the non-redundant sequence database as significant matches. To broadly search KIVD sequence space, redundant sequences were filtered out with a sequence identity cut-off of 90%.[15] Sequences derived from eukaryotic organisms were removed in order to increase the likelihood of producing soluble proteins in *E. coli* where the synthetic recursive+1 pathway has been implemented.

The approach assumed that all potential scaffolds with the desired function should be structurally homologous to KIVD and the sequence set was further refined accordingly. Since crystal structures for most of these predicted proteins are not available for analysis, homology models were produced to obtain a predicted ternary structure. Using RosettaCM one hundred models were generated for each of the 239 GEOs.[14] The lowest energy model was selected as the representative for each GEO and evaluated for structural similarity to KIVD. The TMalign algorithm[16] was used to overlay the models with the native KIVD crystal structure and only those with a TMalign score of >0.5 were kept. These bioinformatics and structural filters resulted in 239 GEOs as candidates for the targeted function. (FIG. 16) The pairwise identity of every sequence to each other was calculated and the mode of these values lies near 20%. (FIG. 2) Thus the selected set of 239 GEOs represents a diverse sampling of sequence space for this fold family.

To further enrich the set for GEOs likely to function on C8, a modeled reaction intermediate of the C8 substrate was docked within the predicted active site. The lowest energy model for each GEO was used as a template for docking a modeled C8 intermediate with functional constraints, which ensured a productive geometric orientation between the predicted catalytic residues in the protein and intermediate. The C8 reaction intermediate used for docking is based on the synthetic thiamine pyrophosphate (TPP) analogue from a crystal structure of KIVD (PDB ID: 2VBG), which mimics the initial nucleophilic attack by the thiazolium.[17] Docking calculations were carried out using Rosetta Design in which both the identity and conformation of non-catalytic residues within the active site were allowed to change, and the backbone was allowed to move during minimization. The calculated interface energy after the dock and design simulations was used to evaluate each GEO's ability to accommodate C8.

A phylogenetic tree based on sequence similarity was built for the 239 GEOs in which the lowest protein-ligand interface energy from the Rosetta Design simulation for each GEO are depicted. (FIG. 2) The bar height above each GEO leaf is proportional to the lowest interface energy from all 239 GEOs, the higher the bar the lower the energy. Based on the calculated energies it is immediately apparent that a cluster of GEOs distant in sequence to KIVD (~15% sequence identity) is predicted to be capable of utilizing C8. The enzyme with the lowest energy, GEO 175, is a predicted protein in the genome database with no known function. The closest enzyme to GEO 175 (~50% sequence identity) for which significant biophysical characterization has been performed is benzoylformate decarboxylase from bacteria *Pseudomonas putida* (ppBFD).[18] A structural analysis of the active site of ppBFD and GEO 175 reveals that the active sites are only 50% identical in sequence (FIG. 10), and the activity of ppBFD on C8 has not been previously studied.

From the design simulations, ten GEOs were chosen for experimental characterization based on the predicted protein-ligand interface energy as well as sequence diversity (FIG. 2, FIG. 16). Before ordering these GEOs, each protein was manually analyzed and mutations introduced through the Rosetta Design simulations were reverted if they were not predicted to significantly enhance the calculated Rosetta interface energy. Synthetic genes encoding each enzyme was obtained, expressed in *E. coli* and purified for in vitro kinetic characterization using a panel of 2-ketoacid substrates of different chain lengths including C8, C5, C3 and the natural substrate for KIVD ketoisovaleric acid (FIG. 3). Out of the 10 selected GEOs, six express and are able to be purified in a soluble form using our standardized method. Of these six, three exhibit detectable activities on at least one of the four ketoacids used for kinetic characterization.

Among the active GEOs, the enzyme with the highest efficiency on C8 is the computationally top ranked GEO 175, with a $k_{cat}/K_M$ of 17,000 M$^{-1}$s$^{-1}$. (Table 1, FIG. 4) This is only 2-fold lower than the efficiency of native KIVD on C8. However, GEO 175's catalytic efficiency on C8 is 33,000-fold higher than on C3 and 354-fold higher than on C5. When assayed under the same conditions, native KIVD's catalytic efficiency on C8 is 762-fold higher than on C3 and 3.4-fold higher than on C5. This corresponds to over a 100-fold improvement in specificity (C8 versus C5) relative to the native KIVD.

TABLE 1

| Kinetic Characteristics of 2-ketoacid Decarboxylase Enzymes | | | | |
|---|---|---|---|---|
| | C3 | C5 | C8 | iso C5 |
| | $k_{cat}/K_M$ (M$^{-1}$ s$^{-1}$) | | | |
| GEO179 | 0.90 ± 0.02 | 100 ± 15 | 1200 ± 130 | 41 ±1.2 |
| GEO195 | 2.4 ± 0.1 | 200 ± 14 | 1400 ± 160 | 8.0 ± 0.3 |
| GEO175 | 0.51 ± 0.02 | 48.0 ± 3.7 | 17000 ± 2700 | 3.3 ± 0.2 |
| GEO175 L376T_T240S | 0.27 ± 0.02 | 30.0 ± 7.2 | 1100 ± 160 | 1.6 ± 0.1 |
| 1OVM | 32.0 ± 0.5 | 2100 ± 420 | 80000 ± 4300 | 1300 ± 130 |
| 2VBI | 5700 ± 1400 | 52.0 ± 1.8 | 14.0 ± 0.8 | 1.8 ± 0.1 |
| 3FZN | 5.4 ± 0.1 | 1700 ± 110 | 350 ± 30 | 110 ± 10 |
| 1ZPD | 8200 ± 545 | 140.0 ± 5.6 | 19.0 ± 2.0 | 0.33 ± 0.01 |
| 1OZF | n.d. | 0.53 ± 0.04 | n.d. | 17.0 ± 0.9 |
| Native KIVD | 42.0 ± 0.6 | 9500 ± 470 | 32000 ± 5500 | 14000 ± 1100 |
| KIVD_VLV | 0.71 ± 0.07 | 1.3 ± 0.2 | 2800 ± 860 | 0.24 ± 0.02 |
| | $k_{cat}$ (s$^{-1}$) | | | |
| GEO179 | n.d. | 0.47 ± 0.03 | 0.32 ± 0.01 | 0.39 ± 0.01 |
| GEO195 | n.d. | 0.49 ± 0.01 | 0.56 ± 0.02 | 0.072 ± 0.001 |
| GEO175 | n.d. | 0.97 ± 0.04 | 10.1 ± 0.6 | n.d. |

TABLE 1-continued

Kinetic Characteristics of 2-ketoacid Decarboxylase Enzymes

|  | C3 | C5 | C8 | iso C5 |
|---|---|---|---|---|
| GEO175 L376T_T240S | n.d. | 0.28 ± 0.04 | 3.4 ± 0.2 | n.d. |
| 1OVM | 0.2 ± 0.01 | 1.0 ± 0.1 | 1.7 ± 0.1 | 7.8 ± 0.4 |
| 2VBI | 25 ± 2.6 | n.d. | 0.051 ± 0.01 | 0.025 ± 0.001 |
| 3FZN | n.d. | 4.7 ± 0.1 | 1.3 ± 0.1 | 0.52 ± 0.02 |
| 1ZPD | 46.7 ± 1.4 | 0.95 ± 0.02 | 0.021 ± 0.001 | n.d. |
| 1OZF | n.d. | n.d. | n.d. | 0.030 ± 0.001 |
| Native KIVD | n.d. | 14.3 ± 0.2 | 7.0 ± 0.3 | 61.0 ± 2.1 |
| KIVD_VLV | n.d. | 0.013 ± 0.001 | 0.50 ± 0.03 | n.d. |
| $K_M$ (mM) | | | | |
| GEO179 | n.d. | 4.6 ± 0.6 | 0.27 ± 0.03 | 9.4 ± 0.2 |
| GEO195 | n.d. | 2.5 ± 0.2 | 0.40 ± 0.04 | 9.1 ± 0.3 |
| GEO175 | n.d. | 20.0 ± 1.3 | 0.58 ± 0.09 | n.d. |
| GEO175 L376T_T240S | n.d. | 10 ± 2 | 3.1 ± 0.4 | n.d. |
| 1OVM | 7.5 ± 0.1 | 0.5 ± 0.1 | 0.021 ± 0.001 | 6.1 ± 0.6 |
| 2VBI | 4.3 ± 1.0 | n.d. | 3.6 ± 0.2 | 14.0 ± 0.5 |
| 3FZN | n.d. | 2.7 ± 0.2 | 3.8 ± 0.3 | 4.9 ± 0.3 |
| 1ZPD | 5.7 ± 0.3 | 7.1 ± 0.3 | 1.2 ± 0.1 | n.d. |
| 1OZF | n.d. | n.d. | n.d. | 1.8 ± 0.1 |
| Native KIVD | n.d. | 1.5 ± 0.1 | 0.21 ± 0.04 | 4.5 ± 0.3 |
| KIVD_VLV | n.d. | 10.0 ± 1.0 | 0.18 ± 0.05 | n.d. |

To evaluate if the integrative genomic mining approach enriches the mining for C8 activity, an additional set of previously characterized ketoacid decarboxylases diverse in sequence were experimentally characterized in an equivalent manner. Five enzymes were selected (PDB: 1OVM, 2VBI, 3FZN, 1ZPD, 1OZF) and all were found to have detectable activity on at least one of the four ketoacids used for GEO characterization. The median C8 activity from the GEOs selected using the integrative genomic mining approach is 75-fold higher than the naively picked decarboxylases (Table 1, FIG. 4). This indicates the integrative genomic mining approach is effective in identifying functional enzymes that perform the desired reaction on C8.

The protein sequence for GEO 175 is not predicted to require any mutations to be capable of utilizing the C8 substrate, and therefore represents the native enzyme from *Streptomyces* sp. C. Comparing the active site pocket of GEO 175 with native KIVD (16.8% identity to each other) reveal significant differences which gave implications to the high specificity of this newly identified enzyme. (FIG. 5) Based on molecular modeling, GEO 175 is predicted to have an extended active site that is significantly more open to solvent relative to native KIVD. This results in the predicted binding mode for C8 to be extended in GEO 175 as opposed to a "wrapped" conformation in KIVD. In GEO175, the third through fifth carbons of the C8 ketoacid ligand are predicted to occupy a solvent-exposed, open pocket with limited molecular interactions. However the sixth through eighth carbons are predicted to interact with a narrow and hydrophobic pocket. Contrary to GEO 175, KIVD has an enclosed hydrophobic binding pocket and is predicted to make molecular interactions throughout the ketoacid alkyl chain (FIG. 5).

From these observations it was hypothesized that the specificity of GEO 175 could be attributed to a combination of hydrophobic interactions with the sixth through eighth carbons of the alkyl chain, while lacking interactions with the third through fifth carbons. (FIG. 6) Therefore, an engineered mutant of GEO 175 containing two amino acid changes (L376T, T240S) (SEQ ID NO:19) predicted to remove the direct molecular interactions with seventh and eighth carbons of the ketoacid alkyl chain, while maintaining overall protein stability was generated. Upon kinetic characterization, it was found that the mutant protein's catalytic efficiency on C8 is 15-fold lower than GEO 175, but the decrease in efficiency for C5, C3, and isoC5 assayed under the same conditions is less than 2-fold. The ability to rationally modulate activity based on structure supports the accuracy of the GEO 175 molecular model.

Computationally Directed KIVD Active Site Redesign

In the second effort to reprogram the specificity of KIVD, Rosetta Design methods were used to explore the potential active site sequence space that would accommodate 2-ketooctanoate as a substrate.[11] Design simulations were carried out with the same reaction intermediate and functional constraints utilized in the genomic mining pipeline. Ten residues in the active site were targeted for mutagenesis. At each site, one of eleven relatively hydrophobic amino acids (Val, Leu, Ile, Met, Phe, His, Gly, Ala, Thr, Tyr, Trp) was systematically introduced, and the remaining nine sites were allowed to be redesigned. The identities of amino acids at all other residues were kept constant. (FIG. 7) The sequence profile from the 50 lowest energy designs was used to guide construction of a small library of roughly 400 KIVD mutants from the original combinatorial space of over $10^{11}$ possible active site mutations.

Since KIVD can already efficiently utilize C8 as a substrate, enzyme specificity is of primary importance. Therefore each mutant was screened against a panel of 2-ketoacid substrates in order to assess the specificity and activity of each mutant. (FIG. 11) This assay was performed using a high-throughput pH-dependent colorimetric assay of enzyme activity in crude cell extracts. Mutations that increased specificity for C8 were then combined to produce combinatorial mutants and screened for specificity with the colorimetric assays. The mutant that exhibits the highest specificity and activity is G402V/M538L/F542V (KIVD_VLV). The engineered enzyme KIVD_VLV has a 600-fold improvement in specificity between C8 and C5, in terms of catalytic efficiency, relative to the native KIVD.

In Vivo Testing of Engineered and Genomic Enzymes for Long-Chain Alcohol Production The measured specificity and activity for each enzyme was used to select two candidates for further characterization of their ability to modulate alcohol production in vivo. The two enzymes with the highest activity and specificity (FIG. 4), KIVD_VLV and GEO 175, were tested for their ability to reprogram the synthetic recursive+1 pathway to produce long-chain alcohol products in vivo. The alcohol-producing biochemical pathway was adapted from a previous study used to synthesize alcohols of various lengths.[3,4] Starting from glucose, the aforementioned+1 pathway, involving LeuABCD, recursively elongates 2-ketoacids, starting with 2-ketobutyrate, into longer chained 2-ketoacids. These 2-ketoacids are then converted to aldehydes by ketoacid decarboxylases (native KIVD, KIVD_VLV, and GEO 175) and subsequently to alcohols by an alcohol dehydrogenase. Carbon flux through this alcohol synthesizing biochemical pathway is enhanced by overexpressing thrABC, ilvA, LeuABCD, and ADH6 on inducible plasmids transformed into E. coli.[3] The effects of overexpression were furthermore supported and maintained by knocking out the threonine exporter enzyme RhtA and the primary DNA recombination degradation enzyme RecA. The enzyme AdhE was also knocked out, which helps raise long chain alcohol production by eliminating a competing pathway where acetyl-CoA is directly converted to ethanol.[19]

Consistent with previous reports, the primary products (82% of total alcohol production) with native KIVD are short alcohols ($C_2$-$C_4$) (FIG. 8, Table 2). The KIVD_VLV triple mutant completely switches the product profile of this pathway to predominantly long chain (≥C5) alcohols at 728 mg l$^{-1}$. Hexanol (C6) is the major alcohol detected at a titer of 341 mg l$^{-1}$ (47%), with titers of 269 mg l$^{-1}$ (37%) heptanol (C7), and 118 mg l$^{-1}$ pentanol (16%) also observed. GEO 175 also switches the product profile of the pathway so that long chain alcohols are the primary products and produced at a level of 522 mg l$^{-1}$. For GEO175 the product profile is further shifted, resulting in heptanol ($C_7$) as the major product at a titer of 274 mg l$^{-1}$ (50%), with hexanol production at 160 mg l$^{-1}$ (29%), and 88 mg l$^{-1}$ pentanol (16%). Similar to the results for KIVD_VLV, no ethanol or propanol production is observed, and only 19 mg l$^{-1}$ butanol is produced. In addition, 10 mg l$^{-1}$ of octanol was also observed, a product not observed when either native KIVD, or KIVD_VLV were tested under equivalent conditions. The in vivo butanol and octanol titers for GEO175 compared to KIVD_VLV are consistent with the in vitro enzyme kinetics in which GEO175 has a significantly higher activity on C8, but lower specificity relative to C5, than KIVD_VLV. Total long chain alcohol titers for both GEO 175 and KIVD_VLV are increased significantly in comparison to native KIVD, with a >10-fold increase in heptanol production in both cases, and a >95% yield of long chain alcohols.

TABLE 2

In vivo Alcohol Production

| | Native KIVD (mg/L) | KIVD_VLV (mg/L) | GEO 175 (mg/L) |
|---|---|---|---|
| 1-Ethanol | 652 ± 32 | n.d. | n.d. |
| 1-Propanol | 693 ± 4 | n.d. | n.d. |
| 1-Butanol | 1964 ± 24 | n.d. | 19 ± 2 |
| 1-Pentanol | 594 ± 20 | 118 ± 29 | 88 ± 12 |
| 1-Hexanol | 75 ± 6 | 341 ± 63 | 160 ± 18 |
| 1-Heptanol | 20 ± 3 | 269 ± 23 | 274 ± 19 |
| 1-Octanol | n.d. | n.d. | 10 ± 1 |

Cells were incubated for forty hours in microaerobic conditions in a defined media. The best enzyme in shifting the product profile was GEO175 with 1-heptanol being the major product.

Replacing KIVD with GEO 175 or KIVD_VLV results in a significant increase of long chain alcohol production, however the overall alcohol production drops ~10-fold from the 4.0 g/L obtained with KIVD. We hypothesized that a potential reason for this could be due to the toxicity of long chain alcohols. To explore the potential of toxicity being a limiting factor in alcohol production, E. coli growth was monitored over a 7-hour incubation with 10-1000 mg l$^{-1}$ $C_5$-$C_8$ alcohols supplemented at the beginning of growth. (FIG. 9) Long chain alcohols are found to be toxic as the supplemented concentration of $C_6$-$C_8$ alcohols reach 250 mg l$^{-1}$. The final OD of E. coli cultures drops from 1.9 to approximately 1.6 for C6 and C7 alcohols, and 1.0 for $C_8$. At 500 mg l$^{-1}$ the OD drops to 1.0 and 0.1 for $C_6$ and $C_7$ alcohols, respectively. No significant growth is observed for $C_8$. At 1000 mg l$^{-1}$ no significant growth is observed for heptanol, and only an OD of 0.2 is achieved in the presence of hexanol. However, growth up to an OD of 1.5 is observed for pentanol. Significant toxicity in the range of 250 to 1000 mg l$^{-1}$ for long chain alcohols is consistent with the level of long chain alcohol titer, roughly 500 mg/L, produced in the engineered E. coli strains. This result indicates that in order to achieve higher total alcohol titer with this pathway, a strain of E. coli with high tolerance toward long chain alcohols is likely necessary.[20,21] However, similar issues with product toxicity have been addressed through the design of continuous extraction methods and could be applied to the system here to increase levels of long chain alcohols titers.[22]

Discussion

In this study an integrative genomic mining approach was introduced to enable discovery of enzymes for a targeted function from sequence databases. The function of interest here was an enzyme with high activity for the decarboxylation of long chain ketoacids in order to modulate the carbon flux of a synthetic pathway and increase titers of long-chain alcohols. The integrative genomic mining approach led to the discovery of a previously uncharacterized protein that we demonstrate has the targeted functional properties, and only required experimental characterization of ten new proteins. In parallel, a more traditional computationally directed library screening approach was utilized to reengineer the activity of a well-established enzyme. This required two successive rounds of screening over four hundred mutants against a panel of substrates in order to identify an enzyme with the desired functional properties. When evaluated for their ability to modulate carbon flux in vivo both are able to completely shift the product profile towards long chain alcohols.

The enzyme GEO 175 represents the product of a general and rapid approach for obtaining enzymes with a desired function from the rapidly growing sequence databases. This approach provides a viable alternative to often expensive and laborious enzyme engineering efforts that require screening libraries of mutants. By combining bioinformatics and molecular modeling this approach enables the identification of proteins likely to carry out a targeted function regardless of their native or putatively annotated activity. This overcomes issues with misannotation of protein function[23] or biased assumptions based on the closest, but often distal in sequence, characterized protein. The enzyme identified in this study, GEO175, is a clear illustration of this as it is roughly 15% identical to KIVD and its closest characterized sequence homolog (ppBFD, roughly 50% sequence identity) has a significantly different functional profile.

While GEO175 and KIVD_VLV both increased long chain alcohol titer >10-fold, we identified that toxicity needs to be addressed in order to further increase total long-chain alcohol titer. The titer of long chain alcohols produced is on the order of 0.5 g/L, which we then demonstrate is highly toxic for the cell lines used in this study. For industrial applications, bio-alcohol production often requires yields on the order of grams per liter.[24] To avoid the need of a continuous extraction fermentation system, future efforts for increasing long chain alcohol production should focus on engineering or finding strains that are tolerant to this level of product formation. Efforts to integrate pumps and reengineer the cell wall to be resistant to alcohols could potentially mitigate toxicity effects and concurrently enable higher titers of long-chain alcohols to be produced through this pathway.[20,21]

In summary, a new genomic mining approach and computationally directed library design efforts were both successfully implemented to obtain enzymes that enabled specific production of long chain alcohols in vivo. These results demonstrate the modularity of the synthetic+1 recursive pathway and provided a clear path forward to engineer industrial level production of long-chain alcohols. Finally, the integrative genomic mining approach introduced here is highly general, and with the rapid growth of sequence databases it has the potential to revolutionize the development and discovery of enzyme catalysts.

Methods

Integrative Genomic Mining

To obtain the GEO sequences, the native KIVD sequence was input for a homologous sequence search using HMMER3's* online server.[13] The resulting sequences were filtered using the CD-HIT* online server with a 90% identity cutoff.[15,25] A homology model of each sequence was made using Rosetta Comparative Modeling.[14] At this point, the intermediate was placed into the active site and 1000 simulations were ran to relax the intermediate according to the constraints. For each model, the lowest 100 in overall protein energy models were selected and then from that subset, the lowest protein-ligand interface was chosen as the energy for the GEO.

An intermediate of the C8 product-yielding reaction was modeled using Spartan*.[26] Different conformations of the alkyl chain were included in the modeling and a conformational library was made using OpenEye Omega*.[27] For the enzyme design of KIVD, this intermediate was placed into the active site using distance and angle constraints. Rosetta Enzyme Design was run with default settings, an example of which is provided in the Rosetta Molecular Modeling Suite demos.

From the design simulations for each GEO the lowest protein-ligand interface Rosetta energy was used to select a tractable number of GEOs for experimental characterization. During these simulations, any amino acids with a $C_\alpha$ within 8 Å of the active site could be mutated to any of the 20 amino acids. An exemplary mapping of GEO175 active site residues to 2VBG active site residues is provided as Table 3. Ten GEOs of significant interest were chosen with the following criteria: Five GEOs were chosen because they had the lowest predicted energies; the second five were chosen with the purpose of maximizing sequence space diversity. The 234 GEOs (less the five lowest in energy) were filtered with a sequence identity cutoff of 40% and the five sequences from this filtered list with the lowest energy were picked as the second five GEOs in our final list. Each model was evaluated in the Foldit interface and mutations made during the design simulations were reverted to the native amino acid if not predicted to improve the interface energy by more than 2 Rosetta energy units.

TABLE 3

Mapping of GEO175 active site residues to active site residues in 2VBG crystal structure

| GEO175 Active Site Amino Acid Position | Corresponding Amino Acid position in 2VBG Crystal Structure |
|---|---|
| 23 | 23 |
| 24 | 24 |
| 25 | 25 |
| 26 | 26 |
| 27 | 27 |
| 48 | 50 |
| 49 | 51 |
| 54 | 56 |
| 71 | gap before 73 |
| 74 | 75 |
| 75 | 76 |
| 78 | 79 |
| 81 | 82 |
| 112 | 113 |
| 113 | 114 |
| 286 | 287 |
| 356 | 352 |
| 376 | 373 |
| 377 | 374 |
| 378 | 375 |
| 379 | 376 |
| 380 | 377 |
| 382 | 379 |
| 399 | 394 |
| 401 | 396 |
| 402 | 397 |
| 403 | 398 |
| 404 | 399 |
| 427 | gap before 424 |
| 428 | 424 |
| 429 | 425 |
| 430 | 426 |
| 431 | 427 |
| 432 | 428 |
| 434 | 430 |
| 454 | 450 |
| 455 | 451 |
| 456 | 452 |
| 457 | 453 |
| 458 | 454 |
| 459 | 455 |
| 460 | 456 |
| 461 | 457 |
| 462 | 458 |
| 465 | 461 |
| 535 | 532 |

Phylogenetic tree of GEOs was generated using Geneious software* using a Muscle sequence alignment.[28]* The resulting tree was visualized using iTOL online tool in circular tree mode and rooted at native KIVD.[29,30]

Synthetic genes coding for each GEO were synthesized as a DNA String by Life Technologies or the Joint Genome Institute. Genes were codon optimized for *Escherichia coli* and the amino acid sequences are provided herein. See, FIG. 17 and Sequence Listing. The string was cloned into the pET-29b(+) plasmid vector using the Gibson assembly between the NdeI and XhoI restriction sites which added a C-terminal 6x-His tag in-frame to the gene.

All programs referenced in this section and denoted with an asterisk (*) were run using the default settings unless otherwise specified.

KIVD Active Site Redesign

In the design simulations, ten residues in the proposed active site pocket were allowed to either remain native or sample any of eleven relatively hydrophobic amino acids (Val, Leu, Ile, Met, Phe, His, Gly, Ala, Thr, Tyr, Trp). The identities of amino acids at all other positions were kept constant. Residues within 12 Å of the ligand were allowed to undergo conformational sampling during simulation. A total of 10,000 design simulations were ran, from which the 50 designs lowest in ligand-protein interface energy, and non-redundant in terms of sequence, were selected to represent the potential sequence space predicted to accommodate the C8 substrate. The profile was used to construct a small library of ~400 KIVD mutants. Each amino acid in the library was sampled as a single mutation, with the exception of residues that were within five residues from one another. These were sampled in a combinatorial fashion as both single and double mutants in order to evaluate synergistic effects given their proximity to one another. A complete list of the amino acids allowed for each site is provided in FIG. 18.

Construction and Selection of KIVD Libraries

Partially degenerate oligonucleotides were ordered from Integrated DNA Technologies (San Diego, Calif.) and were used to generate libraries of kivd mutants (with N-terminal his tags) by PCR. Library DNA was purified, inserted into the PCR-amplified pQE9 vector by isothermal Gibson assembly,[31] and transformed into XL1-Blue cells. Individual ampicillin-resistant colonies were picked and grown in 96-well blocks at 37° C. overnight. The number of colonies picked was three times the theoretical library size to ensure approximately 95% probability of all possible mutation combinations occurring. Glycerol was added to 25% (w/v) and libraries were stored at −80° C. until enzyme activity and specificity were assayed. KIVD mutant libraries were screened using a pH-monitored enzyme assay (method explained below) to measure the rate of H+ consumption resulting from the decarboxylation of 2-ketoacids.

KIVD mutant libraries were grown overnight in culture blocks, diluted 1:100 into fresh media (Luria Broth), grown at 37° C. for 3 hours to $OD_{600}$ ~0.6, induced with 0.1 mM IPTG (GoldBio, Saint Louis, Mo.), and grown for 2 additional hours at 37° C. Cells from the well blocks were transferred to 96-well assay plates (Costar, Corning, N.Y.) and cell density was measured at 600 nm. An equal volume of permeabilization solution (8.7 mM potassium phosphate, 43.4 mM KCl, 0.87 mM $MgSO_4$, pH 7.1±0.1, 8.7% (v/v) chloroform, 0.0043% (w/v) SDS, 0.26% (v/v) 2-mercaptoethanol) was then added to break the cell membranes. Bromothymol blue, TPP (Sigma-Aldrich, St. Louis, Mo.), and substrate were added to 0.008% (w/v), 0.5 mM, and 10 mM, respectively. All substrates (2-ketobutyrate, 2-ketovalerate, 2-ketoisovalerate, 2-ketocaproate, and 2-ketooctanoate; Sigma-Aldrich, St. Louis, Mo.) were dissolved in MilliQ $dH_2O$ and pH was adjusted to 7.1±0.1. Absorbance was measured at 615 nm in a spectrophotometer (TEK Powerwave XS, BioTek, Winooski, Vt.). Data were acquired for 15 min at 30° C. Cells containing pQE_hiskivd_wt and pQE9 were used as positive and negative controls, respectively. Enzyme activity data were corrected for cell density. Mutants chosen from this screening had a 25% higher activity than wild-type KIVD for any of the 2-ketoacids.

The library derived from the pH-coupled assay was further screened using a second enzyme kinetics assay. This assay involved a second enzyme, alcohol dehydrogenase from S. Cerevisiae (ADH6), which is a key enzyme in the alcohol production pathway in reducing the aldehyde produced by KIVD into an alcohol. Alcohol dehydrogenase couples oxidation of NADPH to NADP+ to the reduction of aldehyde into an alcohol. Stoichiometrically, conversion of one mole of 2-ketoacid to n-alcohol depletes exactly one mole of NADPH. Therefore, activity of KIVD could be measured directly by measuring depletion of NADPH through ultra-violet spectrophotometry.

Overnight cultures of XL1B with pQE9 containing KIVD mutations were grown at 37° C. in a 96 well block. Cultures were diluted 1:100 and then grown 3 hours at 37° C. to $OD_{600}$ of 0.6. Cultures were induced with 0.1 mM IPTG (GoldBio, Saint Louis, Mo.) for 3 hours at 37° C. Cultures were then centrifuged, and pellets were lysed with BugBuster (Novagen, Madison, Wis.). 5 μL of cell lysate from each culture and 175 μL of a buffer mix containing coenzyme 1.5 mM TPP (Sigma), 0.2 mM NADPH (Fisher, Waltham, Mass.), 0.045 U ADH6, 100 mM $NaPO_4$, 100 mM NaCl, and 10 mM $MgCl_2$, pH of 7 were added together into a 96 well plate. 20 μL of 100 mM substrate was added to dilute to make a final concentration of 10 mM. The substrates tested were IsoC5, C4, C5, C6, C8 and $H_2O$. (FIG. 11) Absorbances were measured with a plate reader (TEK Powerwave XS, BioTek, Winooski, Vt.) at 340 nm at 30° C. for 15 minutes. The protein concentration in each sample was determined with a BCA assay (Thermo Scientific, Waltham, Mass.) and used to normalize slope values. Candidate KIVD mutants were chosen for greater activity on longer chained 2-ketoacids and decreased activity on shorter 2-ketoacids. This was determined from graphing absorbance vs. time for each substrate and qualitatively comparing slope values vs. wild-type (FIG. 11).

Site-Directed Mutagenesis.

Oligonucleotides encoding specific kivd mutations were ordered from Integrated DNA Technologies (Coralville, Iowa) and were used to mutate kivd in pZE_LeuA*BCDKA6 and pQE_hiskivd_wt by PCR. Amplified DNA fragments were purified, inserted into either the PCR-amplified pZE vector containing leuA*BCD and adh6 or the pQE vector by isothermal Gibson assembly, and transformed into XL1-Blue cells. Plasmid DNA was purified (Qiagen, Hilden, Germany) from overnight cultures of antibiotic-resistant colonies and the plasmid sequences were verified (Laragen, Culver City, Calif.).

Chromosomal Gene Knockout.

Genes were removed from the ATCC 98082 ΔrhtA strain genome using P1 transduction from the Keio collection as previously.[32] The aldehyde-alcohol dehydrogenase gene (adhE) was knocked out to eliminate ethanol production from acetyl-coA. In all strains, recA was knocked out to prevent recombination between the genome and plasmids, thereby stabilizing the transformants. Primers used to target recA for knockout were designed based on the Keio collection (Genobase, ecoli.aist-nara.ac.jp) and ordered from Integrated DNA Technologies.

Fermentation Procedure and Analysis.

For n-alcohol production, strains of ST128 were transformed with pZS_thrO, pZAlac_ilvA$_{BS}$leuA, and pZE_LeuA*BCDK*A6 containing various kivd mutations. Fermentation conditions were adapted from those in previous works,[3,4] with the following changes: 20 mL of medium was used, with 100 μg/mL ampicillin, 50 μg/uL kanamycin, and 100 μg/mL spectinomycin added. Cells were grown to an optical density at 600 nm of ~0.6, followed by induction with 0.1 mM isopropyl-b-D-thiogalactoside (IPTG). After fermentation, cells were centrifuged for 15 minutes at 4000×g and 4° C. The supernatant was split into two fractions for analysis, 5 mL for short chain alcohols (ethanol, 1-propanol, and 1-butanol), and 15 mL for long chain alcohols (1-pentanol, 1-hexanol, 1-heptanol, and 1-octanol). Long chain alcohols were extracted from the 15 mL fraction by 3 mL n-hexane prior to analysis. GC-FID analysis was performed as previously described.[4]

Protein Expression, Purification, and Enzymatic Assay of KIVD.

For the native KIVD and KIVD_VLV mutant, 2 ml overnight cultures of XL1B cells were transformed with pQE9 containing N-terminal his-tagged KIVD enzymes and grown in Terrific Broth (BP biomedical, Cat#3046-042) with 50 µg/mL of carbenicillin. (Fisher scientific, Cat# BP2648-5) For the GEOs, 2 ml overnight cultures of BLR cells were transformed with pet29b+ plasmid containing N-terminal his-tagged GEOs, and grown in Terrific Broth with 50 µg/mL of kanamycin. (Fisher scientific, Cat# BP906-5) These cultures were diluted 1:1000 in 500 mL of Terrific Broth with 1 mM $MgSO_4$, 1% glucose, and 50ug/mL of corresponding antibiotics, then grown at 37° C. for 24 hours. Cultures were pelleted down at 4700 rpm for 10 mins and resuspended in auto-induction media (LB broth, 1 mM $MgSO_4$, 0.1 mM TPP, 1×NPS, and 1×5052) for induction at 18° C. for 34 hours. At the end of induction, cells were centrifuged (4700 rpm, 4° C., 20 minutes), supernatant was removed, and cells were resuspended in 40 mL lysis buffer (100 mM Hepes pH 7.5, 100 mM NaCl, 10% glycerol, 0.1 mM TPP, 1 mM $MgSO_4$, 10 mM Imidazole, 1 mM TCEP) and 1 mM PMSF) and sonicated for 2 minutes. Lysed cells were centrifuged at 4700 rpm at 4° C. for 60 mins to remove cell debris. Supernatant was loaded on gravity flow column with 700 µl of cobalt slurry (Fisher scientific, CAT# PI-90091) washed with 10 ml of wash buffer (100 mM Hepes pH 7.5, 100 mM NaCl, 10% glycerol, 0.1 mM TPP, 1 mM $MgSO_4$, 10 mM Imidazole, and 1 mM TCEP). Cobalt bead bed was washed with 15 ml of wash buffer 5 times and proteins were eluted with 1000 µl of elution buffer (100 mM Hepes pH 7.5, 100 mM NaCl, 10% glycerol, 0.1 mM TPP, 1 mM $MgSO_4$, 200 mM Imidazole, and 1 mM TCEP). Protein samples were immediately buffer exchanged with spin concentrators (Satorius, CAT# VS0112) into storage buffer (100 mM Hepes pH 7.5, 100 mM NaCl, 10% glycerol, 0.1 mM TPP, 1 mM $MgSO_4$, and 1 mM TCEP) and stored at 4° C. until kinetics characterization. Protein concentrations were determined using a Synergy H1 spectrophotometer (Biotek) by measuring absorbance at 280 nm using their calculated extinction coefficients with ExPASy ProtParam Tool.[33] All other buffers and salts were purchased from Fisher Scientific unless otherwise specified.

The $k_{cat}$ and $K_M$ values of selective KIVD mutants were measured for the substrates: $C_3$, C5, iso$C_5$, and $C_8$. All substrates were dissolved in MilliQ $H_2O$ and pH was adjusted to 7.5 as necessary. Activity was measured at 0.005 mM to 10 mM substrates. The assay was performed in a 96-well half-area plate. Each reaction contains a final concentration of 0.5 mM NADH, 1 mM DTT, 0.1 mM TPP, 1 mM $MgSO_4$, reaction buffer (100 mM Hepes, 100 mM NaCl, 10% glycerol, pH 7.5) and ADH (Sigma Aldrich, A7011, 10 U/ml for $C_3$, $C_5$ and $C_8$ reactions, 500 U/ml for iso$C_5$ reactions). A wide range of ketoacid decarboxylase concentrations, 4.5 nM-15 µM, were used according to the activity of each enzyme toward different substrates in order to perform steady state kinetics measurement over a period of an hour. Absorbance readings were taken every 1-minute at $OD_{340}$ at 21° C. for 60 minutes using the Synergy H1. Kinetic parameters ($k_{cat}$ and $K_M$) were determined by fitting initial velocity versus substrate concentration data to the Michaelis-Menten equation.

Alcohol Toxicity.

Alcohol tolerance of the in vivo alcohol production strain was evaluated by supplementing the fermentation media with specified quantities of long chain alcohols, and measuring growth over 7 hours. Both the E. coli strain (ATCC 98082 pZS_thrO, pZAlac_ilvA_LeuA, pZE12LeuA*BCDKA6_KIVD_wt) and fermentation media (1×M9 metals+1× trace metal mix+0.5% yeast extract+2% glucose+antibiotics) and conditions are the same as described above (Fermentation procedure and analysis). Cells were grown in media without IPTG-induction to a starting $OD_{600}$ ~0.02 and then supplemented with either 1-petanol, 1-hexanol, 1-heptanol, or 1-octanol at specified concentrations of 10 mg/L, 50 mg/L, 250 mg/L, 500 mg/L, or 1000 mg/L. $OD_{600}$ readings were taken hourly up to 7 hours. FIG. 9 shows the final $OD_{600}$ recorded at 7 hours.

REFERENCES

1. House, US White. "National bioeconomy blueprint." Washington D.C., The White House, April (2012).
2. USDA, US. "Bio-based products: market potential and projections through 2025." *US Department of Agriculture* (2008).
3. Zhang, K., Sawaya, M. R., Eisenberg, D. S., & Liao, J. C. "Expanding metabolism for biosynthesis of non-natural alcohols." *Proceedings of the National Academy of Sciences*, 20653-20658 (2008).
4. Marcheschi, R. J., et al. "A synthetic recursive"+1" pathway for carbon chain elongation." *ACS chemical biology* 7.4, 689-697 (2012).
5. Erickson, B., and Winters P. "Perspective on opportunities in industrial biotechnology in renewable chemicals." *Biotechnology journal* 7.2, 176-185 (2012).
6. Plaza, M., et al. "Biochemical and molecular characterization of α-ketoisovalerate decarboxylase, an enzyme involved in the formation of aldehydes from amino acids by *Lactococcus lactis*." *FEMS microbiology letters* 238.2, 367-374 (2004).
7. Felnagle, E. A., et al. "Engineering synthetic recursive pathways to generate non-natural small molecules." *Nature chemical biology* 8.6, 518-526 (2012).
8. Bayer, Travis S., et al. "Synthesis of methyl halides from biomass using engineered microbes." *Journal of the American Chemical Society.* 6508-6515 (2009).
9. Heins, Richard A., et al. "Phylogenomically guided identification of industrially relevant GH1 β-glucosidases through DNA synthesis and nanostructure-initiator mass spectrometry." *ACS chemical biology.* 2082-2091 (2014).
10. The National Academies. "Industrialization of Biology: A Roadmap to Accelerate Advanced Manufacturing of Chemicals." *The National Academis Press.* (2015)
11. Richter, F., et al. "De novo enzyme design using Rosetta3." *PLoS One* 6.5, e19230 (2011).
12. Finn, Robert D., et al. "Pfam: the protein families database." *Nucleic acids research* (2013).
13. Finn, R. D., Clements J., and Eddy S. R. "HMMER web server: interactive sequence similarity searching." *Nucleic acids research*, gkr367 (2011).
14. Song, Yifan, et al. "High-resolution comparative modeling with RosettaCM." *Structure* 21.10 (2013): 1735-1742.
15. Huang, Y., et al. "CD-HIT Suite: a web server for clustering and comparing biological sequences." *Bioinformatics* 26.5, 680-682 (2010).
16. Zhang, Y., and Skolnick J. "TM-align: a protein structure alignment algorithm based on the TM-score." *Nucleic acids research* 33.7, 2302-2309 (2005).
17. Berthold, Catrine L., et al. "Structure of the branched-chain keto acid decarboxylase (KdcA) from *Lactococcus lactis* provides insights into the structural basis for the chemoselective and enantioselective carboligation reaction." *Acta Crystallographica Section D: Biological Crystallography.* 1217-1224 (2007).
18. Bruning, M., et al. "Structural and Kinetic Studies on Native Intermediates and an Intermediate Analogue in Benzoylformate Decarboxylase Reveal a Least Motion Mechanism with an Unprecedented Short-Lived Predecarboxylation Intermediate‡." *Biochemistry* 48.15, 3258-3268 (2009).
19. Shen, C. R., and Liao J. C. "Metabolic engineering of *Escherichia coli* for 1-butanol and 1-propanol production via the ketoacid pathways." *Metabolic engineering* 10.6, 312-320 (2008).
20. Kell, Douglas B., et al. "Membrane transporter engineering in industrial biotechnology and whole cell biocatalysis." *Trends in biotechnology* (2015).
21. Foo, Jee Loon, et al. "Improving Microbial Biogasoline Production in *Escherichia coli* Using Tolerance Engineering." *mBio* 5.6, e01932-14 (2014).
22. Brennan, Timothy C R, et al. "Alleviating monoterpene toxicity using a two-phase extractive fermentation for the bioproduction of jet fuel mixtures in *Saccharomyces cerevisiae*." *Biotechnology and bioengineering* 2513-2522 (2012).
23. Schnoes, Alexandra M., et al. "Annotation error in public databases: misannotation of molecular function in enzyme superfamilies." *PLoS computational biology* 5.12 (2009).
24. Parekh S. Strain improvement. *Desk encyclopedia of microbiology*. Academic Press, Waltham, (2010).
25. Kearse, M., et al. "Geneious Basic: an integrated and extendable desktop software platform for the organization and analysis of sequence data." *Bioinformatics* 28.12, 1647-1649 (2012).
26. Spartan '08, Wavefunction, Inc. Irvine, Calif. Y. Shao et al. *Phys. Chem. Chem. Phys.*, 3172-3191 (2006).
27. OEChem, version 1.7.7, OpenEye Scientific Software, Inc., Santa Fe, N. Mex., USA, www.eyesopen.com, (2010).
28. Edgar, Robert C. "MUSCLE: multiple sequence alignment with high accuracy and high throughput." *Nucleic acids research* 32.5, 1792-1797 (2004).
29. Letunic, Ivica, and Peer Bork. "Interactive Tree Of Life (iTOL): an online tool for phylogenetic tree display and annotation.", 127-128 *Bioinformatics* 23.1 (2007).
30. Letunic, Ivica, and Peer Bork. "Interactive Tree Of Life v2: online annotation and display of phylogenetic trees made easy." *Nucleic acids research* (2011).
31. Gibson, G. D., et al. "Enzymatic assembly of DNA molecules up to several hundred kilobases." *Nature methods* 6.5, 343-345 (2009).
32. Datsenko, A. K., and Wanner, B. L. "One-step inactivation of chromosomal genes in *Escherichia coli* K-12 using PCR products." Proceedings of the National Academy of Sciences 97.12, 6640-6645 (2000).
33. Gasteiger E., et al. ExPASy: the proteomics server for in-depth protein knowledge and analysis. *Nucleic Acids Res.* 31:3784-3788 (2003).
34. The PyMOL Molecular Graphics System, Version 1.7.4 Schrödinger, LLC.

Program Code and Input

Described herein are various program codes and input that can be utilized in the methods of the present invention for identifying, designing, scoring, and/or characterizing 2-ketoacid decarboxylases of the present invention.

Ligand.pdb

The following exemplary ligand.pdb file contents can be used for calculating Rosetta energy units for ligand:enzyme interactions. The ligand.pdb file can also be used to calculate a ligand binding pocket (e.g., active site) solvent accessible surface area.

| HETATM17213 | C11 | X00 | X | 1 | 20.201 | 113.106 | 7.257 | 1.00 | 0.00 |
|---|---|---|---|---|---|---|---|---|---|
| HETATM17214 | N4 | X00 | X | 1 | 19.791 | 111.778 | 7.282 | 1.00 | 0.00 |
| HETATM17215 | C6 | X00 | X | 1 | 20.602 | 110.614 | 6.899 | 1.00 | 0.00 |
| HETATM17216 | C8 | X00 | X | 1 | 20.906 | 109.687 | 8.079 | 1.00 | 0.00 |
| HETATM17217 | C7 | X00 | X | 1 | 19.941 | 108.811 | 8.567 | 1.00 | 0.00 |
| HETATM17218 | N3 | X00 | X | 1 | 20.229 | 107.980 | 9.634 | 1.00 | 0.00 |
| HETATM17219 | C10 | X00 | X | 1 | 21.458 | 108.021 | 10.258 | 1.00 | 0.00 |
| HETATM17220 | N2 | X00 | X | 1 | 22.411 | 108.875 | 9.787 | 1.00 | 0.00 |
| HETATM17221 | C9 | X00 | X | 1 | 22.160 | 109.704 | 8.707 | 1.00 | 0.00 |
| HETATM17222 | N1 | X00 | X | 1 | 23.154 | 110.476 | 8.289 | 1.00 | 0.00 |
| HETATM17223 | C2 | X00 | X | 1 | 21.726 | 107.127 | 11.428 | 1.00 | 0.00 |
| HETATM17224 | C12 | X00 | X | 1 | 18.500 | 111.725 | 7.696 | 1.00 | 0.00 |
| HETATM17225 | C4 | X00 | X | 1 | 17.701 | 110.455 | 7.838 | 1.00 | 0.00 |
| HETATM17226 | C13 | X00 | X | 1 | 18.045 | 113.015 | 7.978 | 1.00 | 0.00 |
| HETATM17227 | C14 | X00 | X | 1 | 16.677 | 113.426 | 8.453 | 1.00 | 0.00 |
| HETATM17228 | C15 | X00 | X | 1 | 16.683 | 114.488 | 9.549 | 1.00 | 0.00 |
| HETATM17229 | O7 | X00 | X | 1 | 15.322 | 114.843 | 9.716 | 1.00 | 0.00 |
| HETATM17230 | P1 | X00 | X | 1 | 14.842 | 115.976 | 10.759 | 1.00 | 0.00 |
| HETATM17231 | O1 | X00 | X | 1 | 15.535 | 115.665 | 12.077 | 1.00 | 0.00 |
| HETATM17232 | O3 | X00 | X | 1 | 13.339 | 115.886 | 10.849 | 1.00 | 0.00 |
| HETATM17233 | MG1 | X00 | X | 1 | 11.877 | 117.206 | 10.165 | 1.00 | 0.00 |
| HETATM17234 | O6 | X00 | X | 1 | 13.320 | 117.904 | 8.896 | 1.00 | 0.00 |
| HETATM17235 | P2 | X00 | X | 1 | 14.706 | 118.411 | 9.193 | 1.00 | 0.00 |
| HETATM17236 | O2 | X00 | X | 1 | 15.588 | 118.497 | 7.985 | 1.00 | 0.00 |
| HETATM17237 | O4 | X00 | X | 1 | 14.642 | 119.707 | 9.942 | 1.00 | 0.00 |
| HETATM17238 | O5 | X00 | X | 1 | 15.431 | 117.343 | 10.179 | 1.00 | 0.00 |
| HETATM17239 | S1 | X00 | X | 1 | 19.109 | 114.205 | 7.732 | 1.00 | 0.00 |
| HETATM17240 | C17 | X00 | X | 1 | 21.225 | 113.527 | 6.136 | 1.00 | 0.00 |
| HETATM17241 | C16 | X00 | X | 1 | 20.888 | 112.379 | 5.024 | 1.00 | 0.00 |
| HETATM17242 | O8 | X00 | X | 1 | 21.804 | 111.560 | 4.740 | 1.00 | 0.00 |
| HETATM17243 | O9 | X00 | X | 1 | 19.772 | 112.545 | 4.414 | 1.00 | 0.00 |
| HETATM17244 | C18 | X00 | X | 1 | 20.969 | 114.995 | 5.653 | 1.00 | 0.00 |
| HETATM17245 | C1 | X00 | X | 1 | 22.079 | 116.060 | 5.757 | 1.00 | 0.00 |
| HETATM17246 | C19 | X00 | X | 1 | 23.348 | 115.563 | 5.034 | 1.00 | 0.00 |
| HETATM17247 | C20 | X00 | X | 1 | 24.602 | 116.384 | 5.305 | 1.00 | 0.00 |

| | | | | | | | | |
|---|---|---|---|---|---|---|---|---|
| HETATM17248 | C3  | X00 | X | 1 | 24.784 | 116.577 | 6.823  | 1.00 | 0.00 |
| HETATM17249 | C5  | X00 | X | 1 | 24.614 | 115.223 | 7.536  | 1.00 | 0.00 |
| HETATM17250 | O10 | X00 | X | 1 | 22.455 | 113.469 | 6.632  | 1.00 | 0.00 |
| HETATM17251 | H10 | X00 | X | 1 | 20.062 | 110.047 | 6.141  | 1.00 | 0.00 |
| HETATM17252 | H24 | X00 | X | 1 | 21.553 | 110.989 | 6.523  | 1.00 | 0.00 |
| HETATM17253 | H11 | X00 | X | 1 | 18.954 | 108.779 | 8.106  | 1.00 | 0.00 |
| HETATM17254 | H8  | X00 | X | 1 | 23.019 | 111.090 | 7.498  | 1.00 | 0.00 |
| HETATM17255 | H22 | X00 | X | 1 | 24.047 | 110.452 | 8.762  | 1.00 | 0.00 |
| HETATM17256 | H7  | X00 | X | 1 | 21.522 | 106.093 | 11.149 | 1.00 | 0.00 |
| HETATM17257 | H21 | X00 | X | 1 | 22.769 | 107.223 | 11.729 | 1.00 | 0.00 |
| HETATM17258 | H28 | X00 | X | 1 | 21.081 | 107.412 | 12.258 | 1.00 | 0.00 |
| HETATM17259 | H9  | X00 | X | 1 | 17.647 | 110.175 | 8.891  | 1.00 | 0.00 |
| HETATM17260 | H23 | X00 | X | 1 | 16.694 | 110.613 | 7.452  | 1.00 | 0.00 |
| HETATM17261 | H27 | X00 | X | 1 | 18.183 | 109.657 | 7.274  | 1.00 | 0.00 |
| HETATM17262 | H12 | X00 | X | 1 | 16.170 | 112.540 | 8.838  | 1.00 | 0.00 |
| HETATM17263 | H25 | X00 | X | 1 | 16.170 | 113.867 | 7.596  | 1.00 | 0.00 |
| HETATM17264 | H13 | X00 | X | 1 | 17.272 | 115.352 | 9.244  | 1.00 | 0.00 |
| HETATM17265 | H26 | X00 | X | 1 | 17.130 | 114.121 | 10.474 | 1.00 | 0.00 |
| HETATM17266 | H1  | X00 | X | 1 | 20.115 | 115.397 | 6.223  | 1.00 | 0.00 |
| HETATM17267 | H2  | X00 | X | 1 | 20.635 | 114.977 | 4.607  | 1.00 | 0.00 |
| HETATM17268 | H6  | X00 | X | 1 | 22.309 | 116.243 | 6.807  | 1.00 | 0.00 |
| HETATM17269 | H14 | X00 | X | 1 | 21.738 | 116.983 | 5.289  | 1.00 | 0.00 |
| HETATM17270 | H4  | X00 | X | 1 | 23.163 | 115.581 | 3.953  | 1.00 | 0.00 |
| HETATM17271 | H5  | X00 | X | 1 | 23.539 | 114.517 | 5.305  | 1.00 | 0.00 |
| HETATM17272 | H3  | X00 | X | 1 | 24.539 | 117.378 | 4.856  | 1.00 | 0.00 |
| HETATM17273 | H17 | X00 | X | 1 | 25.493 | 115.880 | 4.920  | 1.00 | 0.00 |
| HETATM17274 | H15 | X00 | X | 1 | 24.036 | 117.279 | 7.193  | 1.00 | 0.00 |
| HETATM17275 | H16 | X00 | X | 1 | 25.781 | 116.969 | 7.022  | 1.00 | 0.00 |
| HETATM17276 | H18 | X00 | X | 1 | 24.733 | 115.360 | 8.611  | 1.00 | 0.00 |
| HETATM17277 | H19 | X00 | X | 1 | 25.366 | 114.523 | 7.173  | 1.00 | 0.00 |
| HETATM17278 | H20 | X00 | X | 1 | 23.620 | 114.826 | 7.329  | 1.00 | 0.00 |

Ligand.params

The following exemplary ligand.params file contents can be used for calculating Rosetta energy units for ligand: enzyme interactions. The ligand.pdb file can also be used to calculate a ligand binding pocket (e.g., active site) solvent accessible surface area.

```
NAME X00
IO_STRING X00 Z
TYPE LIGAND
AA UNK
ATOM  C11  CNH2  X   0.54
ATOM  N4   Npro  X  -0.38
ATOM  C6   CH2   X  -0.19
ATOM  C8   aroC  X  -0.13
ATOM  C7   aroC  X  -0.13
ATOM  N3   Nhis  X  -0.54
ATOM  C10  aroC  X  -0.13
ATOM  N2   Nhis  X  -0.54
ATOM  C9   aroC  X  -0.13
ATOM  N1   NH2O  X  -0.48
ATOM  H8   Hpol  X   0.42
ATOM  H22  Hpol  X   0.42
ATOM  C2   CH3   X  -0.28
ATOM  H7   Hapo  X   0.08
ATOM  H21  Hapo  X   0.08
ATOM  H28  Hapo  X   0.08
ATOM  H11  Haro  X   0.10
ATOM  H10  Hapo  X   0.08
ATOM  H24  Hapo  X   0.08
ATOM  C12  COO   X   0.61
ATOM  C4   CH3   X  -0.28
ATOM  H9   Hapo  X   0.08
ATOM  H23  Hapo  X   0.08
ATOM  H27  Hapo  X   0.08
ATOM  C13  COO   X   0.61
ATOM  C14  CH2   X  -0.19
ATOM  C15  CH2   X  -0.19
ATOM  O7   OH    X  -0.67
ATOM  P1   Phos  X   1.49
ATOM  O1   OOC   X  -0.77
ATOM  O3   Oaro  X  -0.67
ATOM  MG1  Mg2p  X   1.99
ATOM  O6   Oaro  X  -0.67
ATOM  P2   Phos  X   1.49
ATOM  O2   OOC   X  -0.77
ATOM  O4   OOC   X  -0.77
```

| | | | | |
|---|---|---|---|---|
| ATOM | O5 | Oaro | X | −0.67 |
| ATOM | H13 | Hapo | X | 0.08 |
| ATOM | H26 | Hapo | X | 0.08 |
| ATOM | H12 | Hapo | X | 0.08 |
| ATOM | H25 | Hapo | X | 0.08 |
| ATOM | S1 | S | X | −0.17 |
| ATOM | C17 | CH1 | X | −0.10 |
| ATOM | C16 | COO | X | 0.61 |
| ATOM | O8 | OOC | X | −0.77 |
| ATOM | O9 | OOC | X | −0.77 |
| ATOM | C18 | CH2 | X | −0.19 |
| ATOM | C1 | CH2 | X | −0.19 |
| ATOM | C19 | CH2 | X | −0.19 |
| ATOM | C20 | CH2 | X | −0.19 |
| ATOM | C3 | CH2 | X | −0.19 |
| ATOM | C5 | CH3 | X | −0.28 |
| ATOM | H18 | Hapo | X | 0.08 |
| ATOM | H19 | Hapo | X | 0.08 |
| ATOM | H20 | Hapo | X | 0.08 |
| ATOM | H15 | Hapo | X | 0.08 |
| ATOM | H16 | Hapo | X | 0.08 |
| ATOM | H3 | Hapo | X | 0.08 |
| ATOM | H17 | Hapo | X | 0.08 |
| ATOM | H4 | Hapo | X | 0.08 |
| ATOM | H5 | Hapo | X | 0.08 |
| ATOM | H6 | Hapo | X | 0.08 |
| ATOM | H14 | Hapo | X | 0.08 |
| ATOM | H1 | Hapo | X | 0.08 |
| ATOM | H2 | Hapo | X | 0.08 |
| ATOM | O10 | OOC | X | −0.77 |
| BOND | N1 | H8 | | |
| BOND | N1 | H22 | | |
| BOND | N2 | C9 | | |
| BOND | N3 | C10 | | |
| BOND | N4 | C6 | | |
| BOND | N4 | C11 | | |
| BOND | C1 | C19 | | |
| BOND | C1 | H6 | | |
| BOND | C1 | H14 | | |
| BOND | C2 | H7 | | |
| BOND | C2 | H21 | | |
| BOND | C2 | H28 | | |
| BOND | C3 | C5 | | |
| BOND | C3 | H15 | | |
| BOND | C3 | H16 | | |
| BOND | C4 | H9 | | |
| BOND | C4 | H23 | | |
| BOND | C4 | H27 | | |
| BOND | C5 | H18 | | |
| BOND | C5 | H19 | | |
| BOND | C5 | H20 | | |
| BOND | C6 | C8 | | |
| BOND | C6 | H10 | | |
| BOND | C6 | H24 | | |
| BOND | C7 | N3 | | |
| BOND | C7 | H11 | | |
| BOND | C8 | C7 | | |
| BOND | C8 | C9 | | |
| BOND | C9 | N1 | | |
| BOND | C10 | N2 | | |
| BOND | C10 | C2 | | |
| BOND | C11 | C17 | | |
| BOND | C11 | S1 | | |
| BOND | C12 | N4 | | |
| BOND | C12 | C4 | | |
| BOND | C13 | C12 | | |
| BOND | C13 | C14 | | |
| BOND | C13 | S1 | | |
| BOND | C14 | C15 | | |
| BOND | C14 | H12 | | |
| BOND | C14 | H25 | | |
| BOND | C15 | O7 | | |
| BOND | C15 | H13 | | |
| BOND | C15 | H26 | | |
| BOND | C16 | O8 | | |
| BOND | C16 | O9 | | |
| BOND | C17 | C16 | | |
| BOND | C17 | C18 | | |
| BOND | C17 | O10 | | |

-continued

| | | | | | | | |
|---|---|---|---|---|---|---|---|
| BOND | C18 | C1 | | | | | |
| BOND | C18 | H1 | | | | | |
| BOND | C18 | H2 | | | | | |
| BOND | C19 | C20 | | | | | |
| BOND | C19 | H4 | | | | | |
| BOND | C19 | H5 | | | | | |
| BOND | C20 | C3 | | | | | |
| BOND | C20 | H3 | | | | | |
| BOND | C20 | H17 | | | | | |
| BOND | O3 | MG1 | | | | | |
| BOND | O6 | P2 | | | | | |
| BOND | O6 | MG1 | | | | | |
| BOND | O7 | P1 | | | | | |
| BOND | P1 | O1 | | | | | |
| BOND | P1 | O3 | | | | | |
| BOND | P1 | O5 | | | | | |
| BOND | P2 | O2 | | | | | |
| BOND | P2 | O4 | | | | | |
| BOND | P2 | O5 | | | | | |
| CHI | 1 | C11 | N4 | C6 | C8 | | |
| CHI | 2 | C18 | C1 | C19 | C20 | | |
| CHI | 3 | N4 | C6 | C8 | C7 | | |
| CHI | 4 | N4 | C11 | C17 | C16 | | |
| CHI | 5 | C12 | C13 | C14 | C15 | | |
| CHI | 6 | C13 | C14 | C15 | O7 | | |
| CHI | 7 | C14 | C15 | O7 | P1 | | |
| CHI | 8 | C11 | C17 | C16 | O8 | | |
| CHI | 9 | C11 | C17 | C18 | C1 | | |
| CHI | 10 | C17 | C18 | C1 | C19 | | |
| CHI | 11 | C1 | C19 | C20 | C3 | | |
| CHI | 12 | C19 | C20 | C3 | C5 | | |
| CHI | 13 | C15 | O7 | P1 | O1 | | |
| NBR_ATOM | C11 | | | | | | |
| NBR_RADIUS | 12.161170 | | | | | | |
| ICOOR_INTERNAL | C11 | 0.000000 | 0.000000 | 0.000000 | C11 | N4 | C6 |
| ICOOR_INTERNAL | N4 | 0.000000 | 180.000000 | 1.391812 | C11 | N4 | C6 |
| ICOOR_INTERNAL | C6 | 0.000000 | 53.916539 | 1.468135 | N4 | C11 | C6 |
| ICOOR_INTERNAL | C8 | 96.000197 | 67.116300 | 1.531771 | C6 | N4 | C11 |
| ICOOR_INTERNAL | C7 | 111.300524 | 59.137106 | 1.391982 | C8 | C6 | N4 |
| ICOOR_INTERNAL | N3 | −179.917537 | 59.736377 | 1.382921 | C7 | C8 | C6 |
| ICOOR_INTERNAL | C10 | 1.618450 | 58.841090 | 1.378822 | N3 | C7 | C8 |
| ICOOR_INTERNAL | N2 | −1.665903 | 61.021480 | 1.364563 | C10 | N3 | C7 |
| ICOOR_INTERNAL | C9 | 0.593863 | 58.813216 | 1.384115 | N2 | C10 | N3 |
| ICOOR_INTERNAL | N1 | −178.163678 | 62.733766 | 1.326764 | C9 | N2 | C10 |
| ICOOR_INTERNAL | H8 | 179.365571 | 60.001398 | 1.010016 | N1 | C9 | N2 |
| ICOOR_INTERNAL | H22 | 179.989152 | 59.997284 | 1.009957 | N1 | C9 | H8 |
| ICOOR_INTERNAL | C2 | −179.539104 | 60.287405 | 1.495790 | C10 | N3 | N2 |
| ICOOR_INTERNAL | H7 | 54.439218 | 70.499071 | 1.089994 | C2 | C10 | N3 |
| ICOOR_INTERNAL | H21 | 120.082237 | 70.494917 | 1.090006 | C2 | C10 | H7 |
| ICOOR_INTERNAL | H28 | 119.957562 | 70.562820 | 1.089996 | C2 | C10 | H21 |
| ICOOR_INTERNAL | H11 | 179.993306 | 60.133454 | 1.089916 | C7 | C8 | N3 |
| ICOOR_INTERNAL | H10 | 120.583822 | 71.350394 | 1.089994 | C6 | N4 | C8 |
| ICOOR_INTERNAL | H24 | 121.121616 | 72.544242 | 1.090009 | C6 | N4 | H10 |
| ICOOR_INTERNAL | C12 | −178.860538 | 71.160846 | 1.356234 | N4 | C11 | C6 |
| ICOOR_INTERNAL | C4 | 179.432481 | 55.532238 | 1.507704 | C12 | N4 | C11 |
| ICOOR_INTERNAL | H9 | 102.069181 | 70.493434 | 1.089997 | C4 | C12 | N4 |
| ICOOR_INTERNAL | H23 | 120.080362 | 70.495628 | 1.090075 | C4 | C12 | H9 |
| ICOOR_INTERNAL | H27 | 119.957609 | 70.556165 | 1.090015 | C4 | C12 | H23 |
| ICOOR_INTERNAL | C13 | 179.339904 | 70.347924 | 1.397384 | C12 | N4 | C4 |
| ICOOR_INTERNAL | C14 | 179.451180 | 52.280217 | 1.504307 | C13 | C12 | N4 |
| ICOOR_INTERNAL | C15 | 117.854883 | 65.606771 | 1.526234 | C14 | C13 | C12 |
| ICOOR_INTERNAL | O7 | −175.865383 | 75.197950 | 1.417354 | C15 | C14 | C13 |
| ICOOR_INTERNAL | P1 | −164.747946 | 57.441505 | 1.612898 | O7 | C15 | C14 |
| ICOOR_INTERNAL | O1 | −43.185207 | 73.683638 | 1.520783 | P1 | O7 | C15 |
| ICOOR_INTERNAL | O3 | −121.006572 | 72.974924 | 1.508629 | P1 | O7 | O1 |
| ICOOR_INTERNAL | MG1 | −110.188590 | 50.123302 | 2.084810 | O3 | P1 | O7 |
| ICOOR_INTERNAL | O6 | 21.371051 | 94.278939 | 2.043304 | MG1 | O3 | P1 |
| ICOOR_INTERNAL | P2 | −54.013740 | 50.009149 | 1.505128 | O6 | MG1 | O3 |
| ICOOR_INTERNAL | O2 | 164.799552 | 66.240624 | 1.498838 | P2 | O6 | MG1 |
| ICOOR_INTERNAL | O4 | 127.318605 | 69.476366 | 1.498457 | P2 | O6 | O2 |
| ICOOR_INTERNAL | O5 | 116.143547 | 71.979188 | 1.624755 | P2 | O6 | O4 |
| ICOOR_INTERNAL | H13 | −119.330756 | 69.335680 | 1.090084 | C15 | C14 | O7 |
| ICOOR_INTERNAL | H26 | −118.726623 | 67.835020 | 1.089992 | C15 | C14 | H13 |
| ICOOR_INTERNAL | H12 | −120.796185 | 71.737001 | 1.089999 | C14 | C13 | C15 |
| ICOOR_INTERNAL | H25 | −121.711373 | 73.431344 | 1.089949 | C14 | C13 | H12 |
| ICOOR_INTERNAL | S1 | −178.555063 | 64.242905 | 1.615075 | C13 | C12 | C14 |
| ICOOR_INTERNAL | C17 | 32.779163 | 62.660465 | 1.575235 | C11 | N4 | C6 |
| ICOOR_INTERNAL | C16 | 73.771627 | 80.628634 | 1.632675 | C17 | C11 | N4 |
| ICOOR_INTERNAL | O8 | −125.893768 | 62.597308 | 1.261160 | C16 | C17 | C11 |

-continued

| | | | | | | | |
|---|---|---|---|---|---|---|---|
| ICOOR_INTERNAL | O9 | −170.771560 | 65.639200 | 1.283554 | C16 | C17 | O8 |
| ICOOR_INTERNAL | C18 | 121.091764 | 68.746111 | 1.567025 | C17 | C11 | C16 |
| ICOOR_INTERNAL | C1 | 159.715274 | 59.432661 | 1.541992 | C18 | C17 | C11 |
| ICOOR_INTERNAL | C19 | −179.885210 | 70.242962 | 1.542018 | C1 | C18 | C17 |
| ICOOR_INTERNAL | C20 | 179.671288 | 65.188952 | 1.523201 | C19 | C1 | C18 |
| ICOOR_INTERNAL | C3 | −179.189402 | 70.082610 | 1.540108 | C20 | C19 | C1 |
| ICOOR_INTERNAL | C5 | −179.841491 | 70.561809 | 1.540037 | C3 | C20 | C19 |
| ICOOR_INTERNAL | H18 | −179.464013 | 70.502707 | 1.090032 | C5 | C3 | C20 |
| ICOOR_INTERNAL | H19 | −120.076286 | 70.498233 | 1.089998 | C5 | C3 | H18 |
| ICOOR_INTERNAL | H20 | −119.965258 | 70.557224 | 1.089971 | C5 | C3 | H19 |
| ICOOR_INTERNAL | H15 | −119.950407 | 70.509198 | 1.090018 | C3 | C20 | C5 |
| ICOOR_INTERNAL | H16 | −120.079178 | 70.498264 | 1.089841 | C3 | C20 | H15 |
| ICOOR_INTERNAL | H3 | −119.086173 | 68.309294 | 1.093502 | C20 | C19 | C3 |
| ICOOR_INTERNAL | H17 | −121.483665 | 68.933404 | 1.094687 | C20 | C19 | H3 |
| ICOOR_INTERNAL | H4 | −120.658650 | 71.441727 | 1.096942 | C19 | C1 | C20 |
| ICOOR_INTERNAL | H5 | −116.222819 | 70.419964 | 1.097278 | C19 | C1 | H4 |
| ICOOR_INTERNAL | H6 | −120.110603 | 70.565925 | 1.090080 | C1 | C18 | C19 |
| ICOOR_INTERNAL | H14 | −120.044272 | 70.701604 | 1.089923 | C1 | C18 | H6 |
| ICOOR_INTERNAL | H1 | −121.585119 | 71.959730 | 1.101515 | C18 | C17 | C1 |
| ICOOR_INTERNAL | H2 | −113.963932 | 70.907736 | 1.098815 | C18 | C17 | H1 |
| ICOOR_INTERNAL | O10 | 118.803514 | 71.041960 | 1.327227 | C17 | C11 | C18 |

SASA.xml

The following exemplary SASA.xml file contents can be used to calculate solvent accessible surface area (SASA) of a 2-ketoacid decarboxylase active site.

```
<ROSETTASCRIPTS>
  <SCOREFXNS>
  </SCOREFXNS>
  <FILTERS>
    <Sasa name=sasa_filter jump=1/>
  </FILTERS>
  <MOVERS>
  </MOVERS>
  <APPLY_TO_POSE>
  </APPLY_TO_POSE>
  <PROTOCOLS>
    <Add filter_name=sasa_filter/>
  </PROTOCOLS>
</ROSETTASCRIPTS>
```

Ligand Energies

Ligand binding energies described herein refer to the transition state substrate that is docked into the active site of a 2-ketoacid decarboxylase in a catalytically relevant conformation and calculated using Rosetta Enzyme Design style constraints. The base energy function is the talaris2013_csts.wts file which contains the following terms: fa_atr fa_rep fa_sol fa_intra_rep fa_elec pro_close hbond_sr_bb hbond_lr_bb hbond_bb_sc hbond_sc dslf_fa13 rama omega fa_dun p_aa_pp ref This base score function can be invoked with the flag:-score:weights Rosetta/main/database/scoring/weights/talaris2013_cst.wts The flag-ligand::old_estat turns the fa_elec term into the hack_elec term.

The flag-enzdes::favor_native_res 2 turns on the res_type_constraint term with a weight of 2.

This results in the final score function of: fa_atr fa_rep fa_sol fa_intra_rep hack_elec pro_close hbond_sr_bb hbond_lr_bb hbond_bb_sc hbond_sc dslf_fa13 rama omega fa_dun p_aa_pp ref res_type_constraint with weights of 0.8 0.44 0.75 0.004 0.7 1 1.17 1.17 1.17 1.1 1 0.2 0.5 0.56 0.32 1 2

The ligand score is weighted sum of this modified talaris 2013 score function.

Solvent Accessible Surface Area (SASA) Calculation

The SASA can be calculated using Rosetta with an input PDB file (the protein structure to score that has a ligand bound in it). The ligand and associated params file in the Rosetta format can be used to instruct the Rosetta program in how to treat and score the ligand. The binding pocket is auto detected. RosettaScripts can be used to run the SASA filter on the input PDB. The score is output in the log file/trace.

In an exemplary embodiment, SASA values are calculated using Rosetta version c2b18f674e7b416b5b756630d7ccd5d64c57512c 2015-05-04 14:47:46-0700 from git@github.com:RosettaCommons/main.git. This version can be used for any of the Rosetta functions described herein (e.g., enzyme design, homology modeling, docking, energy function evaluation, etc.).

The SASA score can be calculated using the following command line input: ~/Rosetta/main/source/bin/rosetta_scripts.default.macosclangrelease-database ~/Rosetta/main/database-parser:protocol sasa.xml-s input.pdb-extra_res_fa ligand.params.

What is claimed is:

1. An enzyme comprising 2-ketoacid decarboxylase activity, wherein the enzyme comprises:
   a 3-layer alpha-beta-alpha sandwich;
   a thiamine pyrophosphate (TPP) binding pocket; and
   at least a 100-fold greater catalytic efficiency for C8 2-ketoacid substrates as compared to C3 or isoC5 2-ketoacid substrates, wherein the catalytic efficiency is measured by kcat/Km,
   the primary amino acid sequence of the enzyme differs from the primary amino acid sequence of SEQ ID NO: 1 or SEQ ID NO:2 at least at an amino acid residue within 8 Å of a 2-ketoacid decarboxylase active site of the enzyme; wherein
   the 2-ketoacid decarboxylase active site comprises amino acids corresponding to amino acid positions 23-27, 50, 51, 56, 71, 75, 76, 79, 82, 112, 114, 287, 356, 373-377, 379, 394, 396-399, 423-428, 430, 450-458, 461, and 535 of SEQ ID NO:1; and wherein
   the enzyme comprises mutations corresponding to G402V, M538L, and F542V of SEQ ID NO:1.

2. The enzyme of claim 1, wherein the enzyme has a template modeling (TM) align score against the structure file (PDB) ID:2VBG of at least 0.5.

3. The modified enzyme of claim 1, wherein the enzyme has a Cα root mean squared deviation of less than 1 Å over at least 100 structurally aligned residues as compared against PDB ID:2VBG.

4. The enzyme of claim 1, wherein the ratio of kcal/Km against C8 2-ketoacid substrates over the heat/Km against isoC5 2-ketoacid substrates is at least 50-fold greater than the native enzyme.

5. The enzyme of claim 1, wherein the enzyme comprises a substrate binding pocket with a solvent accessible surface area of at least 7500 Å.

* * * * *

SEQUENCE LISTING

<160> NUMBER OF SEQ ID NOS: 40

<210> SEQ ID NO 1
<211> LENGTH: 548
<212> TYPE: PRT
<213> ORGANISM: Lactococcus lactis

<400> SEQUENCE: 1

Met Tyr Thr Val Gly Asp Tyr Leu Leu Asp Arg Leu His Glu Leu Gly

```
1               5                   10                  15
Ile Glu Glu Ile Phe Gly Val Pro Gly Asp Tyr Asn Leu Gln Phe Leu
                20                  25                  30

Asp Gln Ile Ile Ser Arg Lys Asp Met Lys Trp Val Gly Asn Ala Asn
                35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
                130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
                210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
                290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
                370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430
```

```
Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
530                 535                 540

Gln Asn Lys Ser
545

<210> SEQ ID NO 2
<211> LENGTH: 536
<212> TYPE: PRT
<213> ORGANISM: Streptomyces sp. C

<400> SEQUENCE: 2

Met Arg Thr Val Arg Glu Ser Ala Leu Asp Val Leu Arg Ala Arg Gly
1               5                  10                  15

Met Thr Thr Val Phe Gly Asn Pro Gly Ser Thr Glu Leu Pro Met Leu
            20                  25                  30

Lys Gln Phe Pro Asp Asp Phe Arg Tyr Val Leu Gly Leu Gln Glu Ala
        35                  40                  45

Val Val Val Gly Met Ala Asp Gly Phe Ala Leu Ala Ser Gly Thr Thr
    50                  55                  60

Gly Leu Val Asn Leu His Thr Gly Pro Gly Thr Gly Asn Ala Met Gly
65                  70                  75                  80

Ala Ile Leu Asn Ala Arg Ala Asn Arg Thr Pro Met Val Val Thr Ala
                85                  90                  95

Gly Gln Gln Val Arg Ala Met Leu Thr Met Glu Ala Leu Leu Thr Asn
            100                 105                 110

Pro Gln Ser Thr Leu Leu Pro Gln Pro Ala Val Lys Trp Ala Tyr Glu
        115                 120                 125

Pro Pro Arg Ala Ala Asp Val Ala Pro Leu Ala Arg Ala Val Gln
130                 135                 140

Val Ala Glu Thr Pro Pro Gln Gly Pro Val Phe Val Ser Leu Pro Met
145                 150                 155                 160

Asp Asp Phe Asp Val Val Leu Gly Glu Asp Glu Asp Arg Ala Ala Gln
                165                 170                 175

Arg Ala Ala Ala Arg Thr Val Thr His Ala Ala Pro Ser Ala Glu
            180                 185                 190

Val Val Arg Arg Leu Ala Ala Arg Leu Ser Gly Ala Arg Ser Ala Val
        195                 200                 205

Leu Val Ala Gly Asn Asp Val Asp Ala Ser Gly Ala Trp Asp Ala Val
    210                 215                 220

Val Glu Leu Ala Glu Arg Thr Gly Leu Pro Val Trp Ser Ala Pro Thr
225                 230                 235                 240

Glu Gly Arg Val Ala Phe Pro Lys Ser His Pro Gln Tyr Arg Gly Met
```

```
                    245                 250                 255
Leu Pro Pro Ala Ile Ala Pro Leu Ser Arg Cys Leu Glu Gly His Asp
                260                 265                 270
Leu Val Leu Val Ile Gly Ala Pro Val Phe Cys Tyr Tyr Pro Tyr Val
            275                 280                 285
Pro Gly Ala His Leu Pro Glu Asn Thr Glu Leu Val His Leu Thr Arg
        290                 295                 300
Asp Ala Asp Glu Ala Ala Arg Ala Pro Val Gly Asp Ala Val Val Ala
305                 310                 315                 320
Asp Leu Ala Leu Thr Val Arg Ala Leu Leu Ala Glu Leu Pro Ala Arg
                325                 330                 335
Glu Ala Ala Pro Ala Ala Arg Thr Ala Arg Ala Glu Ser Thr Ala
                340                 345                 350
Glu Val Asp Gly Val Leu Thr Pro Leu Ala Ala Met Thr Ala Ile Ala
            355                 360                 365
Gln Gly Ala Pro Ala Asn Thr Leu Trp Val Asn Glu Ser Pro Ser Asn
        370                 375                 380
Leu Gly Gln Phe His Asp Ala Thr Arg Ile Asp Thr Pro Gly Ser Phe
385                 390                 395                 400
Leu Phe Thr Ala Gly Gly Leu Gly Phe Gly Leu Ala Ala Val
                405                 410                 415
Gly Ala Gln Leu Gly Ala Pro Asp Arg Pro Val Val Cys Val Ile Gly
                420                 425                 430
Asp Gly Ser Thr His Tyr Ala Val Gln Ala Leu Trp Thr Ala Ala
                435                 440                 445
Tyr Lys Val Pro Val Thr Phe Val Val Leu Ser Asn Gln Arg Tyr Ala
        450                 455                 460
Ile Leu Gln Trp Phe Ala Gln Val Glu Gly Ala Gln Gly Ala Pro Gly
465                 470                 475                 480
Leu Asp Ile Pro Gly Leu Asp Ile Ala Ala Val Ala Thr Gly Tyr Gly
                485                 490                 495
Val Arg Ala His Arg Ala Thr Gly Phe Gly Glu Leu Ser Lys Leu Val
                500                 505                 510
Arg Glu Ser Ala Leu Gln Gln Asp Gly Pro Val Leu Ile Asp Val Pro
        515                 520                 525
Val Thr Thr Glu Leu Pro Thr Leu
        530                 535

<210> SEQ ID NO 3
<211> LENGTH: 548
<212> TYPE: PRT
<213> ORGANISM: Artificial Sequence
<220> FEATURE:
<223> OTHER INFORMATION: Synthetic protein KIVD_VLV

<400> SEQUENCE: 3

Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
            20                  25                  30
Asp Gln Ile Ile Ser Arg Lys Asp Met Lys Trp Val Gly Asn Ala Asn
        35                  40                  45
Glu Leu Asn Ala Ser Tyr Met Ala Asp Gly Tyr Ala Arg Thr Lys Lys
    50                  55                  60
Ala Ala Ala Phe Leu Thr Thr Phe Gly Val Gly Glu Leu Ser Ala Val
```

```
                65                  70                  75                  80
Asn Gly Leu Ala Gly Ser Tyr Ala Glu Asn Leu Pro Val Val Glu Ile
                        85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
            130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Val Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495
```

```
Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Leu Gly Lys Leu Val Ala Glu
    530                 535                 540

Gln Asn Lys Ser
545

<210> SEQ ID NO 4
<211> LENGTH: 570
<212> TYPE: PRT
<213> ORGANISM: Schizosaccaromyces pombe

<400> SEQUENCE: 4

Met Ser Ser Glu Lys Val Leu Val Gly Glu Tyr Leu Phe Thr Arg Leu
1               5                   10                  15

Leu Gln Leu Gly Ile Lys Ser Ile Leu Gly Val Pro Gly Asp Phe Asn
            20                  25                  30

Leu Ala Leu Leu Asp Leu Ile Glu Lys Val Gly Asp Glu Thr Phe Arg
        35                  40                  45

Trp Val Gly Asn Glu Asn Glu Leu Asn Gly Ala Tyr Ala Ala Asp Ala
    50                  55                  60

Tyr Ala Arg Val Lys Gly Ile Ser Ala Ile Val Thr Thr Phe Gly Val
65                  70                  75                  80

Gly Glu Leu Ser Ala Leu Asn Gly Phe Ala Gly Ala Tyr Ser Glu Arg
                85                  90                  95

Ile Pro Val Val His Ile Val Gly Val Pro Asn Thr Lys Ala Gln Ala
            100                 105                 110

Thr Arg Pro Leu Leu His His Thr Leu Gly Asn Gly Asp Phe Lys Val
        115                 120                 125

Phe Gln Arg Met Ser Ser Glu Leu Ser Ala Asp Val Ala Phe Leu Asp
    130                 135                 140

Ser Gly Asp Ser Ala Gly Arg Leu Ile Asp Asn Leu Leu Glu Thr Cys
145                 150                 155                 160

Val Arg Thr Ser Arg Pro Val Tyr Leu Ala Val Pro Ser Asp Ala Gly
                165                 170                 175

Tyr Phe Tyr Thr Asp Ala Ser Pro Leu Lys Thr Pro Leu Val Phe Pro
            180                 185                 190

Val Pro Glu Asn Asn Lys Glu Ile Glu His Glu Val Val Ser Glu Ile
        195                 200                 205

Leu Glu Leu Ile Glu Lys Ser Lys Asn Pro Ser Ile Leu Val Asp Ala
    210                 215                 220

Cys Val Ser Arg Phe His Ile Gln Gln Glu Thr Gln Asp Phe Ile Asp
225                 230                 235                 240

Ala Thr His Phe Pro Thr Tyr Val Thr Pro Met Gly Lys Thr Ala Ile
                245                 250                 255

Asn Glu Ser Ser Pro Tyr Phe Asp Gly Val Tyr Ile Gly Ser Leu Thr
            260                 265                 270

Glu Pro Ser Ile Lys Glu Arg Ala Glu Ser Thr Asp Leu Leu Leu Ile
        275                 280                 285

Ile Gly Gly Leu Arg Ser Asp Phe Asn Ser Gly Thr Phe Thr Tyr Ala
    290                 295                 300

Thr Pro Ala Ser Gln Thr Ile Glu Phe His Ser Asp Tyr Thr Lys Ile
```

```
                    305                 310                 315                 320
Arg Ser Gly Val Tyr Glu Gly Ile Ser Met Lys His Leu Leu Pro Lys
                325                 330                 335

Leu Thr Ala Ala Ile Asp Lys Lys Ser Val Gln Ala Lys Ala Arg Pro
                340                 345                 350

Val His Phe Glu Pro Pro Lys Ala Val Ala Ala Glu Gly Tyr Ala Glu
                355                 360                 365

Gly Thr Ile Thr His Lys Trp Phe Trp Pro Thr Phe Ala Ser Phe Leu
            370                 375                 380

Arg Glu Ser Asp Val Val Thr Thr Glu Thr Gly Thr Ser Asn Phe Gly
385                 390                 395                 400

Ile Leu Asp Cys Ile Phe Pro Lys Gly Cys Gln Asn Leu Ser Gln Val
                405                 410                 415

Leu Trp Gly Ser Ile Gly Trp Ser Val Gly Ala Met Phe Gly Ala Thr
                420                 425                 430

Leu Gly Ile Lys Asp Ser Asp Ala Pro His Arg Arg Ser Ile Leu Ile
            435                 440                 445

Val Gly Asp Gly Ser Leu His Leu Thr Val Gln Glu Ile Ser Ala Thr
450                 455                 460

Ile Arg Asn Gly Leu Thr Pro Ile Ile Phe Val Ile Asn Asn Lys Gly
465                 470                 475                 480

Tyr Thr Ile Glu Arg Leu Ile His Gly Leu His Ala Val Tyr Asn Asp
                485                 490                 495

Ile Asn Thr Glu Trp Asp Tyr Gln Asn Leu Leu Lys Gly Tyr Gly Ala
                500                 505                 510

Lys Asn Ser Arg Ser Tyr Asn Ile His Ser Glu Lys Glu Leu Leu Asp
            515                 520                 525

Leu Phe Lys Asp Glu Glu Phe Gly Lys Ala Asp Val Ile Gln Leu Val
                530                 535                 540

Glu Val His Met Pro Val Leu Asp Ala Pro Arg Val Leu Ile Glu Gln
545                 550                 555                 560

Ala Lys Leu Thr Ala Ser Leu Asn Lys Gln
                565                 570

<210> SEQ ID NO 5
<211> LENGTH: 574
<212> TYPE: PRT
<213> ORGANISM: Unknown
<220> FEATURE:
<223> OTHER INFORMATION: Bacterial

<400> SEQUENCE: 5

Met Glu Leu Leu Ser Gly Gly Glu Met Leu Val Arg Ala Leu Ala Asp
1               5                   10                  15

Glu Gly Val Glu His Val Phe Gly Tyr Pro Gly Gly Ala Val Leu His
                20                  25                  30

Ile Tyr Asp Ala Leu Phe Gln Gln Asp Lys Ile Asn His Tyr Leu Val
            35                  40                  45

Arg His Glu Gln Ala Ala Gly His Met Ala Asp Ala Tyr Ser Arg Ala
50                  55                  60

Thr Gly Lys Thr Gly Val Val Leu Val Thr Ser Gly Pro Gly Ala Thr
65                  70                  75                  80

Asn Thr Val Thr Pro Ile Ala Thr Ala Tyr Met Asp Ser Ile Pro Met
                85                  90                  95

Val Ile Leu Ser Gly Gln Val Ala Ser His Leu Ile Gly Glu Asp Ala
```

-continued

```
                100                 105                 110
    Phe Gln Glu Thr Asp Met Val Gly Ile Ser Arg Pro Ile Val Lys His
            115                 120                 125

Ser Phe Gln Val Arg His Ala Ser Glu Ile Pro Ala Ile Ile Lys Lys
        130                 135                 140

Ala Phe Tyr Ile Ala Ala Ser Gly Arg Pro Gly Pro Val Val Val Asp
    145                 150                 155                 160

Ile Pro Lys Asp Ala Thr Asn Pro Ala Glu Lys Phe Ala Tyr Glu Tyr
                    165                 170                 175

Pro Glu Lys Val Lys Met Arg Ser Tyr Gln Pro Pro Ser Arg Gly His
                180                 185                 190

Ser Gly Gln Ile Arg Lys Ala Ile Asp Glu Leu Leu Ser Ala Lys Arg
            195                 200                 205

Pro Val Ile Tyr Thr Gly Gly Val Val Gln Gly Asn Ala Ser Ala
        210                 215                 220

Leu Leu Thr Glu Leu Ala His Leu Leu Gly Tyr Pro Val Thr Asn Thr
    225                 230                 235                 240

Leu Met Gly Leu Gly Gly Phe Pro Gly Asp Asp Pro Gln Phe Val Gly
                    245                 250                 255

Met Leu Gly Met His Gly Thr Tyr Glu Ala Asn Met Ala Met His Asn
                260                 265                 270

Ala Asp Val Ile Leu Ala Ile Gly Ala Arg Phe Asp Asp Arg Val Thr
            275                 280                 285

Asn Asn Pro Ala Lys Phe Cys Val Asn Ala Lys Val Ile His Ile Asp
        290                 295                 300

Ile Asp Pro Ala Ser Ile Ser Lys Thr Ile Met Ala His Ile Pro Ile
    305                 310                 315                 320

Val Gly Ala Val Glu Pro Val Leu Gln Glu Met Leu Thr Gln Leu Lys
                    325                 330                 335

Gln Leu Asn Val Ser Lys Pro Asn Pro Glu Ala Ile Ala Ala Trp Trp
                340                 345                 350

Asp Gln Ile Asn Glu Trp Arg Lys Val His Gly Leu Lys Phe Glu Thr
            355                 360                 365

Pro Thr Asp Gly Thr Met Lys Pro Gln Gln Val Val Glu Ala Leu Tyr
        370                 375                 380

Lys Ala Thr Asn Gly Asp Ala Ile Ile Thr Ser Asp Val Gly Gln His
    385                 390                 395                 400

Gln Met Phe Gly Ala Leu Tyr Tyr Lys Tyr Lys Arg Pro Arg Gln Trp
                    405                 410                 415

Ile Asn Ser Gly Gly Leu Gly Thr Met Gly Val Gly Leu Pro Tyr Ala
                420                 425                 430

Met Ala Ala Lys Leu Ala Phe Pro Asp Gln Gln Val Val Cys Ile Thr
            435                 440                 445

Gly Glu Ala Ser Ile Gln Met Cys Ile Gln Glu Leu Ser Thr Cys Lys
        450                 455                 460

Gln Tyr Gly Met Asn Val Lys Ile Leu Cys Leu Asn Asn Arg Ala Leu
    465                 470                 475                 480

Gly Met Val Lys Gln Trp Gln Asp Met Asn Tyr Glu Gly Arg His Ser
                    485                 490                 495

Ser Ser Tyr Val Glu Ser Leu Pro Asp Phe Gly Lys Leu Met Glu Ala
                500                 505                 510

Tyr Gly His Val Gly Ile Gln Ile Asp His Ala Asp Glu Leu Glu Ser
            515                 520                 525
```

-continued

Lys Leu Ala Glu Ala Met Ala Ile Asn Asp Lys Cys Val Phe Ile Asn
530                 535                 540

Val Met Val Asp Arg Thr Glu His Val Tyr Pro Met Leu Ile Ala Gly
545                 550                 555                 560

Gln Ser Met Lys Asp Met Trp Leu Gly Lys Gly Glu Arg Thr
                565                 570

<210> SEQ ID NO 6
<211> LENGTH: 538
<212> TYPE: PRT
<213> ORGANISM: Comamonas testosteroni

<400> SEQUENCE: 6

Met Pro Ala Asn Thr Ala Pro Asn Ala Gln Ala Ala Glu Val Phe Thr
1               5                   10                  15

Val Arg His Ala Val Ile Asn Met Leu Arg Glu Leu Gly Met Thr Arg
                20                  25                  30

Ile Phe Gly Asn Pro Gly Ser Thr Glu Leu Pro Leu Phe Arg Asp Tyr
            35                  40                  45

Pro Glu Asp Phe Ser Tyr Ile Leu Gly Leu Gln Glu Thr Val Val Val
50                  55                  60

Gly Met Ala Asp Gly Tyr Ala Gln Ala Thr Arg Asn Ala Ser Phe Val
65                  70                  75                  80

Asn Leu His Ser Ala Ala Gly Val Gly His Ala Met Ala Asn Ile Phe
                85                  90                  95

Thr Ala Phe Lys Asn Arg Thr Pro Met Val Ile Thr Ala Gly Gln Gln
            100                 105                 110

Thr Arg Ser Leu Leu Gln Phe Asp Pro Phe Leu His Ser Asn Gln Ala
        115                 120                 125

Ala Glu Leu Pro Lys Pro Tyr Val Lys Trp Ser Cys Glu Pro Ala Arg
130                 135                 140

Ala Glu Asp Val Pro Gln Ala Leu Ala Arg Ala Tyr Tyr Ile Ala Met
145                 150                 155                 160

Gln Glu Pro Arg Gly Pro Val Phe Val Ser Ile Pro Ala Asp Asp Trp
                165                 170                 175

Asp Val Pro Cys Glu Pro Ile Thr Leu Arg Lys Val Gly Phe Glu Thr
            180                 185                 190

Arg Pro Asp Pro Arg Leu Leu Asp Ser Ile Gly Gln Ala Leu Glu Gly
        195                 200                 205

Ala Arg Ala Pro Ala Phe Val Val Gly Ala Ala Val Asp Arg Ser Gln
210                 215                 220

Ala Phe Glu Ala Val Gln Ala Leu Ala Glu Arg His Gln Ala Arg Val
225                 230                 235                 240

Tyr Val Ala Pro Met Ser Gly Arg Cys Gly Phe Pro Glu Asp His Ala
                245                 250                 255

Leu Phe Gly Gly Phe Leu Pro Ala Met Arg Glu Arg Ile Val Asp Arg
            260                 265                 270

Leu Ser Gly His Asp Val Val Phe Val Ile Gly Ala Pro Ala Phe Thr
        275                 280                 285

Tyr His Val Glu Gly His Gly Pro Phe Ile Ala Glu Gly Thr Gln Leu
        290                 295                 300

Phe Gln Leu Ile Glu Asp Pro Ala Ile Ala Ala Trp Ala Pro Val Gly
305                 310                 315                 320

Asp Ala Ala Val Gly Asn Ile Arg Met Gly Val Gln Glu Leu Leu Ala

```
                    325                 330                 335
Arg Pro Leu Thr His Pro Arg Pro Ala Leu Gln Pro Arg Pro Ala Ile
                340                 345                 350

Pro Ala Pro Ala Ala Pro Glu Pro Gly Arg Leu Met Thr Asp Ala Phe
            355                 360                 365

Leu Met His Thr Leu Ala Gln Val Arg Ser Arg Asp Ser Ile Ile Val
        370                 375                 380

Glu Glu Ala Pro Gly Ser Arg Ser Ile Ile Gln Ala His Leu Pro Ile
385                 390                 395                 400

Tyr Ala Ala Glu Thr Phe Phe Thr Met Cys Ser Gly Gly Leu Gly His
                405                 410                 415

Ser Leu Pro Ala Ser Val Gly Ile Ala Leu Ala Arg Pro Asp Lys Lys
            420                 425                 430

Val Ile Gly Val Ile Gly Asp Gly Ser Ala Met Tyr Ala Ile Gln Ala
        435                 440                 445

Leu Trp Ser Ala Ala His Leu Lys Leu Pro Val Thr Tyr Ile Ile Val
    450                 455                 460

Lys Asn Arg Arg Tyr Ala Ala Leu Gln Asp Phe Ser Arg Val Phe Gly
465                 470                 475                 480

Tyr Arg Glu Gly Glu Lys Val Glu Gly Thr Asp Leu Pro Asp Ile Asp
                485                 490                 495

Phe Val Ala Leu Ala Lys Gly Gln Gly Cys Asp Gly Val Arg Val Thr
            500                 505                 510

Asp Ala Ala Gln Leu Ser Gln Val Leu Arg Asp Ala Leu Arg Ser Pro
        515                 520                 525

Arg Ala Thr Leu Val Glu Val Glu Val Ala
    530                 535

<210> SEQ ID NO 7
<211> LENGTH: 548
<212> TYPE: PRT
<213> ORGANISM: Enterococcus moraviensis

<400> SEQUENCE: 7

Met Tyr Thr Val Ala Asp Tyr Leu Leu Asp Arg Leu Lys Glu Leu Gly
1               5                   10                  15

Ile Asp Glu Val Phe Gly Val Pro Gly Asp Tyr Asn Leu Gln Phe Leu
            20                  25                  30

Asp His Ile Thr Ala Arg Lys Asp Leu Glu Trp Ile Gly Asn Ala Asn
        35                  40                  45

Glu Leu Asn Ala Ala Tyr Met Ala Asp Gly Tyr Ala Arg Thr Lys Gly
    50                  55                  60

Ile Ser Ala Leu Val Thr Thr Phe Gly Val Gly Glu Leu Ser Ala Ile
65                  70                  75                  80

Asn Gly Leu Ala Gly Ser Tyr Ala Glu Ser Ile Pro Val Ile Glu Ile
                85                  90                  95

Val Gly Ser Pro Thr Thr Thr Val Gln Gln Asn Lys Lys Leu Val His
            100                 105                 110

His Thr Leu Gly Asp Gly Asp Phe Leu Arg Phe Glu Arg Ile His Glu
        115                 120                 125

Glu Val Ser Ala Ala Ile Ala His Leu Ser Thr Glu Asn Ala Pro Ser
    130                 135                 140

Glu Ile Asp Arg Val Leu Thr Val Ala Met Thr Glu Lys Arg Pro Val
145                 150                 155                 160
```

```
Tyr Ile Asn Leu Pro Ile Asp Ile Ala Glu Met Lys Ala Ser Ala Pro
            165                 170                 175

Thr Thr Pro Leu Asn His Thr Thr Asp Gln Leu Thr Thr Val Glu Thr
        180                 185                 190

Ala Ile Leu Thr Lys Val Glu Asp Ala Leu Lys Gln Ser Lys Asn Pro
    195                 200                 205

Val Val Ile Ala Gly His Glu Ile Leu Ser Tyr His Ile Glu Asn Gln
210                 215                 220

Leu Glu Gln Phe Ile Gln Lys Phe Asn Leu Pro Ile Thr Val Leu Pro
225                 230                 235                 240

Phe Gly Lys Gly Ala Phe Asn Glu Glu Asp Ala His Tyr Leu Gly Thr
                245                 250                 255

Tyr Thr Gly Ser Thr Thr Asp Glu Ser Met Lys Asn Arg Val Asp His
            260                 265                 270

Ala Asp Leu Val Leu Leu Gly Ala Lys Leu Thr Asp Ser Ala Thr
        275                 280                 285

Ser Gly Phe Ser Phe Gly Phe Thr Glu Lys Gln Met Ile Ser Ile Gly
    290                 295                 300

Ser Thr Glu Val Leu Phe Tyr Gly Glu Lys Gln Glu Thr Val Gln Leu
305                 310                 315                 320

Asp Arg Phe Val Ser Ala Leu Ser Thr Leu Ser Phe Ser Arg Phe Thr
                325                 330                 335

Asp Glu Met Pro Ser Val Lys Arg Leu Ala Thr Pro Lys Val Arg Asp
            340                 345                 350

Glu Lys Leu Thr Gln Lys Gln Phe Trp Gln Met Val Glu Ser Phe Leu
        355                 360                 365

Leu Gln Gly Asp Thr Val Val Gly Glu Gln Gly Thr Ser Phe Phe Gly
370                 375                 380

Leu Thr Asn Val Pro Leu Lys Lys Asp Met His Phe Ile Gly Gln Pro
385                 390                 395                 400

Leu Trp Gly Ser Ile Gly Tyr Thr Phe Pro Ser Ala Leu Gly Ser Gln
                405                 410                 415

Ile Ala Asn Lys Glu Ser Arg His Leu Leu Phe Ile Gly Asp Gly Ser
            420                 425                 430

Leu Gln Leu Thr Val Gln Glu Leu Gly Thr Ala Ile Arg Glu Lys Leu
        435                 440                 445

Thr Pro Ile Val Phe Val Ile Asn Asn Asn Gly Tyr Thr Val Glu Arg
        450                 455                 460

Glu Ile His Gly Ala Thr Glu Gln Tyr Asn Asp Ile Pro Met Trp Asp
465                 470                 475                 480

Tyr Gln Lys Leu Pro Phe Val Phe Gly Gly Thr Asp Gln Thr Val Ala
                485                 490                 495

Thr Tyr Lys Val Ser Thr Glu Ile Glu Leu Asp Asn Ala Met Thr Arg
            500                 505                 510

Ala Arg Thr Asp Val Asp Arg Leu Gln Trp Ile Glu Val Val Met Asp
        515                 520                 525

Gln Asn Asp Ala Pro Val Leu Leu Lys Lys Leu Ala Lys Ile Phe Ala
530                 535                 540

Lys Gln Asn Ser
545

<210> SEQ ID NO 8
<211> LENGTH: 559
<212> TYPE: PRT
```

-continued

<213> ORGANISM: Streptomyces sp. HmicA12

<400> SEQUENCE: 8

```
Met Val Ser Arg Pro Ala Arg Val Ala Ile Leu Glu Gln Leu Arg Ala
1               5                   10                  15

Asp Gly Val Arg Tyr Met Phe Gly Asn Pro Gly Thr Val Glu Gln Gly
            20                  25                  30

Phe Leu Asp Glu Leu Arg Asn Phe Pro Asp Ile Glu Tyr Ile Leu Ala
        35                  40                  45

Leu Gln Glu Ala Gly Val Val Gly Leu Ala Asp Gly Tyr Ala Arg Ala
    50                  55                  60

Thr Arg Thr Pro Ala Val Leu Gln Leu His Thr Gly Val Gly Val Gly
65                  70                  75                  80

Asn Ala Val Gly Met Leu Tyr Gln Ala Lys Arg Gly His Ala Pro Leu
                85                  90                  95

Val Ala Ile Ala Gly Glu Ala Gly Leu Arg Tyr Asp Ala Met Glu Ala
            100                 105                 110

Gln Met Ala Val Asp Leu Val Ala Met Ala Glu Pro Val Thr Lys Trp
        115                 120                 125

Ala Thr Arg Val Val Asp Pro Glu Ser Thr Leu Arg Val Leu Arg Arg
    130                 135                 140

Ala Met Lys Val Ala Ala Thr Pro Pro Tyr Gly Pro Val Leu Val Val
145                 150                 155                 160

Leu Pro Ala Asp Val Met Asp Arg Asp Thr Ser Glu Ala Ala Val Pro
                165                 170                 175

Thr Ser Tyr Val Asp Phe Ala Ala Thr Pro Asp Pro Gln Val Leu Asp
            180                 185                 190

Arg Ala Ala Glu Leu Leu Ala Gly Ala Glu Arg Pro Ile Val Ile Ala
        195                 200                 205

Gly Asp Gly Val His Phe Ala Gly Ala Gln Glu Glu Leu Gly Arg Leu
    210                 215                 220

Ala Gln Thr Trp Gly Ala Glu Val Trp Gly Ala Asp Trp Ala Glu Val
225                 230                 235                 240

Asn Leu Ser Val Glu His Pro Ala Tyr Ala Gly Gln Leu Gly His Met
                245                 250                 255

Phe Gly Asp Ser Ser Arg Arg Val Thr Gly Ala Ala Asp Ala Val Leu
            260                 265                 270

Leu Val Gly Thr Tyr Ala Leu Pro Glu Val Tyr Pro Ala Leu Asp Gly
        275                 280                 285

Val Phe Ala Asp Gly Ala Pro Val Val His Ile Asp Leu Asp Thr Asp
    290                 295                 300

Ala Ile Ala Lys Asn Phe Pro Val Asp Leu Gly Leu Ala Leu Ala Asp Pro
305                 310                 315                 320

Arg Arg Ala Leu Asp Gly Leu Ala Arg Ala Leu Glu Arg Arg Met Ser
                325                 330                 335

Pro Glu Ser Arg Ala Arg Ala Gly Glu Trp Phe Thr Gly Arg Ser Ala
            340                 345                 350

Gln Arg Ser Tyr Glu Ile Ala Ala Ala Arg Glu Gln Asp Glu Ala Ala
        355                 360                 365

Leu Ala Pro Asp Ala Leu Pro Val Thr Ala Phe Leu Gln Glu Leu Ala
    370                 375                 380

Arg Gln Leu Pro Glu Asp Ala Val Phe Asp Glu Ala Leu Thr Ala
385                 390                 395                 400
```

-continued

```
Ser Pro Asp Val Thr Arg His Leu Pro Pro Thr Arg Pro Gly His Trp
            405                 410                 415

His Gln Thr Arg Gly Gly Ser Leu Gly Val Gly Ile Pro Gly Ala Ile
        420                 425                 430

Ala Ala Gln Leu Ala His Pro Asp Arg Thr Val Val Gly Phe Thr Gly
    435                 440                 445

Asp Gly Gly Ser Leu Tyr Thr Ile Gln Ala Leu Trp Thr Ala Ala Arg
450                 455                 460

Tyr Asp Ile Gly Ala Thr Phe Val Ile Cys Asn Asn Ser Ser Tyr Lys
465                 470                 475                 480

Leu Leu Glu Leu Asn Ile Glu Glu Tyr Trp Lys Ser Val Asp Val Ala
                485                 490                 495

Ala His Glu Gln Pro Glu Met Phe Asp Leu Ala Arg Pro Ala Ile Asp
            500                 505                 510

Phe Val Ala Leu Ser Arg Ser Leu Gly Val Pro Ala Val Arg Val Glu
        515                 520                 525

Lys Pro Asp Gln Ala Lys Ala Ala Val Glu Gln Ala Leu Gly Thr Pro
    530                 535                 540

Gly Pro Phe Leu Ile Asp Leu Val Thr Gly Arg Gly Arg Glu Asp
545                 550                 555

<210> SEQ ID NO 9
<211> LENGTH: 536
<212> TYPE: PRT
<213> ORGANISM: Amycolatopsis alba

<400> SEQUENCE: 9

Met Asn Val Ala Glu Leu Val Gly Arg Thr Leu Ala Glu Leu Gly Val
1               5                   10                  15

Gly Ala Ala Phe Gly Val Val Gly Ser Gly Asn Phe Val Thr Asn
            20                  25                  30

Gly Leu Arg Ala Gly Gly Val Arg Phe Val Ala Ala Arg His Glu Gly
        35                  40                  45

Gly Ala Ala Ser Met Ala Asp Ala Tyr Ala Arg Met Ser Gly Arg Val
    50                  55                  60

Ser Val Leu Ser Leu His Gln Gly Cys Gly Leu Thr Asn Ala Leu Thr
65                  70                  75                  80

Gly Ile Thr Glu Ala Ala Lys Ser Arg Thr Pro Met Ile Val Leu Thr
                85                  90                  95

Gly Asp Thr Ala Ala Ser Ala Val Leu Ser Asn Phe Arg Ile Gly Gln
            100                 105                 110

Asp Ala Leu Ala Thr Ala Val Gly Ala Val Pro Glu Arg Val His Ser
        115                 120                 125

Ala Pro Thr Ala Val Ala Asp Thr Val Arg Ala Tyr Arg Thr Ala Val
    130                 135                 140

Gln Gln Arg Arg Thr Val Leu Leu Asn Leu Pro Leu Asp Val Gln Ala
145                 150                 155                 160

Gln Glu Ala Pro Glu Ala Val Glu Ile Pro Lys Val Arg Gly Pro Ala
                165                 170                 175

Pro Ile Arg Pro Asp Ala Gly Met Val Ala Lys Leu Ala Asp Leu Leu
            180                 185                 190

Ala Glu Ala Arg Arg Pro Val Phe Ile Ala Gly Arg Gly Ala Arg Ala
        195                 200                 205

Ser Ala Val Pro Leu Arg Glu Leu Ala Glu Ile Ser Gly Ala Leu Leu
    210                 215                 220
```

```
Ala Thr Ser Ala Val Ala His Gly Leu Phe His Asp Asp Pro Phe Ser
225                 230                 235                 240

Leu Gly Ile Ser Gly Gly Phe Ser Ser Pro Arg Thr Ala Asp Leu Ile
            245                 250                 255

Val Asp Ala Asp Leu Val Ile Gly Trp Gly Cys Ala Leu Asn Met Trp
        260                 265                 270

Thr Thr Arg His Gly Thr Leu Leu Gly Pro Ala Ala Arg Leu Val Gln
            275                 280                 285

Val Asp Val Glu Gln Ala Ala Leu Gly Ala His Arg Pro Ile Asp Leu
    290                 295                 300

Gly Val Val Gly Asp Val Ala Gly Thr Ala Val Asp Val His Ala Glu
305                 310                 315                 320

Leu Asp Lys Arg Gly His Gln Arg Ser Arg Glu Ala Pro Thr Gly Thr
                325                 330                 335

Arg Trp Asn Asp Val Pro Tyr Asn Asp Leu Ser Gly Asp Gly Arg Ile
            340                 345                 350

Asp Pro Arg Thr Leu Ser Arg Arg Leu Asp Glu Ile Leu Pro Ala Glu
        355                 360                 365

Arg Met Val Ser Ile Asp Ser Gly Asn Phe Met Gly Tyr Pro Ser Ala
370                 375                 380

Tyr Leu Ser Val Pro Asp Glu Asn Gly Phe Cys Phe Thr Gln Ala Phe
385                 390                 395                 400

Gln Ser Ile Gly Leu Gly Leu Gly Thr Ala Ile Gly Ala Ala Leu Ala
                405                 410                 415

Arg Pro Asp Arg Leu Pro Val Leu Gly Val Gly Asp Gly Gly Phe His
            420                 425                 430

Met Ala Val Ser Glu Leu Glu Thr Ala Val Arg Leu Arg Ile Pro Leu
        435                 440                 445

Val Ile Val Val Tyr Asn Asp Ala Ala Tyr Gly Ala Glu Ile His His
    450                 455                 460

Phe Gly Asp Ala Asp Met Thr Thr Val Arg Phe Pro Asp Thr Asp Ile
465                 470                 475                 480

Ala Ala Ile Gly Arg Gly Phe Gly Cys Asp Gly Val Thr Val Arg Ser
                485                 490                 495

Val Gly Asp Leu Ala Ala Val Lys Glu Trp Leu Gly Gly Pro Arg Asp
            500                 505                 510

Ala Pro Leu Val Ile Asp Ala Lys Ile Ala Asp Asp Gly Gly Ser Trp
        515                 520                 525

Trp Leu Ala Glu Ala Phe Arg His
            530                 535

<210> SEQ ID NO 10
<211> LENGTH: 584
<212> TYPE: PRT
<213> ORGANISM: Actinoplanes missouriensis

<400> SEQUENCE: 10

Met Ile Asp Leu Asp Gly Thr Val Thr Val Ala Glu Tyr Leu Gly Leu
1               5                   10                  15

Arg Leu Arg His Ala Gly Val Glu His Leu Phe Gly Val Pro Gly Asp
                20                  25                  30

Phe Asn Leu Asn Leu Leu Asp Gly Leu Ala Phe Val Glu Gly Leu Arg
            35                  40                  45

Trp Val Gly Ser Pro Asn Glu Leu Gly Ala Gly Tyr Ala Ala Asp Ala
```

-continued

```
                50                  55                  60
Tyr Ala Arg Arg Gly Leu Ser Ala Leu Phe Thr Thr Tyr Gly Val
 65                  70                  75                  80

Gly Glu Leu Ser Ala Ile Asn Ala Val Ala Gly Ser Ala Ala Glu Asp
                 85                  90                  95

Ser Pro Val Val His Val Val Gly Ser Pro Arg Thr Thr Val Ala
                100                 105                 110

Gly Gly Ala Leu Val His His Thr Ile Ala Asp Gly Asp Phe Arg His
                115                 120                 125

Phe Ala Arg Ala Tyr Ala Glu Val Thr Val Ala Gln Ala Met Val Thr
            130                 135                 140

Ala Thr Asp Ala Gly Ala Gln Ile Asp Arg Val Leu Leu Ala Ala Leu
145                 150                 155                 160

Thr His Arg Lys Pro Val Tyr Leu Ser Ile Pro Gln Asp Leu Ala Leu
                165                 170                 175

His Arg Ile Pro Ala Ala Pro Leu Arg Glu Pro Leu Thr Pro Ala Ser
                180                 185                 190

Asp Pro Ala Ala Val Glu Arg Phe Arg Thr Ala Val Arg Asp Leu Leu
            195                 200                 205

Thr Pro Ala Val Arg Pro Ile Met Leu Val Gly Gln Leu Val Ser Arg
210                 215                 220

Tyr Gly Leu Ser Thr Leu Val Thr Asp Met Thr Thr Arg Ser Gly Ile
225                 230                 235                 240

Pro Val Ala Ala Gln Leu Ser Ala Lys Gly Val Ile Asp Glu Ser Val
                245                 250                 255

Glu Gly Asn Leu Gly Leu Tyr Ala Gly Ser Met Leu Asp Gly Pro Ala
                260                 265                 270

Ala Ser Leu Ile Asp Ser Ala Asp Val Val Leu His Leu Gly Thr Ala
            275                 280                 285

Leu Thr Ala Glu Leu Thr Gly Phe Phe Thr His Arg Arg Pro Asp Ala
            290                 295                 300

Arg Thr Val Gln Leu Leu Ser Thr Ala Ala Leu Val Gly Thr Thr Arg
305                 310                 315                 320

Phe Asp Asn Val Leu Phe Pro Asp Ala Met Thr Thr Leu Ala Glu Val
                325                 330                 335

Leu Thr Thr Phe Pro Ala Pro Ala Arg Leu Ala Ala Pro Thr Thr Arg
                340                 345                 350

Ala Glu Pro Thr Gly Leu Ala Ala Ser Ile Thr Pro Pro Ala Pro Ser
            355                 360                 365

Ala Val Asp Leu Thr Ala Ser Thr Ala Thr Asp Leu Thr Ala Pro Thr
370                 375                 380

Ala Gly Asp Ile Ser Glu Met Ser Arg Val Leu Thr Gln Asp Ala Phe
385                 390                 395                 400

Trp Ala Gly Met Gln Ala Trp Leu Pro Ala Gly His Ala Leu Val Ala
                405                 410                 415

Asp Thr Gly Thr Ser Tyr Trp Gly Ala Leu Ala Leu Arg Leu Pro Gly
                420                 425                 430

Asp Thr Val Phe Leu Gly Gln Pro Ile Trp Asn Ser Ile Gly Trp Ala
            435                 440                 445

Leu Pro Ala Val Leu Gly Gln Gly Leu Ala Asp Pro Asp Arg Arg Pro
450                 455                 460

Val Leu Val Ile Gly Asp Gly Ala Ala Gln Met Thr Ile Gln Glu Leu
465                 470                 475                 480
```

```
Ser Thr Ile Val Ala Ala Gly Leu Arg Pro Ile Ile Leu Leu Leu Asn
            485                 490                 495

Asn Arg Gly Tyr Thr Ile Glu Arg Ala Leu Gln Ser Pro Asn Ala Gly
        500                 505                 510

Tyr Asn Asp Val Ala Asp Trp Asn Trp Arg Ala Val Val Ala Ala Phe
            515                 520                 525

Ala Gly Pro Asp Thr Asp Tyr His His Ala Ala Thr Gly Thr Glu Leu
        530                 535                 540

Ala Lys Ala Leu Thr Ala Ala Ser Glu Ser Asn Arg Pro Val Phe Ile
545                 550                 555                 560

Glu Val Glu Leu Asp Ala Phe Asp Thr Pro Pro Leu Leu Arg Arg Leu
            565                 570                 575

Ala Glu Arg Ala Thr Ala Pro Ser
            580
```

<210> SEQ ID NO 11
<211> LENGTH: 546
<212> TYPE: PRT
<213> ORGANISM: Staphylococcus aureus

<400> SEQUENCE: 11

```
Met Lys Gln Arg Ile Gly Ala Tyr Leu Ile Asp Ala Ile His Arg Ala
1               5                   10                  15

Gly Val Asp Lys Ile Phe Gly Val Pro Gly Asp Phe Asn Leu Ala Phe
            20                  25                  30

Leu Asp Asp Ile Ile Ser Asn Pro Asn Val Asp Trp Val Gly Asn Thr
        35                  40                  45

Asn Glu Leu Asn Ala Ser Tyr Ala Ala Asp Gly Tyr Ala Arg Leu Asn
    50                  55                  60

Gly Leu Ala Ala Leu Val Thr Thr Phe Gly Val Gly Glu Leu Ser Ala
65                  70                  75                  80

Val Asn Gly Ile Ala Gly Ser Tyr Ala Glu Arg Ile Pro Val Ile Ala
                85                  90                  95

Ile Thr Gly Ala Pro Thr Arg Ala Val Glu His Ala Gly Lys Tyr Val
            100                 105                 110

His His Ser Leu Gly Glu Gly Thr Phe Asp Asp Tyr Arg Lys Met Phe
        115                 120                 125

Ala His Ile Thr Val Ala Gln Gly Tyr Ile Thr Pro Glu Asn Ala Thr
    130                 135                 140

Thr Glu Ile Pro Arg Leu Ile Asn Thr Ala Ile Ala Glu Arg Arg Pro
145                 150                 155                 160

Val His Leu His Leu Pro Ile Asp Val Ala Ile Ser Glu Ile Glu Ile
                165                 170                 175

Pro Thr Pro Phe Glu Val Thr Ala Ala Lys Asp Thr Asp Ala Ser Thr
            180                 185                 190

Tyr Ile Glu Leu Leu Thr Ser Lys Leu His Gln Ser Lys Gln Pro Ile
        195                 200                 205

Ile Ile Thr Gly His Glu Ile Asn Ser Phe His Leu His Gln Glu Leu
    210                 215                 220

Glu Asp Phe Val Asn Gln Thr Gln Ile Pro Val Ala Gln Leu Ser Leu
225                 230                 235                 240

Gly Lys Gly Ala Phe Asn Glu Glu Asn Pro Tyr Tyr Met Gly Ile Tyr
                245                 250                 255

Asp Gly Lys Ile Ala Glu Asp Lys Ile Arg Asp Tyr Val Asp Asn Ser
```

-continued

```
            260                 265                 270
Asp Leu Ile Leu Asn Ile Gly Ala Lys Leu Thr Asp Ser Ala Thr Ala
            275                 280                 285

Gly Phe Ser Tyr Gln Phe Asn Ile Asp Asp Val Val Met Leu Asn His
        290                 295                 300

His Asn Ile Lys Ile Asp Asp Val Thr Asn Asp Glu Ile Ser Leu Pro
305                 310                 315                 320

Ser Leu Leu Lys Gln Leu Ser Asn Ile Ser His Thr Asn Asn Ala Thr
                325                 330                 335

Phe Pro Ala Tyr His Arg Pro Thr Ser Pro Asp Tyr Thr Val Gly Thr
            340                 345                 350

Glu Pro Leu Thr Gln Gln Thr Tyr Phe Lys Met Met Gln Asn Phe Leu
        355                 360                 365

Lys Pro Asn Asp Val Ile Ile Ala Asp Gln Gly Thr Ser Phe Phe Gly
    370                 375                 380

Ala Tyr Asp Leu Ala Leu Tyr Lys Asn Asn Thr Phe Ile Gly Gln Pro
385                 390                 395                 400

Leu Trp Gly Ser Ile Gly Tyr Thr Leu Pro Ala Thr Leu Gly Ser Gln
                405                 410                 415

Leu Ala Asp Lys Asp Arg Arg Asn Leu Leu Ile Gly Asp Gly Ser
            420                 425                 430

Leu Gln Leu Thr Val Gln Ala Ile Ser Thr Met Ile Arg Gln His Ile
        435                 440                 445

Lys Pro Val Leu Phe Val Ile Asn Asn Asp Gly Tyr Thr Val Glu Arg
    450                 455                 460

Leu Ile His Gly Met Tyr Glu Pro Tyr Asn Glu Ile His Met Trp Asp
465                 470                 475                 480

Tyr Lys Ala Leu Pro Ala Val Phe Gly Gly Lys Asn Val Glu Ile His
                485                 490                 495

Asp Val Glu Ser Ser Lys Asp Leu Gln Asp Thr Phe Asn Ala Ile Asn
            500                 505                 510

Gly His Pro Asp Val Met His Phe Val Glu Val Lys Met Ser Val Glu
        515                 520                 525

Asp Ala Pro Lys Lys Leu Ile Asp Ile Ala Lys Ala Phe Ser Gln Gln
    530                 535                 540

Asn Lys
545

<210> SEQ ID NO 12
<211> LENGTH: 528
<212> TYPE: PRT
<213> ORGANISM: Pseudomonas aeruginosa

<400> SEQUENCE: 12

Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
        35                  40                  45

Ala Val Val Gly Met Ala Asp Gly Phe Ala Leu Ala Ser Gly Arg Pro
    50                  55                  60

Ala Phe Val Asn Leu His Ala Ala Gly Thr Gly Asn Gly Met Gly
65                  70                  75                  80
```

```
Ala Leu Thr Asn Ala Trp Tyr Ser His Ser Pro Leu Val Ile Thr Ala
                85                  90                  95
Gly Gln Gln Val Arg Ser Met Ile Gly Val Glu Ala Met Leu Ala Asn
            100                 105                 110
Val Asp Ala Gly Gln Leu Pro Lys Pro Leu Val Lys Trp Ser His Glu
        115                 120                 125
Pro Ala Cys Ala Gln Asp Val Pro Arg Ala Leu Ser Gln Ala Ile Gln
    130                 135                 140
Thr Ala Ser Leu Pro Pro Arg Ala Pro Val Tyr Leu Ser Ile Pro Tyr
145                 150                 155                 160
Asp Asp Trp Ala Gln Pro Ala Pro Ala Gly Val Glu His Leu Ala Ala
                165                 170                 175
Arg Gln Val Ser Gly Ala Ala Leu Pro Ala Pro Ala Leu Leu Ala Glu
            180                 185                 190
Leu Gly Glu Arg Leu Ser Arg Ser Arg Asn Pro Val Leu Val Leu Gly
        195                 200                 205
Pro Asp Val Asp Gly Ala Asn Ala Asn Gly Leu Ala Val Glu Leu Ala
    210                 215                 220
Glu Lys Leu Arg Met Pro Ala Trp Gly Ala Pro Ser Ala Ser Arg Cys
225                 230                 235                 240
Pro Phe Pro Thr Arg His Ala Cys Phe Arg Gly Val Leu Pro Ala Ala
                245                 250                 255
Ile Ala Gly Ile Ser Arg Leu Leu Asp Gly His Asp Leu Ile Leu Val
            260                 265                 270
Val Gly Ala Pro Val Phe Arg Tyr His Gln Phe Ala Pro Gly Asp Tyr
        275                 280                 285
Leu Pro Ala Gly Ala Glu Leu Val Gln Val Thr Cys Asp Pro Gly Glu
    290                 295                 300
Ala Ala Arg Ala Pro Met Gly Asp Ala Leu Val Gly Asp Ile Ala Leu
305                 310                 315                 320
Thr Leu Glu Ala Leu Leu Glu Gln Val Arg Pro Ser Ala Arg Pro Leu
                325                 330                 335
Pro Glu Ala Leu Pro Arg Pro Pro Ala Leu Ala Glu Glu Gly Gly Pro
            340                 345                 350
Leu Arg Pro Glu Thr Val Phe Asp Val Ile Asp Ala Leu Ala Pro Arg
        355                 360                 365
Asp Ala Ile Phe Val Lys Glu Ser Thr Ser Thr Val Thr Ala Phe Trp
    370                 375                 380
Gln Arg Val Glu Met Arg Glu Pro Gly Ser Tyr Phe Phe Pro Ala Ala
385                 390                 395                 400
Gly Gly Leu Gly Phe Gly Leu Pro Ala Ala Val Gly Ala Gln Leu Ala
                405                 410                 415
Gln Pro Arg Arg Gln Val Ile Gly Ile Ile Gly Asp Gly Ser Ala Asn
            420                 425                 430
Tyr Gly Ile Thr Ala Leu Trp Ser Ala Ala Gln Tyr Arg Val Pro Ala
        435                 440                 445
Val Phe Ile Ile Leu Lys Asn Gly Thr Tyr Gly Ala Leu Arg Trp Phe
    450                 455                 460
Ala Gly Val Leu Glu Val Pro Asp Ala Pro Gly Leu Asp Val Pro Gly
465                 470                 475                 480
Leu Asp Phe Cys Ala Ile Ala Arg Gly Tyr Gly Val Glu Ala Leu His
                485                 490                 495
Ala Ala Thr Arg Glu Glu Leu Glu Gly Ala Leu Lys His Ala Leu Ala
```

Ala Asp Arg Pro Val Leu Ile Glu Val Pro Thr Gln Thr Ile Glu Pro
500                 505                 510
            515                 520                 525

<210> SEQ ID NO 13
<211> LENGTH: 548
<212> TYPE: PRT
<213> ORGANISM: Carnobacterium maltaromaticum

<400> SEQUENCE: 13

Met Tyr Thr Val Gly Asn Tyr Leu Leu Asp Arg Leu Thr Glu Leu Gly
1               5                   10                  15

Ile Arg Asp Ile Phe Gly Val Pro Gly Asp Tyr Asn Leu Lys Phe Leu
            20                  25                  30

Asp His Val Met Thr His Lys Glu Leu Asn Trp Ile Gly Asn Ala Asn
        35                  40                  45

Glu Leu Asn Ala Ala Tyr Ala Ala Asp Gly Tyr Ala Arg Thr Lys Gly
    50                  55                  60

Ile Ala Ala Leu Val Thr Thr Phe Gly Val Gly Glu Leu Ser Ala Ala
65                  70                  75                  80

Asn Gly Thr Ala Gly Ser Tyr Ala Glu Lys Val Pro Val Val Gln Ile
                85                  90                  95

Val Gly Thr Pro Thr Thr Ala Val Gln Asn Ser His Lys Leu Val His
            100                 105                 110

His Thr Leu Gly Asp Gly Arg Phe Asp His Phe Glu Lys Met Gln Thr
        115                 120                 125

Glu Ile Asn Gly Ala Ile Ala His Leu Thr Ala Asp Asn Ala Leu Ala
    130                 135                 140

Glu Ile Asp Arg Val Leu Arg Ile Ala Val Thr Glu Arg Cys Pro Val
145                 150                 155                 160

Tyr Ile Asn Leu Ala Ile Asp Val Ala Glu Val Val Ala Glu Lys Pro
                165                 170                 175

Leu Lys Pro Leu Met Glu Glu Ser Lys Lys Val Glu Glu Glu Thr Thr
            180                 185                 190

Leu Val Leu Asn Lys Ile Glu Lys Ala Leu Gln Asp Ser Lys Asn Pro
        195                 200                 205

Val Val Leu Ile Gly Asn Glu Ile Ala Ser Phe His Leu Glu Ser Ala
    210                 215                 220

Leu Ala Asp Phe Val Lys Lys Phe Asn Leu Pro Val Thr Val Leu Pro
225                 230                 235                 240

Phe Gly Lys Gly Gly Phe Asp Glu Glu Asp Ala His Phe Ile Gly Val
                245                 250                 255

Tyr Thr Gly Ala Pro Thr Ala Glu Ser Ile Lys Glu Arg Val Glu Lys
            260                 265                 270

Ala Asp Leu Ile Leu Ile Ile Gly Ala Lys Leu Thr Asp Ser Ala Thr
        275                 280                 285

Ala Gly Phe Ser Tyr Asp Phe Glu Asp Arg Gln Val Ile Ser Val Gly
    290                 295                 300

Ser Asp Glu Val Ser Phe Tyr Gly Glu Ile Met Lys Pro Val Ala Phe
305                 310                 315                 320

Ala Gln Phe Val Asn Gly Leu Asn Ser Leu Asn Tyr Leu Gly Tyr Thr
                325                 330                 335

Gly Glu Ile Lys Gln Val Glu Arg Val Ala Asp Ile Glu Ala Lys Ala
            340                 345                 350

-continued

```
Ser Asn Leu Thr Gln Asn Asn Phe Trp Lys Phe Val Glu Lys Tyr Leu
            355                 360                 365

Ser Asn Gly Asp Thr Leu Val Ala Glu Gln Gly Thr Ser Phe Phe Gly
        370                 375                 380

Ala Ser Leu Val Pro Leu Lys Ser Lys Met Lys Phe Ile Gly Gln Pro
385                 390                 395                 400

Leu Trp Gly Ser Ile Gly Tyr Thr Phe Pro Ala Met Leu Gly Ser Gln
                405                 410                 415

Ile Ala Asn Pro Ala Ser Arg His Leu Leu Phe Ile Gly Asp Gly Ser
            420                 425                 430

Leu Gln Leu Thr Ile Gln Glu Leu Gly Met Thr Phe Arg Glu Lys Leu
        435                 440                 445

Thr Pro Ile Val Phe Val Ile Asn Asn Asp Gly Tyr Thr Val Glu Arg
450                 455                 460

Glu Ile His Gly Pro Asn Glu Leu Tyr Asn Asp Ile Pro Met Trp Asp
465                 470                 475                 480

Tyr Gln Asn Leu Pro Tyr Val Phe Gly Gly Asn Lys Gly Asn Val Ala
                485                 490                 495

Thr Tyr Lys Val Thr Thr Glu Glu Leu Val Ala Ala Met Ser Gln
            500                 505                 510

Ala Arg Gln Asp Thr Thr Arg Leu Gln Trp Ile Glu Val Val Met Gly
        515                 520                 525

Lys Gln Asp Ser Pro Asp Leu Leu Val Gln Leu Gly Lys Val Phe Ala
530                 535                 540

Lys Gln Asn Ser
545

<210> SEQ ID NO 14
<211> LENGTH: 529
<212> TYPE: PRT
<213> ORGANISM: Klebsiella sp. 1_1_55

<400> SEQUENCE: 14

Met Lys Thr Ile His Ser Ala Ala Tyr Ala Leu Leu Arg Arg His Gly
1               5                   10                  15

Met Thr Thr Ile Phe Gly Asn Pro Gly Ser Asn Glu Leu Pro Phe Leu
            20                  25                  30

Lys Ser Phe Pro Glu Asp Phe Gln Tyr Val Leu Gly Leu His Glu Gly
        35                  40                  45

Ala Val Val Gly Met Ala Asp Gly Tyr Ala Leu Ala Ser Gly Lys Pro
    50                  55                  60

Ala Phe Val Asn Leu His Ala Ala Gly Thr Gly Asn Gly Met Gly
65                  70                  75                  80

Ala Leu Thr Asn Ser Trp Tyr Ser His Ser Pro Leu Val Ile Thr Ala
                85                  90                  95

Gly Gln Gln Val Arg Pro Met Ile Gly Val Glu Ala Met Leu Ala Asn
            100                 105                 110

Val Asp Ala Thr Gln Leu Pro Lys Pro Leu Val Lys Trp Ser Tyr Glu
        115                 120                 125

Pro Ala Asn Ala Gln Asp Val Pro Arg Ala Leu Ser Gln Ala Ile His
    130                 135                 140

Tyr Ala Asn Thr Thr Pro Lys Ala Pro Val Tyr Leu Ser Ile Pro Tyr
145                 150                 155                 160

Asp Asp Trp Asp Gln Pro Ser Gly Pro Gly Val Glu His Leu Ile Glu
                165                 170                 175
```

```
Arg Asp Val Gln Thr Ala Gly Thr Pro Asp Ala Arg Gln Leu Gln Val
            180                 185                 190

Leu Val Gln Gln Val Gln Asp Ala Arg Asn Pro Val Leu Val Leu Gly
        195                 200                 205

Pro Asp Val Asp Ala Thr Leu Ser Asn Asp His Ala Val Ala Leu Ala
210                 215                 220

Asp Lys Leu Arg Met Pro Val Trp Ile Ala Pro Ser Ala Ser Arg Cys
225                 230                 235                 240

Pro Phe Pro Thr Arg His Pro Ser Phe Arg Gly Val Leu Pro Ala Ala
                245                 250                 255

Ile Ala Gly Ile Ser Lys Thr Leu Gln Gly His Asp Leu Ile Ile Val
            260                 265                 270

Val Gly Ala Pro Val Phe Arg Tyr His Gln Phe Ala Pro Gly Asp Tyr
        275                 280                 285

Leu Pro Val Gly Ala Gln Leu Leu His Ile Thr Ser Asp Pro Leu Glu
    290                 295                 300

Ala Thr Arg Ala Pro Met Gly His Ala Leu Val Gly Asp Ile Arg Glu
305                 310                 315                 320

Thr Leu Arg Val Leu Ala Glu Glu Val Val Gln Gln Ser Arg Pro Tyr
                325                 330                 335

Pro Glu Ala Leu Ala Ala Pro Glu Cys Val Thr Asp Glu Pro His His
            340                 345                 350

Leu His Pro Glu Thr Leu Phe Asp Val Leu Asp Ala Val Ala Pro His
        355                 360                 365

Asp Ala Ile Tyr Val Lys Glu Ser Thr Ser Thr Thr Thr Ala Phe Trp
370                 375                 380

Gln Arg Met Asn Leu Arg His Pro Gly Ser Tyr Tyr Phe Pro Ala Ala
385                 390                 395                 400

Gly Gly Leu Gly Phe Gly Leu Pro Ala Ala Val Gly Val Gln Leu Ala
                405                 410                 415

Gln Pro Gln Arg Arg Val Val Ala Leu Ile Gly Asp Gly Ser Ala Asn
            420                 425                 430

Tyr Gly Ile Thr Ala Leu Trp Thr Ala Ala Gln Tyr Arg Ile Pro Val
        435                 440                 445

Val Phe Ile Ile Leu Lys Asn Gly Thr Tyr Gly Ala Leu Arg Trp Phe
450                 455                 460

Ala Gly Val Leu Lys Ala Glu Asp Ser Pro Gly Leu Asp Val Pro Gly
465                 470                 475                 480

Leu Asp Phe Cys Ala Ile Ala Lys Gly Tyr Gly Val Lys Ala Val His
                485                 490                 495

Thr Asp Thr Arg Asp Ser Phe Glu Ala Ala Leu Arg Thr Ala Leu Asp
            500                 505                 510

Ala Asn Glu Pro Thr Val Ile Glu Val Pro Thr Leu Thr Ile Gln Pro
        515                 520                 525

His

<210> SEQ ID NO 15
<211> LENGTH: 564
<212> TYPE: PRT
<213> ORGANISM: Klebsiella sp. 1_1_55

<400> SEQUENCE: 15

Met Ser Asn Ala Ile Thr Lys Val Gln Asn Ala Asn Ala Arg Arg Gly
1               5                   10                  15
```

```
Gly Asp Val Leu Leu Glu Val Leu Glu Ser Glu Gly Val Glu Tyr Val
             20                  25                  30

Phe Gly Asn Pro Gly Thr Thr Glu Leu Pro Phe Met Asp Ala Leu Leu
         35                  40                  45

Arg Lys Pro Ser Ile Gln Tyr Val Leu Ala Leu Gln Glu Ala Ser Ala
     50                  55                  60

Val Ala Met Ala Asp Gly Tyr Ala Gln Ala Lys Lys Pro Gly Phe
 65                  70                  75                  80

Leu Asn Leu His Thr Ala Gly Leu Gly His Gly Met Gly Asn Leu
                 85                  90                  95

Leu Asn Ala Lys Cys Ser Gln Thr Pro Leu Val Val Thr Ala Gly Gln
             100                 105                 110

Gln Asp Ser Arg His Thr Thr Thr Asp Pro Leu Leu Leu Gly Asp Leu
         115                 120                 125

Val Gly Met Gly Lys Thr Phe Ala Lys Trp Ser Gln Glu Val Thr His
 130                 135                 140

Val Asp Gln Leu Pro Val Leu Val Arg Arg Ala Phe His Asp Ser Asp
145                 150                 155                 160

Ala Ala Pro Lys Gly Ser Val Phe Leu Ser Leu Pro Met Asp Val Met
                 165                 170                 175

Glu Ala Met Ser Ala Ile Gly Ile Gly Ala Pro Ser Thr Ile Asp Arg
             180                 185                 190

Asn Ala Val Ala Gly Ser Leu Pro Leu Leu Ala Ser Lys Leu Ala Ala
             195                 200                 205

Phe Thr Pro Gly Asn Val Ala Leu Ile Ala Gly Asp Glu Ile Tyr Gln
     210                 215                 220

Ser Glu Ala Ala Asn Glu Val Val Ala Leu Ala Glu Met Leu Ala Ala
225                 230                 235                 240

Asp Val Tyr Gly Ser Thr Trp Pro Asn Arg Ile Pro Tyr Pro Thr Ala
                 245                 250                 255

His Pro Leu Trp Arg Gly Asn Leu Ser Thr Lys Ala Thr Glu Ile Asn
             260                 265                 270

Arg Ala Leu Ser Gln Tyr Asp Ala Ile Phe Ala Leu Gly Gly Lys Ser
     275                 280                 285

Leu Ile Thr Ile Leu Tyr Thr Glu Gly Gln Ala Val Pro Glu Gln Cys
 290                 295                 300

Lys Val Phe Gln Leu Ser Ala Asp Ala Gly Asp Leu Gly Arg Thr Tyr
305                 310                 315                 320

Ser Ser Glu Leu Ser Val Val Gly Asp Ile Lys Ser Ser Leu Lys Val
                 325                 330                 335

Leu Leu Pro Glu Leu Glu Lys Ala Thr Ala Asn His Arg Arg Asp Tyr
             340                 345                 350

Gln Arg Arg Phe Glu Lys Ala Ile Asn Glu Phe Lys Leu Ser Lys Glu
     355                 360                 365

Ser Leu Leu Gly Gln Val Gln Glu Gln Ser Ala Thr Val Ile Thr
 370                 375                 380

Pro Leu Val Ala Ala Phe Glu Ala Ala Arg Ala Ile Gly Pro Asp Val
385                 390                 395                 400

Ala Ile Val Asp Glu Ala Ile Ala Thr Ser Gly Ser Leu Arg Lys Ser
                 405                 410                 415

Leu Asn Ser His Arg Ala Asp Gln Tyr Ala Phe Leu Arg Gly Gly Gly
             420                 425                 430
```

```
Leu Gly Trp Gly Met Pro Ala Val Gly Tyr Ser Leu Gly Leu Gly
            435                 440                 445

Lys Ala Pro Val Val Cys Phe Val Gly Asp Gly Ala Ala Met Tyr Ser
450                 455                 460

Pro Gln Ala Leu Trp Thr Ala Ala His Glu Lys Leu Pro Val Thr Phe
465                 470                 475                 480

Ile Val Met Asn Asn Thr Glu Tyr Asn Val Leu Lys Asn Phe Met Arg
                485                 490                 495

Ser Gln Ala Asp Tyr Thr Ser Ala Gln Thr Asp Arg Phe Ile Ala Met
            500                 505                 510

Asp Leu Val Asn Pro Ser Val Asp Tyr Gln Ala Leu Gly Ala Ser Met
            515                 520                 525

Gly Leu Glu Thr Arg Lys Val Ile Arg Ala Gly Asp Ile Ala Pro Ala
530                 535                 540

Val Glu Ala Ala Leu Ala Ser Gly Lys Pro Asn Val Ile Glu Ile Ile
545                 550                 555                 560

Ile Ser Lys Ser

<210> SEQ ID NO 16
<211> LENGTH: 566
<212> TYPE: PRT
<213> ORGANISM: Burkholderia sp. Ch1-1

<400> SEQUENCE: 16

Met Thr Ser Arg Ser Ser Phe Ser Pro Pro Ser Ala Ser Glu Gln Arg
1               5                   10                  15

Gly Ala Asp Ile Phe Ala Glu Val Leu Gln Cys Glu Gly Val Arg Tyr
            20                  25                  30

Ile Phe Gly Asn Pro Gly Thr Thr Glu Leu Pro Leu Leu Asp Ala Leu
        35                  40                  45

Thr Asp Ile Thr Gly Ile His Tyr Val Leu Gly Leu His Glu Ala Ser
    50                  55                  60

Val Val Ala Met Ala Asp Gly Tyr Ala Gln Ala Ser Gly Lys Pro Gly
65                  70                  75                  80

Phe Val Asn Leu His Thr Ala Gly Gly Leu Gly Asn Ala Met Gly Ala
                85                  90                  95

Ile Leu Asn Ala Lys Met Ala Asn Thr Pro Leu Val Val Thr Ala Gly
            100                 105                 110

Gln Gln Asp Thr Arg His Gly Val Thr Asp Pro Leu Leu His Gly Asp
        115                 120                 125

Leu Thr Gly Ile Ala Arg Pro Asn Val Lys Trp Ala Glu Glu Ile His
    130                 135                 140

His Pro Glu His Ile Pro Met Leu Leu Arg Arg Ala Leu Gln Asp Cys
145                 150                 155                 160

Arg Thr Gly Pro Ala Gly Pro Val Phe Leu Ser Leu Pro Ile Asp Thr
                165                 170                 175

Met Glu Arg Cys Thr Ser Val Gly Ala Gly Glu Ala Ser Arg Ile Glu
            180                 185                 190

Arg Ala Ser Val Ala Asn Met Leu His Ala Leu Ala Thr Ala Leu Ala
        195                 200                 205

Glu Val Thr Ala Gly His Ile Ala Leu Val Ala Gly Glu Glu Val Phe
    210                 215                 220

Thr Ala Asn Ala Ser Val Glu Val Ala Leu Ala Glu Ala Leu Gly
225                 230                 235                 240
```

Ala Pro Val Phe Gly Ala Ser Trp Pro Gly His Ile Pro Phe Pro Thr
                245                 250                 255

Ala His Pro Gln Trp Gln Gly Thr Leu Pro Pro Lys Ala Ser Asp Ile
            260                 265                 270

Arg Glu Thr Leu Gly Pro Phe Asp Ala Val Leu Ile Leu Gly Gly His
        275                 280                 285

Ser Leu Ile Ser Tyr Pro Tyr Ser Glu Gly Pro Ala Ile Pro Pro His
    290                 295                 300

Cys Arg Leu Phe Gln Leu Thr Gly Asp Gly His Gln Ile Gly Arg Val
305                 310                 315                 320

His Glu Thr Thr Leu Gly Leu Val Gly Asp Leu Gln Leu Ser Leu Arg
                325                 330                 335

Ala Leu Leu Pro Leu Leu Ala Arg Lys Leu Gln Pro Gln Asn Gly Ala
            340                 345                 350

Val Ala Arg Leu Arg Gln Val Ala Thr Leu Lys Arg Asp Ala Arg Arg
        355                 360                 365

Thr Glu Ala Ala Glu Arg Ser Ala Arg Glu Phe Asp Ala Ser Ala Thr
    370                 375                 380

Thr Pro Phe Val Ala Ala Phe Glu Thr Ile Arg Ala Ile Gly Pro Asp
385                 390                 395                 400

Val Pro Ile Val Asp Glu Ala Pro Val Thr Ile Pro His Val Arg Ala
                405                 410                 415

Cys Leu Asp Ser Ala Ser Ala Arg Gln Tyr Leu Phe Thr Arg Ser Ala
            420                 425                 430

Ile Leu Gly Trp Gly Met Pro Ala Ala Val Gly Val Ser Leu Gly Leu
        435                 440                 445

Asp Arg Ser Pro Val Val Cys Leu Val Gly Asp Gly Ser Ala Met Tyr
    450                 455                 460

Ser Pro Gln Ala Leu Trp Thr Ala Ala His Glu Arg Leu Pro Val Thr
465                 470                 475                 480

Phe Val Val Phe Asn Asn Gly Glu Tyr Asn Ile Leu Lys Asn Tyr Ala
                485                 490                 495

Arg Ala Gln Thr Asn Tyr Arg Ser Ala Arg Ala Asn Arg Phe Ile Gly
            500                 505                 510

Leu Asp Ile Ser Asp Pro Ala Ile Asp Phe Pro Ala Leu Ala Ser Ser
        515                 520                 525

Leu Gly Val Pro Ala Arg Arg Val Glu Arg Ala Gly Asp Ile Ala Ile
    530                 535                 540

Ala Val Glu Asp Gly Ile Arg Ser Gly Arg Pro Asn Leu Ile Asp Val
545                 550                 555                 560

Leu Ile Ser Ser Ser Ser
                565

<210> SEQ ID NO 17
<211> LENGTH: 562
<212> TYPE: PRT
<213> ORGANISM: Granulicella mallensis

<400> SEQUENCE: 17

Met Asn Ile Ala Tyr Glu Thr Arg Glu Asn Lys Val Ala Ser Gly Arg
1               5                   10                  15

Glu Cys Leu Leu Glu Ile Leu Arg Asp Glu Gly Val Thr His Val Phe
            20                  25                  30

Gly Asn Pro Gly Thr Thr Glu Leu Ala Leu Ile Asp Ala Leu Ala Gly
        35                  40                  45

-continued

```
Asp Asp Asp Phe His Phe Ile Leu Gly Leu Gln Glu Ala Val Val
    50                  55                  60
Gly Met Ala Asp Gly Tyr Ala Gln Ala Thr Gly Arg Pro Ser Phe Val
 65                  70                  75                  80
Asn Leu His Thr Thr Ala Gly Leu Gly Asn Gly Met Gly Asn Leu Thr
                 85                  90                  95
Asn Ala Phe Ala Thr Asn Val Pro Met Val Val Thr Ala Gly Gln Gln
            100                 105                 110
Asp Ile Arg His Leu Ala Tyr Asp Pro Leu Leu Ser Gly Asp Leu Val
            115                 120                 125
Gly Leu Ala Arg Ala Thr Val Lys Trp Ala His Glu Val Arg Ser Leu
130                 135                 140
Gln Glu Leu Pro Ile Ile Leu Arg Arg Ala Phe Arg Asp Ala Asn Thr
145                 150                 155                 160
Glu Pro Arg Gly Pro Val Phe Val Ser Leu Pro Met Asn Ile Ile Asp
                165                 170                 175
Glu Ile Gly Thr Val Ser Ile Pro Pro Arg Ser Thr Ile Val Gln Ala
            180                 185                 190
Glu Ser Gly Asp Ile Ser Gln Leu Val Arg Leu Leu Val Glu Ser Ala
            195                 200                 205
Gly Asn Leu Cys Leu Val Val Gly Asp Glu Val Gly Arg Tyr Gly Ala
    210                 215                 220
Thr Glu Ala Ala Val Arg Val Ala Glu Leu Leu Gly Ala Pro Val Tyr
225                 230                 235                 240
Gly Ser Pro Phe His Ser Asn Val Pro Phe Pro Thr Asp His Pro Leu
                245                 250                 255
Trp Arg Phe Thr Leu Pro Pro Asn Thr Gly Glu Met Arg Lys Val Leu
            260                 265                 270
Gly Gly Tyr Asp Arg Ile Leu Leu Ile Gly Asp Arg Ala Phe Met Ser
    275                 280                 285
Tyr Thr Tyr Ser Asp Glu Leu Pro Leu Ser Pro Lys Thr Gln Leu Leu
290                 295                 300
Gln Ile Ala Val Asp Arg His Ser Leu Gly Arg Cys His Ala Val Glu
305                 310                 315                 320
Leu Gly Leu Tyr Gly Asp Pro Leu Ser Leu Leu Ala Ala Val Gly Asp
                325                 330                 335
Ala Leu Ser Gln Glu Arg Ala Leu Ala Pro Ser Arg Asp Ser Arg Leu
            340                 345                 350
Ala Ile Ala Arg Asp Trp Arg Ala Ser Trp Glu Gln Asp Leu Lys Asp
            355                 360                 365
Glu Cys Glu Arg Leu Ala Pro Ser Arg Pro Leu Tyr Pro Leu Val Ala
    370                 375                 380
Ala Asp Ala Val Leu Arg Gly Val Pro Pro Gly Thr Val Ile Val Asp
385                 390                 395                 400
Glu Cys Leu Ala Thr Asn Lys Tyr Val Arg Gln Leu Tyr Pro Val Arg
                405                 410                 415
Lys Pro Gly Glu Tyr Tyr Tyr Phe Arg Gly Ala Gly Leu Gly Trp Gly
            420                 425                 430
Met Pro Ala Ala Val Gly Val Ser Leu Gly Leu Glu Arg Gln Gln Arg
            435                 440                 445
Val Val Cys Leu Leu Gly Asp Gly Ala Ala Met Tyr Ser Pro Gln Ala
    450                 455                 460
```

-continued

```
Leu Trp Ser Ala Ala His Glu Ser Leu Pro Ile Thr Phe Val Val Phe
465                 470                 475                 480

Asn Asn Ser Glu Tyr Asn Ile Leu Lys Asn Phe Met Arg Ser Arg Pro
                485                 490                 495

Gly Tyr Asn Ala Gln Ser Gly Arg Phe Val Gly Met Glu Ile Asn Gln
            500                 505                 510

Pro Ser Ile Asp Phe Cys Ala Leu Ala Arg Ser Met Gly Val Asp Ala
        515                 520                 525

Val Arg Leu Thr Glu Pro Asp Asp Ile Thr Ala Tyr Met Ile Ala Ala
    530                 535                 540

Gly Asp Arg Glu Gly Pro Ser Leu Leu Glu Ile Pro Ile Ala Ala Thr
545                 550                 555                 560

Ala Ser

<210> SEQ ID NO 18
<211> LENGTH: 548
<212> TYPE: PRT
<213> ORGANISM: Artificial Sequence
<220> FEATURE:
<223> OTHER INFORMATION: Synthetic enzyme comprising 2-ketoacid
      decarboxylase activity
<220> FEATURE:
<221> NAME/KEY: MISC_FEATURE
<222> LOCATION: (402)..(402)
<223> OTHER INFORMATION: Xaa can be any naturally occurring amino acid
<220> FEATURE:
<221> NAME/KEY: MISC_FEATURE
<222> LOCATION: (538)..(538)
<223> OTHER INFORMATION: Xaa can be any naturally occurring amino acid
<220> FEATURE:
<221> NAME/KEY: MISC_FEATURE
<222> LOCATION: (542)..(542)
<223> OTHER INFORMATION: Xaa can be any naturally occurring amino acid

<400> SEQUENCE: 18

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190
```

```
Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
        210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Xaa Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Xaa Gly Lys Leu Xaa Ala Glu
530                 535                 540

Gln Asn Lys Ser
545

<210> SEQ ID NO 19
<211> LENGTH: 536
<212> TYPE: PRT
<213> ORGANISM: Artificial Sequence
<220> FEATURE:
<223> OTHER INFORMATION: Synthetic mutant of GEO175

<400> SEQUENCE: 19
```

```
Met Arg Thr Val Arg Glu Ser Ala Leu Asp Val Leu Arg Ala Arg Gly
1               5                   10                  15
Met Thr Thr Val Phe Gly Asn Pro Gly Ser Thr Glu Leu Pro Met Leu
                20                  25                  30
Lys Gln Phe Pro Asp Asp Phe Arg Tyr Val Leu Gly Leu Gln Glu Ala
            35                  40                  45
Val Val Val Gly Met Ala Asp Gly Phe Ala Leu Ala Ser Gly Thr Thr
        50                  55                  60
Gly Leu Val Asn Leu His Thr Gly Pro Gly Thr Gly Asn Ala Met Gly
65                  70                  75                  80
Ala Ile Leu Asn Ala Arg Ala Asn Arg Thr Pro Met Val Val Thr Ala
                85                  90                  95
Gly Gln Gln Val Arg Ala Met Leu Thr Met Glu Ala Leu Leu Thr Asn
            100                 105                 110
Pro Gln Ser Thr Leu Leu Pro Gln Pro Ala Val Lys Trp Ala Tyr Glu
        115                 120                 125
Pro Pro Arg Ala Ala Asp Val Ala Pro Ala Leu Ala Arg Ala Val Gln
    130                 135                 140
Val Ala Glu Thr Pro Pro Gln Gly Pro Val Phe Val Ser Leu Pro Met
145                 150                 155                 160
Asp Asp Phe Asp Val Val Leu Gly Glu Asp Glu Asp Arg Ala Ala Gln
                165                 170                 175
Arg Ala Ala Ala Arg Thr Val Thr His Ala Ala Ala Pro Ser Ala Glu
            180                 185                 190
Val Val Arg Arg Leu Ala Ala Arg Leu Ser Gly Ala Arg Ser Ala Val
        195                 200                 205
Leu Val Ala Gly Asn Asp Val Asp Ala Ser Gly Ala Trp Asp Ala Val
    210                 215                 220
Val Glu Leu Ala Glu Arg Thr Gly Leu Pro Val Trp Ser Ala Pro Ser
225                 230                 235                 240
Glu Gly Arg Val Ala Phe Pro Lys Ser His Pro Gln Tyr Arg Gly Met
                245                 250                 255
Leu Pro Pro Ala Ile Ala Pro Leu Ser Arg Cys Leu Glu Gly His Asp
            260                 265                 270
Leu Val Leu Val Ile Gly Ala Pro Val Phe Cys Tyr Tyr Pro Tyr Val
        275                 280                 285
Pro Gly Ala His Leu Pro Glu Asn Thr Glu Leu Val His Leu Thr Arg
    290                 295                 300
Asp Ala Asp Glu Ala Ala Arg Ala Pro Val Gly Asp Ala Val Val Ala
305                 310                 315                 320
Asp Leu Ala Leu Thr Val Arg Ala Leu Leu Ala Glu Leu Pro Ala Arg
                325                 330                 335
Glu Ala Ala Pro Ala Ala Arg Thr Ala Arg Ala Glu Ser Thr Ala
            340                 345                 350
Glu Val Asp Gly Val Leu Thr Pro Leu Ala Ala Met Thr Ala Ile Ala
        355                 360                 365
Gln Gly Ala Pro Ala Asn Thr Thr Trp Val Asn Glu Ser Pro Ser Asn
    370                 375                 380
Leu Gly Gln Phe His Asp Ala Thr Arg Ile Asp Thr Pro Gly Ser Phe
385                 390                 395                 400
Leu Phe Thr Ala Gly Gly Gly Leu Gly Phe Gly Leu Ala Ala Ala Val
                405                 410                 415
Gly Ala Gln Leu Gly Ala Pro Asp Arg Pro Val Val Cys Val Ile Gly
```

```
            420                 425                 430
Asp Gly Ser Thr His Tyr Ala Val Gln Ala Leu Trp Thr Ala Ala
        435                 440                 445
Tyr Lys Val Pro Val Thr Phe Val Val Leu Ser Asn Gln Arg Tyr Ala
        450                 455                 460
Ile Leu Gln Trp Phe Ala Gln Val Glu Gly Ala Gln Gly Ala Pro Gly
465                 470                 475                 480
Leu Asp Ile Pro Gly Leu Asp Ile Ala Ala Val Ala Thr Gly Tyr Gly
                485                 490                 495
Val Arg Ala His Arg Ala Thr Gly Phe Gly Glu Leu Ser Lys Leu Val
                500                 505                 510
Arg Glu Ser Ala Leu Gln Gln Asp Gly Pro Val Leu Ile Asp Val Pro
                515                 520                 525
Val Thr Thr Glu Leu Pro Thr Leu
                530                 535

<210> SEQ ID NO 20
<211> LENGTH: 542
<212> TYPE: PRT
<213> ORGANISM: Pseudomonas putida

<400> SEQUENCE: 20

Met Ala Ser Val His Gly Thr Thr Tyr Glu Leu Leu Arg Arg Gln Gly
1               5                   10                  15
Ile Asp Thr Val Phe Gly Asn Pro Gly Ser Asn Glu Leu Pro Phe Leu
                20                  25                  30
Lys Asp Phe Pro Glu Asp Phe Arg Tyr Ile Leu Ala Leu Gln Glu Ala
            35                  40                  45
Cys Val Val Gly Ile Ala Asp Gly Tyr Ala Gln Ala Ser Arg Lys Pro
        50                  55                  60
Ala Phe Ile Asn Leu His Ser Ala Ala Gly Thr Gly Asn Ala Met Gly
65                  70                  75                  80
Ala Leu Ser Asn Ala Trp Asn Ser His Ser Pro Leu Ile Val Thr Ala
                85                  90                  95
Gly Gln Gln Thr Arg Ala Met Ile Gly Val Glu Ala Leu Leu Thr Asn
                100                 105                 110
Val Asp Ala Ala Asn Leu Pro Arg Pro Leu Val Lys Trp Ser Tyr Glu
            115                 120                 125
Pro Ala Ser Ala Ala Glu Val Pro His Ala Met Ser Arg Ala Ile His
        130                 135                 140
Met Ala Ser Met Ala Pro Gln Gly Pro Val Tyr Leu Ser Val Pro Tyr
145                 150                 155                 160
Asp Asp Trp Asp Lys Asp Ala Asp Pro Gln Ser His His Leu Phe Asp
                165                 170                 175
Arg His Val Ser Ser Ser Val Arg Leu Asn Asp Gln Asp Leu Asp Ile
                180                 185                 190
Leu Val Lys Ala Leu Asn Ser Ala Ser Asn Pro Ala Ile Val Leu Gly
            195                 200                 205
Pro Asp Val Asp Ala Ala Asn Ala Asn Ala Asp Cys Val Met Leu Ala
        210                 215                 220
Glu Arg Leu Lys Ala Pro Val Trp Val Ala Pro Ser Ala Pro Arg Cys
225                 230                 235                 240
Pro Phe Pro Thr Arg His Pro Cys Phe Arg Gly Leu Met Pro Ala Gly
                245                 250                 255
```

```
Ile Ala Ala Ile Ser Gln Leu Leu Glu Gly His Asp Val Val Leu Val
                260                 265                 270

Ile Gly Ala Pro Val Phe Arg Tyr His Gln Tyr Asp Pro Gly Gln Tyr
            275                 280                 285

Leu Lys Pro Gly Thr Arg Leu Ile Ser Val Thr Cys Asp Pro Leu Glu
        290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
            340                 345                 350

Leu His Pro Glu Thr Val Phe Asp Thr Leu Asn Asp Met Ala Pro Glu
        355                 360                 365

Asn Ala Ile Tyr Leu Asn Glu Ser Thr Ser Thr Ala Gln Met Trp
370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
        435                 440                 445

Ile Phe Val Ile Met Asn Asn Gly Thr Tyr Gly Ala Leu Arg Trp Phe
450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
                485                 490                 495

Ala Asp Asn Leu Glu Gln Leu Lys Gly Ser Leu Gln Glu Ala Leu Ser
            500                 505                 510

Ala Lys Gly Pro Val Leu Ile Glu Val Ser Thr Val Ser Pro Val Lys
        515                 520                 525

Gly Ser Thr Glu Asn Leu Tyr Phe Gln Ser Gly Ala Leu Glu
    530                 535                 540

<210> SEQ ID NO 21
<211> LENGTH: 572
<212> TYPE: PRT
<213> ORGANISM: Acetobacter pasteurianus

<400> SEQUENCE: 21

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95
```

```
Ile Ser Gly Ala Pro Asn Ser Asn Asp Gln Gly Thr Gly His Ile Leu
            100                 105                 110
His His Thr Ile Gly Lys Thr Asp Tyr Ser Tyr Gln Leu Glu Met Ala
            115                 120                 125
Arg Gln Val Thr Cys Ala Ala Glu Ser Ile Thr Asp Ala His Ser Ala
130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
            180                 185                 190
Thr Ser Leu Lys Ala Ala Val Asp Ala Thr Val Ala Leu Leu Glu Lys
            195                 200                 205
Ser Ala Ser Pro Val Met Leu Leu Gly Ser Lys Leu Arg Ala Ala Asn
210                 215                 220
Ala Leu Ala Ala Thr Glu Thr Leu Ala Asp Lys Leu Gln Cys Ala Val
225                 230                 235                 240
Thr Ile Met Ala Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
            275                 280                 285
Asp Tyr Ser Thr Val Gly Trp Ser Ala Trp Pro Lys Gly Pro Asn Val
            290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
            355                 360                 365
His Ile Asn Ala Leu Leu Thr Ser Asn Thr Thr Leu Val Ala Glu Thr
            370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
            435                 440                 445
Met Val Arg Tyr Glu Leu Pro Val Ile Ile Phe Leu Ile Asn Asn Arg
450                 455                 460
Gly Tyr Val Ile Glu Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Gly Leu Thr Glu
            500                 505                 510
```

-continued

```
Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Trp Gly
            530                 535                 540

Arg Lys Val Ala Ser Thr Asn Ala Arg Lys Thr Thr Leu Ala Gly Ser
545                 550                 555                 560

Thr Glu Asn Leu Tyr Phe Gln Ser Gly Ala Leu Glu
                565                 570

<210> SEQ ID NO 22
<211> LENGTH: 582
<212> TYPE: PRT
<213> ORGANISM: Zymomonas mobilis

<400> SEQUENCE: 22

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Asp Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Thr Asp Ala Leu Gly Gly Ala Val
225                 230                 235                 240

Ala Thr Met Ala Ala Lys Ser Phe Phe Pro Glu Glu Asn Ala Leu
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Ile Arg Phe Pro
305                 310                 315                 320
```

Ser Val His Leu Lys Asp Tyr Leu Thr Arg Leu Ala Gln Lys Val Ser
            325                 330                 335

Lys Lys Thr Gly Ser Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
            355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
            405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
            435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
            485                 490                 495

Asn Gly Asn Gly Gly Tyr Asp Ser Gly Ala Ala Lys Gly Leu Lys Ala
            500                 505                 510

Lys Thr Gly Gly Glu Leu Ala Glu Ala Ile Lys Val Ala Leu Ala Asn
            515                 520                 525

Thr Asp Gly Pro Thr Leu Ile Glu Cys Phe Ile Gly Arg Glu Asp Cys
            530                 535                 540

Thr Glu Glu Leu Val Lys Trp Gly Lys Arg Val Ala Ala Ala Asn Ser
545                 550                 555                 560

Arg Lys Pro Val Asn Lys Val Val Gly Ser Thr Glu Asn Leu Tyr Phe
            565                 570                 575

Gln Ser Gly Ala Leu Glu
            580

<210> SEQ ID NO 23
<211> LENGTH: 591
<212> TYPE: PRT
<213> ORGANISM: Rheinheimera sp. A13L

<400> SEQUENCE: 23

Met Ser Ser Ile Asn Ser Phe Thr Val Ala Asp Tyr Leu Leu Thr Arg
1               5                   10                  15

Leu His Gln Leu Gly Leu Arg Lys Val Phe Gln Val Pro Gly Asp Tyr
            20                  25                  30

Val Ala Asn Phe Met Asp Ala Leu Glu Gln Phe Asn Gly Ile Glu Ala
            35                  40                  45

Val Gly Asp Leu Thr Glu Leu Gly Ala Gly Tyr Ala Ala Asp Gly Tyr
    50                  55                  60

Ala Arg Leu Thr Gly Ile Gly Ala Val Ser Val Gln Phe Gly Val Gly
65                  70                  75                  80

Thr Phe Ser Val Leu Asn Ala Ile Ala Gly Ser Tyr Val Glu Arg Asn
            85                  90                  95

Pro Val Val Val Ile Thr Ala Ser Pro Ser Thr Gly Asn Arg Lys Thr

```
                100                 105                 110
Ile Lys Glu Thr Gly Val Leu Phe His His Ser Thr Gly Asp Leu Leu
            115                 120                 125

Ala Asp Ser Lys Val Phe Ala Asn Val Thr Val Ala Ala Glu Val Leu
        130                 135                 140

Ser Asp Pro Ser Asp Ala Arg Gln Lys Ile Asp Lys Ala Leu Thr Leu
145                 150                 155                 160

Ala Ile Thr Phe Arg Arg Pro Ile Tyr Leu Glu Ala Trp Gln Asp Val
                165                 170                 175

Trp Gly Leu Ala Cys Glu Lys Pro Glu Gly Glu Leu Lys Ala Leu Pro
            180                 185                 190

Leu Ile Ser Glu Glu Gly Ala Leu Lys Ala Met Leu Ala Asp Ser Leu
        195                 200                 205

Lys Leu Leu Asn Ser Ala Arg Gln Pro Leu Val Leu Leu Gly Val Glu
    210                 215                 220

Ile Asn Arg Phe Gly Leu Gln Asp Ala Val Leu Asp Leu Leu Lys Ala
225                 230                 235                 240

Ser Gly Leu Pro Tyr Ser Thr Thr Ser Leu Ala Lys Thr Val Ile Ser
                245                 250                 255

Glu Asn Glu Gly Ile Phe Val Gly Thr Tyr Ala Asp Gly Ala Ser Phe
            260                 265                 270

Pro Ala Thr Val Glu Tyr Ile Glu Lys Ala Asp Cys Val Leu Ala Leu
        275                 280                 285

Gly Val Ile Phe Thr Asp Asp Tyr Leu Thr Met Leu Ser Lys Gln Phe
    290                 295                 300

Asp Gln Met Ile Val Val Asn Asn Asp Glu Thr Ser Arg Leu Gly His
305                 310                 315                 320

Ala Tyr Tyr His Gln Leu Tyr Leu Ala Asp Phe Ile Leu Gln Leu Thr
                325                 330                 335

Asp Glu Ile Lys Lys Ser Ser Leu Tyr Pro Arg Gln Asn Ser Ala Leu
            340                 345                 350

Pro Leu Leu Pro Pro Gln Pro Gln Ile Thr Pro Ala Leu Leu Gln Gln
        355                 360                 365

Gln Leu Ser Tyr Gln Asn Phe Phe Asp Leu Phe Tyr Gly Tyr Leu Leu
    370                 375                 380

Gln His Gln Leu Gln Asp Asn Ile Ser Leu Ile Leu Gly Glu Ser Ser
385                 390                 395                 400

Ser Leu Tyr Met Ser Ala Arg Leu Tyr Gly Leu Pro Gln Asp Ser Phe
                405                 410                 415

Ile Ala Asp Ala Ala Trp Gly Ser Leu Gly His Glu Thr Gly Cys Val
            420                 425                 430

Thr Gly Ile Ala Tyr Ala Ser Asp Lys Arg Ala Met Ala Ile Ala Gly
        435                 440                 445

Asp Gly Gly Phe Met Met Met Cys Gln Cys Leu Ser Thr Ile Ser Arg
    450                 455                 460

His Gln Leu Asn Ser Val Val Phe Val Ile Ser Asn Lys Val Tyr Ala
465                 470                 475                 480

Ile Glu Gln Ser Phe Val Asp Ile Cys Ala Phe Ala Lys Gly His
                485                 490                 495

Phe Ala Pro Phe Asp Leu Leu Pro Thr Trp Asp Tyr Leu Ser Leu Ala
            500                 505                 510

Lys Ala Phe Ser Val Glu Gly Tyr Arg Val Gln Asn Gly Glu Glu Leu
        515                 520                 525
```

```
Leu Gln Ala Leu Glu His Ile Met Thr Gln Lys Asp Lys Pro Ala Leu
            530                 535                 540

Val Glu Val Val Ile Gln Ser Gln Asp Leu Ala Pro Ala Met Ala Gly
545                 550                 555                 560

Leu Val Lys Ser Ile Thr Gly His Thr Val Glu Gln Cys Ala Ile Pro
                565                 570                 575

Thr Gly Ser Thr Glu Asn Leu Tyr Phe Gln Ser Gly Ala Leu Glu
            580                 585                 590

<210> SEQ ID NO 24
<211> LENGTH: 543
<212> TYPE: PRT
<213> ORGANISM: Unknown
<220> FEATURE:
<223> OTHER INFORMATION: Bacterial

<400> SEQUENCE: 24

Met Thr Thr Val His Ala Ala Tyr Glu Leu Leu Arg Ser Asn Arg
1               5                   10                  15

Leu Thr Thr Ile Phe Gly Asn Pro Gly Asp Asn Glu Leu Pro Phe Leu
            20                  25                  30

Asp Ala Met Pro Ala Asp Phe Arg Tyr Ile Leu Gly Leu His Glu Gly
        35                  40                  45

Val Val Val Gly Met Ala Asp Gly Phe Ala Gln Ala Ser Gly Gln Ala
50                  55                  60

Ala Phe Val Asn Leu His Ala Ala Ser Gly Thr Gly Asn Ala Met Gly
65                  70                  75                  80

Ala Leu Thr Asn Ala Trp Tyr Ser His Thr Pro Leu Val Ile Thr Ala
                85                  90                  95

Gly Gln Gln Val Arg Pro Met Ile Gly Leu Glu Ala Met Leu Ser Asn
            100                 105                 110

Val Asp Ala Ala Ser Leu Pro Arg Pro Leu Val Lys Trp Ser Ala Glu
        115                 120                 125

Pro Ala Gln Ala Pro Asp Val Pro Arg Ala Leu Ser Gln Ala Ile His
130                 135                 140

Thr Ala Thr Ser Asp Pro Lys Gly Pro Val Tyr Leu Ser Ile Pro Tyr
145                 150                 155                 160

Asp Asp Trp Asn Gln Asp Thr Gly Asn Leu Ser Glu His Leu Ser Ser
                165                 170                 175

Arg Ser Val Ser Arg Ala Gly Asn Pro Ser Ala Glu Gln Leu Asp Asp
            180                 185                 190

Ile Leu Ser Ala Leu Arg Glu Ala Asn Pro Ala Leu Val Phe Gly
        195                 200                 205

Pro Asp Val Asp Ala Ala Arg Ala Asn His His Ala Val Arg Leu Ala
210                 215                 220

Glu Lys Leu Ala Ala Pro Val Trp Ile Ala Pro Ala Ala Pro Arg Cys
225                 230                 235                 240

Pro Phe Pro Thr Arg His Pro Asn Phe Arg Gly Val Leu Pro Ala Ser
                245                 250                 255

Ile Ala Gly Ile Ser Ala Leu Leu Asn Gly His Asp Leu Ile Val Val
            260                 265                 270

Ile Gly Ala Pro Val Phe Arg Tyr His Gln Tyr Gln Pro Gly Ser Tyr
        275                 280                 285

Leu Pro Glu Asn Ser Arg Leu Ile His Ile Thr Cys Asp Ala Gly Glu
290                 295                 300
```

Ala Ala Arg Ala Pro Met Gly Asp Ala Leu Val Ala Asp Ile Gly Gln
305                 310                 315                 320

Thr Leu Arg Ala Leu Ala Asp Ile Ile Pro Gln Ser Lys Arg Pro Pro
                325                 330                 335

Leu Arg Pro Arg Val Ile Pro Pro Val Pro Asp Ser Gln Asp Asp Leu
            340                 345                 350

Leu Ala Pro Asp Ala Val Phe Glu Val Met Asn Glu Val Ala Pro Glu
        355                 360                 365

Asp Val Val Tyr Val Asn Glu Ser Val Ser Thr Val Thr Ala Leu Trp
    370                 375                 380

Glu Arg Val Glu Leu Lys His Pro Gly Ser Tyr Tyr Phe Pro Ala Ser
385                 390                 395                 400

Gly Gly Leu Gly Phe Gly Met Pro Ala Ala Val Gly Val Gln Leu Ala
                405                 410                 415

Asn Asp Arg Arg Arg Val Ile Ala Val Ile Gly Asp Gly Ser Ala Asn
            420                 425                 430

Tyr Gly Ile Thr Ala Leu Trp Thr Ala Ala Gln Glu Lys Ile Pro Val
        435                 440                 445

Val Phe Ile Ile Leu Asn Asn Gly Thr Tyr Gly Ala Leu Arg Ala Phe
    450                 455                 460

Ala Lys Leu Leu Asn Ala Glu Asn Ala Ala Gly Leu Asp Val Pro Gly
465                 470                 475                 480

Ile Cys Phe Cys Ala Ile Ala Glu Gly Tyr Gly Val Glu Ala His Arg
                485                 490                 495

Ile Thr Ser Leu Glu Asn Phe Lys Asp Lys Leu Ser Ala Ala Leu Gln
            500                 505                 510

Ser Asp Thr Pro Thr Leu Leu Glu Val Pro Thr Ser Thr Thr Ser Pro
        515                 520                 525

Phe Gly Ser Thr Glu Asn Leu Tyr Phe Gln Ser Gly Ala Leu Glu
    530                 535                 540

<210> SEQ ID NO 25
<211> LENGTH: 543
<212> TYPE: PRT
<213> ORGANISM: Unknown
<220> FEATURE:
<223> OTHER INFORMATION: Bacterial

<400> SEQUENCE: 25

Met Lys Thr Ile His Ser Ala Ala Tyr Ala Leu Leu Arg Arg His Gly
1               5                   10                  15

Met Thr Thr Ile Phe Gly Asn Pro Gly Ser Asn Glu Leu Pro Phe Leu
            20                  25                  30

Lys Ser Phe Pro Glu Asp Phe Gln Tyr Val Leu Gly Leu His Glu Gly
        35                  40                  45

Ala Val Val Gly Met Ala Asp Gly Tyr Ala Leu Ala Ser Gly Lys Pro
    50                  55                  60

Ala Phe Val Asn Leu His Ala Ala Gly Thr Gly Asn Gly Met Gly
65                  70                  75                  80

Ala Leu Thr Asn Ser Trp Tyr Ser His Ser Pro Leu Val Ile Thr Ala
                85                  90                  95

Gly Gln Gln Val Arg Pro Met Ile Gly Val Glu Ala Met Leu Ala Asn
            100                 105                 110

Val Asp Ala Thr Gln Leu Pro Lys Pro Leu Val Lys Trp Ser Tyr Glu
        115                 120                 125

-continued

```
Pro Ala Asn Ala Gln Asp Val Pro Arg Ala Leu Ser Gln Ala Ile His
    130                 135                 140

Tyr Ala Asn Thr Thr Pro Lys Ala Pro Val Tyr Leu Ser Ile Pro Tyr
145                 150                 155                 160

Asp Asp Trp Asp Gln Pro Ser Gly Pro Gly Val Glu His Leu Ile Glu
                165                 170                 175

Arg Asp Val Gln Thr Ala Gly Thr Pro Asp Ala Arg Gln Leu Gln Val
                180                 185                 190

Leu Val Gln Gln Val Gln Asp Ala Arg Asn Pro Val Leu Val Leu Gly
            195                 200                 205

Pro Asp Val Asp Ala Thr Leu Ser Asn Asp His Ala Val Ala Leu Ala
    210                 215                 220

Asp Lys Leu Arg Met Pro Val Trp Ile Ala Pro Ala Ala Ser Arg Cys
225                 230                 235                 240

Pro Phe Pro Thr Arg His Pro Ser Phe Arg Gly Val Leu Pro Ala Ala
                245                 250                 255

Ile Ala Gly Ile Ser Lys Thr Leu Gln Gly His Asp Leu Ile Ile Val
                260                 265                 270

Val Gly Ala Pro Val Phe Arg Tyr Leu Gln Phe Ala Pro Gly Asp Tyr
            275                 280                 285

Leu Pro Val Gly Ala Gln Leu Leu His Ile Thr Ser Asp Pro Leu Glu
    290                 295                 300

Ala Thr Arg Ala Pro Met Gly His Ala Leu Val Gly Asp Ile Arg Glu
305                 310                 315                 320

Thr Leu Arg Val Leu Ala Glu Glu Val Val Gln Ser Arg Pro Tyr
                325                 330                 335

Pro Glu Ala Leu Ala Ala Pro Glu Cys Val Thr Asp Glu Pro His His
                340                 345                 350

Leu His Pro Glu Thr Leu Phe Asp Val Leu Asp Ala Val Ala Pro His
            355                 360                 365

Asp Ala Ile Tyr Val Lys Glu Ser Thr Ser Thr Val Thr Ala Phe Trp
    370                 375                 380

Gln Arg Met Asn Leu Arg His Pro Gly Ser Tyr Tyr Phe Pro Ala Ala
385                 390                 395                 400

Gly Gly Leu Gly Phe Gly Leu Pro Ala Ala Val Gly Val Gln Leu Ala
                405                 410                 415

Gln Pro Gln Arg Arg Val Val Ala Leu Ile Gly Asp Gly Ser Ala Asn
                420                 425                 430

Tyr Gly Ile Thr Ala Leu Trp Thr Ala Ala Gln Tyr Arg Ile Pro Val
            435                 440                 445

Val Phe Ile Ile Leu Lys Asn Gly Thr Tyr Gly Ala Leu Arg Trp Phe
    450                 455                 460

Ala Gly Val Leu Lys Ala Glu Asp Ser Pro Gly Leu Asp Val Pro Gly
465                 470                 475                 480

Leu Asp Phe Cys Ala Ile Ala Lys Gly Tyr Gly Val Lys Ala Val His
                485                 490                 495

Thr Asp Thr Arg Asp Ser Phe Glu Ala Ala Leu Arg Thr Ala Leu Asp
                500                 505                 510

Ala Asn Glu Pro Thr Val Ile Glu Val Pro Thr Leu Thr Ile Gln Pro
            515                 520                 525

His Gly Ser Thr Glu Asn Leu Tyr Phe Gln Ser Gly Ala Leu Glu
    530                 535                 540
```

<210> SEQ ID NO 26
<211> LENGTH: 566
<212> TYPE: PRT
<213> ORGANISM: Enterobacter cloacae

<400> SEQUENCE: 26

```
Met Arg Thr Pro Tyr Cys Val Ala Asp Tyr Leu Leu Asp Arg Leu Thr
1               5                   10                  15

Asp Cys Gly Ala Asp His Leu Phe Gly Val Pro Gly Asp Tyr Asn Leu
            20                  25                  30

Gln Phe Leu Asp His Val Ile Asp Ser Pro Asp Ile Cys Trp Val Gly
        35                  40                  45

Cys Ala Asn Glu Leu Asn Ala Ser Tyr Ala Ala Asp Gly Tyr Ala Arg
50                  55                  60

Cys Lys Gly Phe Ala Ala Leu Leu Thr Thr Phe Gly Val Gly Glu Leu
65                  70                  75                  80

Ser Ala Met Asn Gly Ile Ala Gly Ser Tyr Ala Glu His Val Pro Val
                85                  90                  95

Leu His Ile Val Gly Ala Pro Gly Thr Ala Ala Gln Gln Arg Gly Glu
            100                 105                 110

Leu Leu His His Thr Leu Gly Asp Gly Glu Phe Arg His Phe Tyr His
        115                 120                 125

Met Ser Glu Pro Ile Thr Val Ala Gln Ala Val Leu Thr Glu Gln Asn
130                 135                 140

Ala Cys Tyr Glu Ile Asp Arg Val Leu Thr Thr Met Leu Arg Glu Arg
145                 150                 155                 160

Arg Pro Gly Tyr Leu Met Leu Pro Ala Asp Val Ala Lys Lys Ala Ala
                165                 170                 175

Thr Pro Pro Val Asn Ala Leu Thr His Lys Gln Ala His Ala Asp Ser
            180                 185                 190

Ala Cys Leu Lys Ala Phe Arg Asp Ala Ala Glu Asn Lys Leu Ala Met
        195                 200                 205

Ser Lys Arg Thr Ala Leu Leu Ala Asp Phe Leu Val Leu Arg His Gly
210                 215                 220

Leu Lys His Ala Leu Gln Lys Trp Val Lys Glu Val Pro Met Ala His
225                 230                 235                 240

Ala Thr Met Leu Met Gly Lys Gly Ile Phe Asp Glu Arg Gln Ala Gly
                245                 250                 255

Phe Tyr Gly Thr Tyr Ser Gly Ser Ala Ser Thr Gly Ala Val Lys Glu
            260                 265                 270

Ala Ile Glu Gly Ala Asp Thr Val Leu Cys Val Gly Thr Arg Phe Thr
        275                 280                 285

Asp Thr Leu Thr Ala Gly Phe Thr His Gln Leu Thr Pro Ala Gln Thr
290                 295                 300

Ile Glu Val Gln Pro His Ala Ala Arg Val Gly Asp Val Trp Phe Thr
305                 310                 315                 320

Gly Ile Pro Met Asn Gln Ala Ile Glu Thr Leu Val Glu Leu Cys Lys
                325                 330                 335

Gln His Val His Ala Gly Leu Met Ser Ser Ser Gly Ala Ile Pro
            340                 345                 350

Phe Pro Gln Pro Asp Gly Ser Leu Thr Gln Glu Asn Phe Trp Arg Thr
        355                 360                 365

Leu Gln Thr Phe Ile Arg Pro Gly Asp Ile Ile Leu Ala Asp Gln Gly
370                 375                 380
```

```
Thr Ser Ala Phe Gly Ala Ile Asp Leu Arg Leu Pro Ala Asp Val Asn
385                 390                 395                 400

Phe Ile Val Gln Pro Leu Trp Gly Ser Ile Gly Tyr Thr Leu Ala Ala
                405                 410                 415

Ala Phe Gly Ala Gln Thr Ala Cys Pro Asn Arg Arg Val Ile Val Leu
            420                 425                 430

Thr Gly Asp Gly Ala Ala Gln Leu Thr Ile Gln Glu Leu Gly Ser Met
        435                 440                 445

Leu Arg Asp Lys Gln His Pro Ile Ile Leu Val Leu Asn Asn Glu Gly
    450                 455                 460

Tyr Thr Val Glu Arg Ala Ile His Gly Ala Glu Gln Arg Tyr Asn Asp
465                 470                 475                 480

Ile Ala Leu Trp Asn Trp Thr His Ile Pro Gln Ala Leu Ser Leu Asp
                485                 490                 495

Pro Gln Ser Glu Cys Trp Arg Val Ser Glu Ala Glu Gln Leu Ala Asp
            500                 505                 510

Val Leu Glu Lys Val Ala His His Glu Arg Leu Ser Leu Ile Glu Val
        515                 520                 525

Met Leu Pro Lys Ala Asp Ile Pro Pro Leu Leu Gly Ala Leu Thr Lys
    530                 535                 540

Ala Leu Glu Ala Cys Asn Asn Ala Gly Ser Thr Glu Asn Leu Tyr Phe
545                 550                 555                 560

Gln Ser Gly Ala Leu Glu
                565

<210> SEQ ID NO 27
<211> LENGTH: 531
<212> TYPE: PRT
<213> ORGANISM: Unknown
<220> FEATURE:
<223> OTHER INFORMATION: Bacterial

<400> SEQUENCE: 27

Met Gly Ala His Tyr Pro Met Ser Gly Glu Ser Thr Val His Asp Val
1               5                   10                  15

Thr Tyr Gln Leu Leu Arg Ser Leu Gly Ile Thr Thr Val Phe Gly Asn
                20                  25                  30

Pro Gly Ser Thr Glu Gln Thr Phe Leu Gln Asp Phe Pro Ser Asp Phe
            35                  40                  45

Thr Tyr Val Leu Gly Leu Gln Glu Ala Ser Val Met Ala Met Ala Asp
        50                  55                  60

Ala Phe Ala Gln Val Thr Arg Arg Pro Ala Leu Val Asn Leu His Ser
65                  70                  75                  80

Ser Ala Gly Val Gly His Ser Ile Gly Asn Leu Val Ser Ala Phe Asp
                85                  90                  95

Ala His Thr Pro Leu Ile Val Thr Ala Gly Gln Gln His Arg Glu Met
            100                 105                 110

Val Ile Gly Glu Pro Ala Leu Ser Asn Arg Glu Ala Thr Asn Leu Pro
        115                 120                 125

Arg Pro Trp Val Lys Trp Ser Tyr Glu Pro Ala Arg Ala Gln Asp Val
    130                 135                 140

Pro Glu Ala Phe Met Arg Ala Cys Ala Ile Ala Thr Gln Pro Pro Ala
145                 150                 155                 160

Gly Pro Val Phe Leu Ser Ile Pro Leu Asp Asp Trp Asn Ala Pro Met
                165                 170                 175
```

```
Thr Gly Pro Ala Val Val Arg Ser Val Ser Thr Val Cys Ala Pro Glu
            180                 185                 190

Thr Glu Arg Leu Arg Gly Phe Ala Arg Arg Ile Arg Ala Ser Gln Arg
            195                 200                 205

Pro Val Leu Val Phe Gly Pro Glu Val Asp Arg Ser Gly Gly Trp His
            210                 215                 220

Ala Ala Ile Ala Leu Ala Glu Asn Leu Gly Val Pro Val Phe Gly Ala
225                 230                 235                 240

Ala Gly Pro Asp Arg Val Ser Phe Pro Glu Asp His Pro Leu Phe Gln
            245                 250                 255

Gly Arg Leu Gly Met Ser Gln Lys Ser Val Ser Asp Arg Leu Thr Gly
            260                 265                 270

Tyr Asp Leu Val Val Ile Gly Ala Ala Val Phe Arg Tyr Tyr Pro
            275                 280                 285

His Val Pro Gly Asp Ile Leu Pro Ala Gly Thr Glu Leu Leu His Ile
            290                 295                 300

Thr Gly Asp Pro Ala Val Ala Gly Ala Ala Arg Val Gly Asp Ser Val
305                 310                 315                 320

Leu Gly Asp Ala Arg Leu Ala Ile Glu Leu Leu Thr Glu Leu Leu Asp
            325                 330                 335

Ala Glu Ala Ala His Ser Pro Arg Arg Pro Gln His Gln His Pro His
            340                 345                 350

Pro Gln Pro Gln His Val Glu His Val Gln His Gln Pro Pro Gln
            355                 360                 365

Thr Arg Phe Gln Ala Arg Ala Gln Pro Arg Pro Arg His Ala Pro
            370                 375                 380

Asp Arg Pro Glu Thr Ala Gly Gly Pro Leu Cys Ala Asp Glu Val His
385                 390                 395                 400

Ala Val Ile Asn Ala Ser Arg Pro Arg Asn Ala Ala Leu Val Tyr Glu
            405                 410                 415

Ser Thr Ser Thr Ile Gly Glu Gln Val Glu Trp Leu Pro Val Ile Glu
            420                 425                 430

Pro Ala Ser Phe Phe Ala Asn Ala Ser Gly Gly Leu Gly Trp Ala Val
            435                 440                 445

Pro Ala Ala Val Gly Val Ala Leu Gly Asp Arg Asp Arg Gly Val His
450                 455                 460

Arg Pro Val Ile Gly Ile Ile Gly Asp Gly Ala Phe Gln Tyr Ser Val
465                 470                 475                 480

Gln Ala Leu Trp Thr Ala Thr Gln His Ser Leu Pro Ile Val Phe Val
            485                 490                 495

Val Leu Arg His Glu Tyr Ser Ile Leu Lys Ser Phe Ala Glu Leu Glu
            500                 505                 510

Arg Thr Ala Gly Val Gly Ser Thr Glu Asn Leu Tyr Phe Gln Ser Gly
            515                 520                 525

Ala Leu Glu
    530

<210> SEQ ID NO 28
<211> LENGTH: 550
<212> TYPE: PRT
<213> ORGANISM: Streptomyces sp. C

<400> SEQUENCE: 28

Met Arg Thr Val Arg Glu Ser Ala Leu Asp Val Leu Arg Ala Arg Gly
```

-continued

```
1               5                   10                  15
Met Thr Thr Val Phe Gly Asn Pro Gly Ser Thr Glu Leu Pro Met Leu
                20                  25                  30
Lys Gln Phe Pro Asp Asp Phe Arg Tyr Val Leu Gly Leu Gln Glu Ala
                35                  40                  45
Val Val Val Gly Met Ala Asp Gly Phe Ala Leu Ala Ser Gly Thr Thr
 50                  55                  60
Gly Leu Val Asn Leu His Thr Gly Pro Gly Thr Gly Asn Ala Met Gly
 65                  70                  75                  80
Ala Ile Leu Asn Ala Arg Ala Asn Arg Thr Pro Met Val Val Thr Ala
                85                  90                  95
Gly Gln Gln Val Arg Ala Met Leu Thr Met Glu Ala Leu Leu Thr Asn
                100                 105                 110
Pro Gln Ser Thr Leu Leu Pro Gln Pro Ala Val Lys Trp Ala Tyr Glu
                115                 120                 125
Pro Pro Arg Ala Ala Asp Val Ala Pro Ala Leu Ala Arg Ala Val Gln
                130                 135                 140
Val Ala Glu Thr Pro Pro Gln Gly Pro Val Phe Val Ser Leu Pro Met
145                 150                 155                 160
Asp Asp Phe Asp Val Val Leu Gly Glu Asp Glu Arg Ala Ala Gln
                165                 170                 175
Arg Ala Ala Ala Arg Thr Val Thr His Ala Ala Pro Ser Ala Glu
                180                 185                 190
Val Val Arg Arg Leu Ala Ala Arg Leu Ser Gly Ala Arg Ser Ala Val
                195                 200                 205
Leu Val Ala Gly Asn Asp Val Asp Ala Ser Gly Ala Trp Asp Ala Val
 210                 215                 220
Val Glu Leu Ala Glu Arg Thr Gly Leu Pro Val Trp Ser Ala Pro Thr
225                 230                 235                 240
Glu Gly Arg Val Ala Phe Pro Lys Ser His Pro Gln Tyr Arg Gly Met
                245                 250                 255
Leu Pro Pro Ala Ile Ala Pro Leu Ser Arg Cys Leu Glu Gly His Asp
                260                 265                 270
Leu Val Leu Val Ile Gly Ala Pro Val Phe Cys Tyr Tyr Pro Tyr Val
                275                 280                 285
Pro Gly Ala His Leu Pro Glu Asn Thr Glu Leu Val His Leu Thr Arg
                290                 295                 300
Asp Ala Asp Glu Ala Ala Arg Ala Pro Val Gly Asp Ala Val Val Ala
305                 310                 315                 320
Asp Leu Ala Leu Thr Val Arg Ala Leu Leu Ala Glu Leu Pro Ala Arg
                325                 330                 335
Glu Ala Ala Pro Ala Ala Arg Thr Ala Arg Ala Glu Ser Thr Ala
                340                 345                 350
Glu Val Asp Gly Val Leu Thr Pro Leu Ala Ala Met Thr Ala Ile Ala
                355                 360                 365
Gln Gly Ala Pro Ala Asn Thr Leu Trp Val Asn Glu Ser Pro Ser Asn
                370                 375                 380
Leu Gly Gln Phe His Asp Ala Thr Arg Ile Asp Thr Pro Gly Ser Phe
385                 390                 395                 400
Leu Phe Thr Ala Gly Gly Leu Gly Phe Gly Leu Ala Ala Ala Val
                405                 410                 415
Gly Ala Gln Leu Gly Ala Pro Asp Arg Pro Val Val Cys Val Ile Gly
                420                 425                 430
```

Asp Gly Ser Thr His Tyr Ala Val Gln Ala Leu Trp Thr Ala Ala Ala
        435                 440                 445

Tyr Lys Val Pro Val Thr Phe Val Val Leu Ser Asn Gln Arg Tyr Ala
        450                 455                 460

Ile Leu Gln Trp Phe Ala Gln Val Glu Gly Ala Gln Gly Ala Pro Gly
465                 470                 475                 480

Leu Asp Ile Pro Gly Leu Asp Ile Ala Ala Val Ala Thr Gly Tyr Gly
                    485                 490                 495

Val Arg Ala His Arg Ala Thr Gly Phe Gly Glu Leu Ser Lys Leu Val
                500                 505                 510

Arg Glu Ser Ala Leu Gln Gln Asp Gly Pro Val Leu Ile Asp Val Pro
        515                 520                 525

Val Thr Thr Glu Leu Pro Thr Leu Gly Ser Thr Glu Asn Leu Tyr Phe
        530                 535                 540

Gln Ser Gly Ala Leu Glu
545                 550

<210> SEQ ID NO 29
<211> LENGTH: 548
<212> TYPE: PRT
<213> ORGANISM: Unknown
<220> FEATURE:
<223> OTHER INFORMATION: Bacterial

<400> SEQUENCE: 29

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser Arg Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
        210                 215                 220

Val Ser Gln Phe Ile Ser Lys Thr Lys Leu Pro Ile Thr Thr Leu Asn
225                 230                 235                 240

```
Phe Gly Lys Ser Ser Val Asp Glu Ala Leu Pro Ser Phe Leu Gly Ile
            245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
            325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
            530                 535                 540

Gln Asn Lys Ser
545

<210> SEQ ID NO 30
<211> LENGTH: 542
<212> TYPE: PRT
<213> ORGANISM: Unknown
<220> FEATURE:
<223> OTHER INFORMATION: Bacterial

<400> SEQUENCE: 30

Met Lys Thr Val His Gly Ala Thr Tyr Asp Ile Leu Arg Gln His Gly
1               5                   10                  15

Leu Thr Thr Ile Phe Gly Asn Pro Gly Asp Asn Glu Leu Pro Phe Leu
            20                  25                  30

Lys Gly Phe Pro Glu Asp Phe Arg Tyr Ile Leu Gly Leu His Glu Gly
            35                  40                  45
```

```
Ala Val Val Gly Met Ala Asp Gly Tyr Ala Leu Ala Ser Gly Gln Pro
    50              55                  60
Thr Phe Val Asn Leu His Ala Ala Gly Thr Gly Asn Gly Met Gly
65              70                  75                  80
Ala Leu Thr Asn Ala Trp Tyr Ser His Ser Pro Leu Val Ile Thr Ala
                85                  90                  95
Gly Gln Gln Val Arg Ser Met Ile Gly Val Glu Ala Met Leu Ala Asn
            100                 105                 110
Val Asp Ala Ala Gln Leu Pro Lys Pro Leu Val Lys Trp Ser His Glu
            115                 120                 125
Pro Ala Thr Ala Gln Asp Val Pro Arg Ala Leu Ser Gln Ala Ile His
            130                 135                 140
Thr Ala Asn Leu Pro Pro Arg Gly Pro Val Tyr Val Ser Ile Pro Tyr
145                 150                 155                 160
Asp Asp Trp Ala Cys Glu Ala Pro Ser Gly Val Glu His Leu Ala Arg
                165                 170                 175
Arg Gln Val Ser Ser Ala Gly Leu Pro Ser Pro Ala Gln Leu Gln His
                180                 185                 190
Leu Cys Glu Arg Leu Ala Ala Arg Asn Pro Val Leu Val Leu Gly
    195                 200                 205
Pro Asp Val Asp Gly Ser Ala Ala Asn Gly Leu Ala Val Gln Leu Ala
210                 215                 220
Glu Lys Leu Arg Met Pro Ala Trp Val Ala Pro Ser Ala Ser Arg Cys
225                 230                 235                 240
Pro Phe Pro Thr Arg His Ala Cys Phe Arg Gly Val Leu Pro Ala Ala
                245                 250                 255
Ile Ala Gly Ile Ser His Asn Leu Ala Gly His Asp Leu Ile Leu Val
                260                 265                 270
Val Gly Ala Pro Val Phe Arg Tyr His Gln Phe Ala Pro Gly Asn Tyr
            275                 280                 285
Leu Pro Ala Gly Cys Glu Leu Leu His Leu Thr Cys Asp Pro Gly Glu
290                 295                 300
Ala Ala Arg Ala Pro Met Gly Asp Ala Leu Val Gly Asp Ile Ala Leu
305                 310                 315                 320
Thr Leu Glu Ala Val Leu Asp Gly Val Pro Gln Ser Val Arg Gln Met
                325                 330                 335
Pro Thr Ala Leu Pro Ala Ala Glu Pro Val Ala Asp Asp Gly Gly Leu
                340                 345                 350
Leu Arg Pro Glu Thr Val Phe Asp Leu Leu Asn Ala Leu Ala Pro Lys
        355                 360                 365
Asp Ala Ile Tyr Val Lys Glu Ser Thr Ser Thr Val Gly Ala Phe Trp
370                 375                 380
Arg Arg Val Glu Met Arg Glu Pro Gly Ser Tyr Phe Phe Pro Ala Ala
385                 390                 395                 400
Gly Gly Leu Gly Phe Gly Leu Pro Ala Ala Val Gly Val Gln Leu Ala
                405                 410                 415
Ser Pro Gly Arg Gln Val Ile Gly Val Ile Gly Asp Gly Ser Ala Asn
                420                 425                 430
Tyr Gly Ile Thr Ala Leu Trp Thr Ala Ala Gln Tyr Asn Ile Pro Val
            435                 440                 445
Val Phe Ile Ile Leu Lys Asn Gly Thr Tyr Gly Ala Leu Arg Trp Phe
450                 455                 460
```

```
Ala Asp Val Leu Asp Val Asn Asp Ala Pro Gly Leu Asp Val Pro Gly
465                 470                 475                 480

Leu Asp Phe Cys Ala Ile Ala Arg Gly Tyr Gly Val Gln Ala Val His
            485                 490                 495

Ala Ala Thr Gly Ser Ala Phe Ala Gln Ala Leu Arg Glu Ala Leu Glu
        500                 505                 510

Ser Asp Arg Pro Val Leu Ile Glu Val Pro Thr Gln Thr Ile Glu Pro
    515                 520                 525

Gly Ser Thr Glu Asn Leu Tyr Phe Gln Ser Gly Ala Leu Glu
530                 535                 540

<210> SEQ ID NO 31
<211> LENGTH: 546
<212> TYPE: PRT
<213> ORGANISM: Unknown
<220> FEATURE:
<223> OTHER INFORMATION: Bacterial

<400> SEQUENCE: 31

Met Ala Arg Phe Gly Val Arg Lys Ala Phe Gly Val Val Gly Ser Gly
1               5                   10                  15

Asn Phe His Phe Thr Asn Gly Leu Ile Gln Gly Ala Glu Phe Val
            20                  25                  30

Ala Ala Arg His Glu Gly Gly Ala Thr Thr Met Ala Asp Ala Tyr Ala
        35                  40                  45

Arg Cys Ser Gly Glu Val Ala Ala Val Ser Val His Gln Gly Cys Gly
    50                  55                  60

Leu Gly Asn Ala Thr Thr Gly Ile Gly Glu Ala Ala Lys Ser Arg Thr
65                  70                  75                  80

Pro Leu Val Val Val Thr Ala Glu Ala Thr Asp Pro Leu Ser Asn Phe
                85                  90                  95

His Ile Asp Gln Asp Ala Leu Ala Arg Ser Val Gly Ala Ser Ser Ile
            100                 105                 110

Leu Val Arg Ser Ala Lys Thr Ala Leu Ala Asp Val Arg Arg Ala Phe
        115                 120                 125

Thr Gln Ala Arg Gln Asp Arg Arg Thr Val Leu Leu Arg Leu Pro Leu
    130                 135                 140

Glu Val Gln Ala Glu Pro Phe Asp Glu Ser Leu Leu Glu Gly Leu Thr
145                 150                 155                 160

Ala Ile Glu Ala Leu Pro Gln Pro Arg Ala Ala Glu Ala Glu Val Gln
                165                 170                 175

Ala Leu Ala Ser Ile Leu Gln Arg Ala Glu Arg Pro Val Phe Leu Cys
            180                 185                 190

Gly Arg Gly Ser Arg Ala Ala Arg Ala Glu Leu Val Ala Leu Ala Asp
        195                 200                 205

Arg Cys Gly Ala Leu Leu Ala Glu Gly Ala Val Ala Lys Gly Leu Phe
    210                 215                 220

Ala Gly Glu Pro Trp Ala Ile Gly Val Ser Gly Gly Phe Ser Ser Pro
225                 230                 235                 240

Leu Thr Thr Glu Leu Ile Gln Gly Ala Asp Val Val Gly Trp Gly
                245                 250                 255

Ser Ala Leu Asn Asp Trp Thr Thr Ala His Gly Arg Leu Leu Ser Pro
            260                 265                 270

Glu Thr Thr Leu Val Gln Val Asp Leu Glu Ser Ala Ala Leu Gly Arg
        275                 280                 285
```

Asn Arg Pro Val Asp Leu Gly Ile Val Gly Asp Val Gly Gly Thr Ala
    290                 295                 300

Leu Ala Val Ala Glu Leu Leu Glu Val His Asn Gly Tyr Arg Ser Ala
305                 310                 315                 320

Glu Leu Lys Thr Arg Ile Ala Arg Glu Ile Arg Trp Arg Asp Asn Glu
                325                 330                 335

Tyr Asp Asp Val Ser Thr Gly Glu Val Ile Asp Pro Arg Thr Leu Ser
                340                 345                 350

Ala Ala Leu Asp Glu Leu Leu Pro Ala Asn Arg Val Val Gly Val Asp
                355                 360                 365

Ser Gly Asn Phe Met Gly Tyr Pro Thr Met Tyr Leu Asp Val Pro Asp
370                 375                 380

Glu Asn Gly Phe Cys Phe Thr Gln Ala Phe Ala Ser Ile Gly Leu Gly
385                 390                 395                 400

Leu Ala Thr Ala Ile Gly Thr Ala Leu Ala Arg Pro Asp Arg Phe Pro
                405                 410                 415

Val Ala Ala Cys Gly Asp Gly Gly Phe Leu Met Ser Ile Ala Glu Leu
                420                 425                 430

Glu Thr Val Val Arg Leu Lys Leu Pro Met Leu Ile Val Val Tyr Asn
    435                 440                 445

Asp His Ala Tyr Gly Ala Glu Val Tyr Phe Phe Glu Pro Gly Gly His
    450                 455                 460

Pro Ala Asp Thr Val Thr Phe Pro Asp Thr Asp Leu Ala Ala Ile Ala
465                 470                 475                 480

Arg Gly Tyr Gly Cys Asp Ala Val Thr Val Arg Thr Lys Glu Asp Leu
                485                 490                 495

Ala Glu Val Ala Thr Arg Val Ala Ala Gly Leu Asp Arg Pro Leu Val
                500                 505                 510

Val Asp Ala Lys Ile Ala Gly Phe Ser Ala Trp Trp Leu Gln Ala Ala
    515                 520                 525

Met Thr His His Gly Ser Thr Glu Asn Leu Tyr Phe Gln Ser Gly Ala
    530                 535                 540

Leu Glu
545

<210> SEQ ID NO 32
<211> LENGTH: 580
<212> TYPE: PRT
<213> ORGANISM: Unknown
<220> FEATURE:
<223> OTHER INFORMATION: Bacterial

<400> SEQUENCE: 32

Met Thr Ser Arg Ser Ser Phe Ser Pro Ser Ala Ser Glu Gln Arg
1               5                   10                  15

Gly Ala Asp Ile Phe Ala Glu Val Leu Gln Cys Glu Gly Val Arg Tyr
                20                  25                  30

Ile Phe Gly Asn Pro Gly Thr Thr Glu Leu Pro Leu Leu Asp Ala Leu
            35                  40                  45

Thr Asp Ile Thr Gly Ile His Tyr Val Leu Gly Leu His Glu Ala Ser
        50                  55                  60

Val Val Ala Met Ala Asp Gly Tyr Ala Gln Ala Ser Gly Lys Pro Gly
65                  70                  75                  80

Phe Val Asn Leu His Thr Ala Gly Gly Leu Gly Asn Ala Met Gly Ala
                85                  90                  95

```
Ile Leu Asn Ala Lys Met Ala Asn Thr Pro Leu Val Val Thr Ala Gly
                100                 105                 110

Gln Gln Asp Thr Arg His Gly Val Thr Asp Pro Leu Leu His Gly Asp
        115                 120                 125

Leu Thr Gly Ile Ala Arg Pro Asn Val Lys Trp Ala Glu Glu Ile His
130                 135                 140

His Pro Glu His Ile Pro Met Leu Leu Arg Arg Ala Leu Gln Asp Cys
145                 150                 155                 160

Arg Thr Gly Pro Ala Gly Pro Val Phe Leu Ser Leu Pro Ile Asp Thr
                165                 170                 175

Met Glu Arg Cys Thr Ser Val Gly Ala Gly Glu Ala Ser Arg Ile Glu
            180                 185                 190

Arg Ala Ser Val Ala Asn Met Leu His Ala Leu Ala Thr Ala Leu Ala
        195                 200                 205

Glu Val Thr Ala Gly His Ile Ala Leu Val Ala Gly Glu Glu Val Phe
    210                 215                 220

Thr Ala Asn Ala Ser Val Glu Ala Val Ala Leu Ala Glu Ala Leu Gly
225                 230                 235                 240

Ala Pro Val Phe Gly Ala Ser Trp Pro Gly His Ile Pro Phe Pro Thr
                245                 250                 255

Ala His Pro Gln Trp Gln Gly Thr Leu Pro Pro Lys Ala Ser Asp Ile
            260                 265                 270

Arg Glu Thr Leu Gly Pro Phe Asp Ala Val Leu Ile Leu Gly Gly His
        275                 280                 285

Ser Leu Ile Ser Tyr Pro Tyr Ser Glu Gly Pro Ala Ile Pro Pro His
    290                 295                 300

Cys Arg Leu Phe Gln Leu Thr Gly Asp Gly His Gln Ile Gly Arg Val
305                 310                 315                 320

His Glu Thr Thr Leu Gly Leu Val Gly Asp Leu Gln Leu Ser Leu Arg
                325                 330                 335

Ala Leu Leu Pro Leu Leu Ala Arg Lys Leu Gln Pro Gln Asn Gly Ala
            340                 345                 350

Val Ala Arg Leu Arg Gln Val Ala Thr Leu Lys Arg Asp Ala Arg Arg
        355                 360                 365

Thr Glu Ala Ala Glu Arg Ser Ala Arg Glu Phe Asp Ala Ser Ala Thr
    370                 375                 380

Thr Pro Phe Val Ala Ala Phe Glu Thr Ile Arg Ala Ile Gly Pro Asp
385                 390                 395                 400

Val Pro Ile Val Asp Glu Ala Pro Val Thr Ile Pro His Val Arg Ala
                405                 410                 415

Cys Leu Asp Ser Ala Ser Ala Arg Gln Tyr Leu Phe Thr Arg Ser Ala
            420                 425                 430

Ile Leu Gly Trp Gly Met Pro Ala Ala Val Gly Val Ser Leu Gly Leu
        435                 440                 445

Asp Arg Ser Pro Val Val Cys Leu Val Gly Asp Gly Ser Ala Met Tyr
    450                 455                 460

Ser Pro Gln Ala Leu Trp Thr Ala Ala His Glu Arg Leu Pro Val Thr
465                 470                 475                 480

Phe Val Val Phe Asn Asn Gly Glu Tyr Asn Ala Leu Lys Asn Phe Ala
                485                 490                 495

Arg Ala Gln Thr Asn Tyr Arg Ser Ala Arg Ala Asn Arg Phe Ile Gly
            500                 505                 510

Leu Asp Ile Ser Asp Pro Ala Ile Asp Phe Pro Ala Leu Ala Ser Ser
```

```
                515                 520                 525
Leu Gly Val Pro Ala Arg Arg Val Glu Arg Ala Gly Asp Ile Ala Ile
530                 535                 540
Ala Val Glu Asp Gly Ile Arg Ser Gly Arg Pro Asn Leu Ile Asp Val
545                 550                 555                 560
Leu Ile Ser Ser Ser Gly Ser Thr Glu Asn Leu Tyr Phe Gln Ser
                565                 570                 575
Gly Ala Leu Glu
            580

<210> SEQ ID NO 33
<211> LENGTH: 552
<212> TYPE: PRT
<213> ORGANISM: Unknown
<220> FEATURE:
<223> OTHER INFORMATION: Bacterial

<400> SEQUENCE: 33

Met Leu Arg Thr Ala Gly Glu Glu Ser Gly Val Lys Val Arg Asp Ala
1               5                   10                  15

Phe Phe Glu Val Leu Arg Ser His Gly Ile Thr Thr Val Phe Gly Asn
                20                  25                  30

Pro Gly Ser Asn Glu Leu Pro Leu Leu Arg Asp Phe Pro Asp Asp Phe
            35                  40                  45

Arg Tyr Val Leu Ala Leu His Glu Gly Ala Ala Ile Ala Met Ala Asp
        50                  55                  60

Gly Tyr Ala Leu Ala Thr Gly Arg Pro Ser Leu Val Asn Leu His Ala
65                  70                  75                  80

Ala Ala Gly Thr Gly Asn Ala Met Gly Asn Leu Thr Asn Thr Gln Ser
                85                  90                  95

Gly His Val Pro Val Val Thr Ser Gly Gln Gln Ala Arg Arg Tyr
            100                 105                 110

Thr Ala Leu Asn Ala Leu Leu Thr Asn Val Asp Ala Thr Ala Leu Ala
        115                 120                 125

Glu Pro Leu Val Lys Trp Ser Cys Glu Pro Leu Arg Pro Glu Asp Val
130                 135                 140

Pro Gln Ala Leu Ser Gln Gly Ile Leu Leu Ala Gly Ser Ala Pro Ala
145                 150                 155                 160

Gly Pro Val Tyr Leu Ser Leu Pro Leu Asp Asp Trp Asp His Gln Ala
                165                 170                 175

Asp Pro Gly Ala Leu Lys His Leu Lys Ala Arg Thr Val Gln Gly Asp
            180                 185                 190

Pro Val Val Ser Glu Pro Ala Leu Asp Leu Leu Arg Arg Arg Leu Thr
        195                 200                 205

Gly Ala Ala Asn Pro Val Met Val Val Gly Pro Gly Ile Asp Asp Ala
210                 215                 220

Thr Gly Trp Asp Gly Ala Cys Arg Leu Ala Asp Arg Leu Ala Leu Pro
225                 230                 235                 240

Val Phe Val Ala Pro Ser Pro Ser Arg Cys Pro Phe Pro Thr Arg His
                245                 250                 255

Pro Gly Tyr Arg Gly Val Leu Pro Ser Asp Ile Pro Ala Val Ala Arg
            260                 265                 270

His Phe Asp Gly His Asp Leu Val Val Ala Phe Gly Ala Ala Ile Phe
        275                 280                 285

Arg Tyr Phe Ala Phe Glu Glu Gly Asp Tyr Leu Pro Pro Gly Thr Glu
```

```
                290                 295                 300
Leu Trp Ala Val Thr Ser Asp Pro Asp Glu Ala Thr Arg Ala Pro Phe
305                 310                 315                 320

Gly Arg Ile Leu Val Gly Asn Pro Ser Asp Ala Leu Ala Arg Leu Thr
                325                 330                 335

Glu Thr Val Pro Ala Arg His Arg Pro Pro Pro Pro Leu Glu Arg
                340                 345                 350

Thr Ser Arg Leu Asn Glu Ala Gly Pro Ala Phe Ser Ala Glu Ala Ile
                355                 360                 365

Val Asp Ala Leu Asp Ala Ala Lys Asp Glu Ser Thr Val Leu Ala His
                370                 375                 380

Glu Trp Thr Ser Val Leu Thr Thr Trp Asp Arg Phe Asp Ile Ser Arg
385                 390                 395                 400

Pro Gly Ser Leu Tyr Phe Pro Ala Ser Gly Gly Leu Gly Trp Gly Leu
                405                 410                 415

Pro Ala Ala Ile Gly Leu Gln Leu Gly Asp Pro Ser Arg Arg Val Leu
                420                 425                 430

Ala Met Leu Gly Asp Gly Ala Leu His Tyr Thr Val Ser Ala Leu Trp
                435                 440                 445

Thr Ala Ala Arg Tyr Arg Val Pro Val Phe Val Val Ala Arg Asn
450                 455                 460

Gly Glu Tyr Gly Ala Leu Lys Lys Phe Thr Gln Ala Met Gln Ala Pro
465                 470                 475                 480

Gly Val Pro Gly Leu Glu Leu Pro Gly Ile Asp Ile Thr Gly Ile Ala
                485                 490                 495

Ser Ala Tyr Gly Ile Ser Ala Thr Arg Ile Asp Thr Leu Asp Ala Leu
                500                 505                 510

Thr Ala Ala Val Thr Ala Ala Leu Ala Thr Asp Glu Pro His Leu Ile
                515                 520                 525

Glu Val Pro Gln Gln Pro Leu Thr Ala Ser Gly Ser Thr Glu Asn Leu
                530                 535                 540

Tyr Phe Gln Ser Gly Ala Leu Glu
545                 550

<210> SEQ ID NO 34
<211> LENGTH: 603
<212> TYPE: PRT
<213> ORGANISM: Unknown
<220> FEATURE:
<223> OTHER INFORMATION: Bacterial

<400> SEQUENCE: 34

Met Ala Pro Tyr Arg Ala Pro His Arg Ser Pro His Ser Tyr Phe Thr
1               5                   10                  15

Met Lys Gly His Glu Ala Ile Leu Arg Gln Phe Leu Ala Asn Gly Met
                20                  25                  30

Asp His Met Phe Gly Thr Pro Gly Asp Val Gln Gly Phe Leu Asp
                35                  40                  45

Ala Leu Ala Asp Val Pro Glu Met Lys Tyr Ile Leu Thr Leu Gln Glu
50                  55                  60

Ser Ile Ala Val Leu Cys Ala Asp Gly Tyr Ala Arg Ala Arg Leu Lys
65                  70                  75                  80

Pro Ala Leu Val Gln Ile His Ser Ser Pro Gly Leu Gly Asn Ala Ile
                85                  90                  95

Gly Asn Leu Tyr Gln Ala Met Arg Gly Gln Ala Pro Leu Val Val Ile
```

```
              100                 105                 110
Gly Gly Asp Ala Gly Ile Lys Tyr Gln Ala Met Asp Ala Gln Met Ala
            115                 120                 125

Ala Asp Leu Val Ala Met Ala Glu Pro Val Thr Lys Trp Ser Ala Met
            130                 135                 140

Val Gln His Pro Ser Ser Leu Leu Arg Met Val Arg Arg Ala Ile Lys
145                 150                 155                 160

Val Ala Ala Thr Pro Pro Cys Gly Pro Val Tyr Leu Cys Leu Pro Glu
                165                 170                 175

Asp Ile Leu Asp Ala Glu Ile Thr Glu Lys Ile Ile Pro Ala His Ile
            180                 185                 190

Pro Ser Leu Glu Thr Cys Pro Gly Ser Leu Asp Leu Asp Arg Met Val
            195                 200                 205

Ser Ala Ile Gln Ser Ala Gln Asn Pro Ile Ile Leu Val Gly Asp Gly
            210                 215                 220

Val Ala Trp Thr Gly Gly Val Glu Lys Ile Val Asp Leu Ala Glu Thr
225                 230                 235                 240

Leu Gly Ala Lys Val Tyr Ser Ala Asp Gly Gly Glu Ile Asn Phe Pro
                245                 250                 255

Asp Asp His Leu Leu Asn Tyr Gly Ser Thr Gly Ala Met Phe Gly Asp
            260                 265                 270

Gln Ser Leu Pro Ile Met Gln Ser Cys Asp Leu Cys Leu Thr Leu Gly
            275                 280                 285

Cys Tyr Leu Leu Pro Glu Val Phe Pro His Leu Gly Asp Ile Phe Asn
            290                 295                 300

Glu Asp Ala Thr Ile Ile His Val Asp Thr Asn Val Asp Asn Ile Ala
305                 310                 315                 320

Lys Asn His Arg Val Asp Ile Ser Tyr Val Ala Glu Pro His Ser Val
                325                 330                 335

Val Thr Gly Leu Leu Pro Ile Leu Lys Ser Leu Ser Ser Ser Trp His
            340                 345                 350

Asn Ala Ala Gln Gln Arg Arg Ser Lys Leu Glu Ser Glu Ser Pro Val
            355                 360                 365

Val His Asn Asn Val Asp Gln Asn Tyr Gln Val Glu Pro Pro Tyr Pro
            370                 375                 380

Ser Glu Ala Tyr Asp Gly Ile Asn Arg Ser Met Arg Ser Gly Tyr Phe
385                 390                 395                 400

Ile Lys Thr Leu Ala Asp Lys Leu Pro Lys Glu Thr Ile Ile Phe Asp
                405                 410                 415

Glu Ala Leu Thr Asn Ser Pro Pro Val Asn Arg Tyr Leu Pro Gly Gln
            420                 425                 430

Lys Pro Gly Asp Arg Met Leu Thr Arg Gly Gly Ser Leu Gly Thr Gly
            435                 440                 445

Phe Pro Gly Ala Ile Gly Ala Lys Ile Ala Tyr Pro Asp Arg Cys Val
            450                 455                 460

Ile Gly Phe Ser Gly Asp Gly Gly Ser Met Tyr Thr Ile Gln Cys Leu
465                 470                 475                 480

Trp Thr Ala Val Arg His Asn Val Ala Ala Lys Phe Ile Val Cys Gln
                485                 490                 495

Asn Arg Ser Tyr Lys Leu Leu Gln Ser Asn Ile Ser Lys Phe Trp Gln
            500                 505                 510

Glu Arg Gly Ile Glu Gly Arg Phe Pro Val Pro Phe Asp Leu Ser
            515                 520                 525
```

```
Lys Pro Glu Ile Cys Phe Ser Val Ile Ala Asn Ser Phe Gly Val Ser
    530                 535                 540

Gly Glu Arg Val Val Arg Pro Asp Gln Val Gly Ala Ile Asp Arg
545                 550                 555                 560

Met Leu Asn His Asp Gly Pro Tyr Leu Ile Asn Leu Val Leu Asp Gly
                565                 570                 575

Asp Ile Arg Pro Asp Leu Ile Gly Val Arg Cys Gly Gln Gly Ser Thr
            580                 585                 590

Glu Asn Leu Tyr Phe Gln Ser Gly Ala Leu Glu
                595                 600

<210> SEQ ID NO 35
<211> LENGTH: 548
<212> TYPE: PRT
<213> ORGANISM: Artificial Sequence
<220> FEATURE:
<223> OTHER INFORMATION: Synthetic mutants of KIVD
<220> FEATURE:
<221> NAME/KEY: MISC_FEATURE
<222> LOCATION: (285)..(285)
<223> OTHER INFORMATION: Xaa is Ala, Asp, Leu or Phe
<220> FEATURE:
<221> NAME/KEY: MISC_FEATURE
<222> LOCATION: (286)..(286)
<223> OTHER INFORMATION: Xaa is Phe, Met, Ser, Thr, Trp or Tyr

<400> SEQUENCE: 35

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240
```

-continued

```
Phe Gly Lys Ser Ser Val Asp Glu Ala Leu Pro Ser Phe Leu Gly Ile
            245                 250                 255

Tyr Asn Gly Lys Leu Ser Glu Pro Asn Leu Lys Glu Phe Val Glu Ser
        260                 265                 270

Ala Asp Phe Ile Leu Met Leu Gly Val Lys Leu Thr Xaa Xaa Ser Thr
    275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
545
```

<210> SEQ ID NO 36
<211> LENGTH: 548
<212> TYPE: PRT
<213> ORGANISM: Artificial Sequence
<220> FEATURE:
<223> OTHER INFORMATION: Synthetic mutants of KIVD
<220> FEATURE:
<221> NAME/KEY: MISC_FEATURE
<222> LOCATION: (377)..(377)
<223> OTHER INFORMATION: Xaa is Ala, Phe, Met, Trp, Gln, Ile, Leu or Arg
<220> FEATURE:
<221> NAME/KEY: MISC_FEATURE
<222> LOCATION: (381)..(381)
<223> OTHER INFORMATION: Xaa is Ala, Leu, Phe, Ser, or Val
<220> FEATURE:
<221> NAME/KEY: MISC_FEATURE
<222> LOCATION: (382)..(382)
<223> OTHER INFORMATION: Xaa is Ala, Phe, Met, Trp, Ile, or Leu

<400> SEQUENCE: 36

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Xaa Gly Thr Ser Xaa Xaa Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile

```
                    405                 410                 415
Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
545

<210> SEQ ID NO 37
<211> LENGTH: 548
<212> TYPE: PRT
<213> ORGANISM: Artificial Sequence
<220> FEATURE:
<223> OTHER INFORMATION: Synthetic mutants of KIVD
<220> FEATURE:
<221> NAME/KEY: MISC_FEATURE
<222> LOCATION: (402)..(402)
<223> OTHER INFORMATION: Xaa is Ala, Ile, Leu, Met, Thr, Val, or Ser

<400> SEQUENCE: 37

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190
```

```
Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
        210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
        290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Pro Lys Ser His Phe Ile Gly Gln Pro Leu
385                 390                 395                 400

Trp Xaa Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 38
<211> LENGTH: 548
<212> TYPE: PRT
<213> ORGANISM: Artificial Sequence
<220> FEATURE:
<223> OTHER INFORMATION: Synthetic mutants of KIVD
<220> FEATURE:
<221> NAME/KEY: MISC_FEATURE
<222> LOCATION: (461)..(461)
```

<223> OTHER INFORMATION: Xaa is Ala, Met, Trp, Thr, or Val
<220> FEATURE:
<221> NAME/KEY: MISC_FEATURE
<222> LOCATION: (465)..(465)
<223> OTHER INFORMATION: Xaa is Ile or Val

<400> SEQUENCE: 38

```
Met Tyr Thr Val Gly Asp Tyr Leu Leu Asp Arg Leu His Glu Leu Gly
 1               5                  10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380
```

```
Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Xaa Glu Arg Glu
        450                 455                 460

Xaa His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 39
<211> LENGTH: 548
<212> TYPE: PRT
<213> ORGANISM: Artificial Sequence
<220> FEATURE:
<223> OTHER INFORMATION: Synthetic mutants of KIVD
<220> FEATURE:
<221> NAME/KEY: MISC_FEATURE
<222> LOCATION: (538)..(538)
<223> OTHER INFORMATION: Xaa is Ala, His, Leu, Met, Val, or Thr
<220> FEATURE:
<221> NAME/KEY: MISC_FEATURE
<222> LOCATION: (542)..(542)
<223> OTHER INFORMATION: Xaa is Ala, Phe, His, Ile, Met, Thr, Val, Trp,
      Tyr, or Leu

<400> SEQUENCE: 39

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140
```

```
Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
            165                 170                 175

Ser Leu Pro Leu Lys Lys Glu Asn Ser Thr Ser Asn Thr Ser Asp Gln
        180                 185                 190

Glu Ile Leu Asn Lys Ile Gln Glu Ser Leu Lys Asn Ala Lys Lys Pro
    195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Xaa Gly Lys Leu Xaa Ala Glu
    530                 535                 540

Gln Asn Lys Ser
545
```

<210> SEQ ID NO 40
<211> LENGTH: 570
<212> TYPE: PRT
<213> ORGANISM: Lactococcus lactis

<400> SEQUENCE: 40

```
Met Gly Ser Ser His His His His His Ser Ser Gly Leu Val Pro
1               5                   10                  15

Arg Gly Ser His Met Ala Ser Met Tyr Thr Val Gly Asp Tyr Leu Leu
                20                  25                  30

Asp Arg Leu His Glu Leu Gly Ile Glu Ile Phe Gly Val Pro Gly
            35                  40                  45

Asp Tyr Asn Leu Gln Phe Leu Asp Gln Ile Ile Ser Arg Glu Asp Met
        50                  55                  60

Lys Trp Ile Gly Asn Ala Asn Glu Leu Asn Ala Ser Tyr Met Ala Asp
65                  70                  75                  80

Gly Tyr Ala Arg Thr Lys Lys Ala Ala Ala Phe Leu Thr Thr Phe Gly
                85                  90                  95

Val Gly Glu Leu Ser Ala Ile Asn Gly Leu Ala Gly Ser Tyr Ala Glu
                100                 105                 110

Asn Leu Pro Val Val Glu Ile Val Gly Ser Pro Thr Ser Lys Val Gln
            115                 120                 125

Asn Asp Gly Lys Phe Val His His Thr Leu Ala Asp Gly Asp Phe Lys
    130                 135                 140

His Phe Met Lys Met His Glu Pro Val Thr Ala Arg Thr Leu Leu
145                 150                 155                 160

Thr Ala Glu Asn Ala Thr Tyr Glu Ile Asp Arg Val Leu Ser Gln Leu
                165                 170                 175

Leu Lys Glu Arg Lys Pro Val Tyr Ile Asn Leu Pro Val Asp Val Ala
            180                 185                 190

Ala Ala Lys Ala Glu Lys Pro Ala Leu Ser Leu Glu Lys Glu Ser Ser
        195                 200                 205

Thr Thr Asn Thr Thr Glu Gln Val Ile Leu Ser Lys Ile Glu Glu Ser
    210                 215                 220

Leu Lys Asn Ala Gln Lys Pro Val Val Ile Ala Gly His Glu Val Ile
225                 230                 235                 240

Ser Phe Gly Leu Glu Lys Thr Val Thr Gln Phe Val Ser Glu Thr Lys
                245                 250                 255

Leu Pro Ile Thr Thr Leu Asn Phe Gly Lys Ser Ala Val Asp Glu Ser
            260                 265                 270

Leu Pro Ser Phe Leu Gly Ile Tyr Asn Gly Lys Leu Ser Glu Ile Ser
        275                 280                 285

Leu Lys Asn Phe Val Glu Ser Ala Asp Phe Ile Leu Met Leu Gly Val
    290                 295                 300

Lys Leu Thr Asp Ser Ser Thr Gly Ala Phe Thr His His Leu Asp Glu
305                 310                 315                 320

Asn Lys Met Ile Ser Leu Asn Ile Asp Glu Gly Ile Ile Phe Asn Lys
                325                 330                 335

Val Val Glu Asp Phe Asp Phe Arg Ala Val Val Ser Ser Leu Ser Glu
            340                 345                 350

Leu Lys Gly Ile Glu Tyr Glu Gly Gln Tyr Ile Asp Lys Gln Tyr Glu
        355                 360                 365

Glu Phe Ile Pro Ser Ser Ala Pro Leu Ser Gln Asp Arg Leu Trp Gln
    370                 375                 380
```

-continued

```
Ala Val Glu Ser Leu Thr Gln Ser Asn Glu Thr Ile Val Ala Glu Gln
385                 390                 395                 400

Gly Thr Ser Phe Phe Gly Ala Ser Thr Ile Phe Leu Lys Ser Asn Ser
                405                 410                 415

Arg Phe Ile Gly Gln Pro Leu Trp Gly Ser Ile Gly Tyr Thr Phe Pro
            420                 425                 430

Ala Ala Leu Gly Ser Gln Ile Ala Asp Lys Glu Ser Arg His Leu Leu
        435                 440                 445

Phe Ile Gly Asp Gly Ser Leu Gln Leu Thr Val Gln Glu Leu Gly Leu
    450                 455                 460

Ser Ile Arg Glu Lys Leu Asn Pro Ile Cys Phe Ile Ile Asn Asn Asp
465                 470                 475                 480

Gly Tyr Thr Val Glu Arg Glu Ile His Gly Pro Thr Gln Ser Tyr Asn
                485                 490                 495

Asp Ile Pro Met Trp Asn Tyr Ser Lys Leu Pro Glu Thr Phe Gly Ala
            500                 505                 510

Thr Glu Asp Arg Val Val Ser Lys Ile Val Arg Thr Glu Asn Glu Phe
        515                 520                 525

Val Ser Val Met Lys Glu Ala Gln Ala Asp Val Asn Arg Met Tyr Trp
    530                 535                 540

Ile Glu Leu Val Leu Glu Lys Glu Asp Ala Pro Lys Leu Leu Lys Lys
545                 550                 555                 560

Met Gly Lys Leu Phe Ala Glu Gln Asn Lys
                565                 570
```